US006245530B1

(12) United States Patent
Alitalo et al.

(10) Patent No.: US 6,245,530 B1
(45) Date of Patent: Jun. 12, 2001

(54) RECEPTOR LIGAND

(75) Inventors: Kari Alitalo, Espoo (FI); Vladimir Joukov, Boston, MA (US)

(73) Assignees: Ludwig Institute for Cancer Research, New York, NY (US); Helsinki University Licensing, Ltd. OY, Helsinki (FI)

( * ) Notice: Subject to any disclaimer, the term of this patent is extended or adjusted under 35 U.S.C. 154(b) by 0 days.

(21) Appl. No.: 08/585,895

(22) Filed: Jan. 12, 1996

Related U.S. Application Data

(63) Continuation-in-part of application No. 08/510,133, filed on Aug. 1, 1995.

(51) Int. Cl.[7] .......................... C12N 15/12; C12N 15/63; C12N 5/10; C12N 5/16
(52) U.S. Cl. ...................... 435/69.4; 435/70.1; 435/325; 435/320.1; 536/23.51; 530/399; 935/13
(58) Field of Search ...................... 536/23.51; 435/252.3, 435/254.11, 320.1, 419, 69.4, 70.1, 325; 530/399; 935/13

(56) References Cited

U.S. PATENT DOCUMENTS

| | | |
|---|---|---|
| 5,219,739 | 6/1993 | Tischer et al. ...................... 435/69.4 |
| 5,332,671 | 7/1994 | Ferrara et al. ...................... 435/240.1 |
| 5,607,918 * | 3/1997 | Eriksson et al. ........................ 514/12 |
| 5,932,540 | 8/1999 | Jing-Shan Hu et al. . |
| 5,935,820 | 8/1999 | Jing-Shan Hu et al. . |

FOREIGN PATENT DOCUMENTS

| | | |
|---|---|---|
| 0 506 477 A1 | 3/1992 | (EP) . |
| WO 95/24473 A1 | 9/1995 | (WO) . |
| WO 95/33050 | 12/1995 | (WO) . |
| WO 95/33772 | 12/1995 | (WO) . |
| WO 96/11269 A2 | 4/1996 | (WO) . |
| WO 96/30046 | 10/1996 | (WO) . |
| WO 96/39421 | 12/1996 | (WO) . |
| WO 96/39515 | 12/1996 | (WO) . |
| 97/05250 | 2/1997 | (WO) . |
| 97/09427 | 3/1997 | (WO) . |
| 97/17442 | 5/1997 | (WO) . |

OTHER PUBLICATIONS

Reeck et al. Cell 50, 667, 1987.*
Hillier et al. y185b08.21 *Homo sapiens* cDNA clone 44993 5'. EST–STS Accession No. H05177, Jun. 21, 1995.*
Hillier et al. y186g06.r1 *Homo sapiens* cDNA clone 45138 5'. EST–STS Accession No. H07991, Jun. 23, 1995.*
Hillier et al. yd29f07.r1 *Homo sapiens* cDNA clone 109669 5' similar to SP:BAR3_CHITE Q03376 Balbiani Ring Protein 3. EST–STS Accession No. T81690, Mar. 15, 1995.*
Auffray et al. *H. sapiens* partial cDNA sequence; clone c–1wf11.EST–STS Accession No. Z44272, Nov. 6, 1994.*

Pajusola, "Cloning and Characterization of a New Endothelial Receptor Tyrosine Kinase Flt4 and Two Novel VEG-F–Like Growth Factors VEGF–B and VEGF–C," Academic Dissertation, Molecular/Cancer Biology Laboratory and Department of Pathology, Haartman Institute and Department of Biosciences, Division of Genetics, University of Helsinki, (Jan. 26, 1996).

Hillier et al., "The WashU–Merck EST Project," EMBL Database entry HS991157, accession No. H07991, Jul. 2, 1995.

Alitalo et al., "Vascular Endothelial Growth Factors and Receptors Involved in Angiogenesis," *The 9th International Conference of the International Society of Differentiation (ISD), Development, Cell Differentiation and Cancer*, Pisa (Italy), Sep. 28–Oct. 2, 1996, p. 66 (Abstract S22).

Alitalo et al., "Vascular Endothelial Growth Factors B and C and Receptors Involved in Angiogenesis," *German–American Academic Council Foundation (GAAC)/ Stiftung Deutsch–Amerikanisches Akademisches Konzil (DAAK), 2nd Symposium on Current Problems in Molecular Medicine: The Role of Cytokines in Human Disease*, Nov. 17–20, 1996, Ringberg Castle, Germany, p. 1 (Abstract).

Kukk et al., "VEGF–C Receptor Binding and Pattern of Expression with VEGFR–3 Suggests a Role in Lymphatic Vascular Development," *Development*, 122:3829–3837 (1996).

Paavonen et al., "Chromosomal Localization and Regulation of Human Vascular Endothelial Growth Factors B and C (VEGF–B and VEGF–C)," *IX International Vascular Biology Meeting*, Seattle, Washington, Sep. 4–8, 1996, p. 76 (Abstract 299).

U.S. application No. 08/207,550, Jing–Shan Huand Liang Cao, Mar. 8, 1994.

U.S. application No. 08/465,968, Crain Rosen, Jing–Shan Hu and Liang Cao, Jun. 6, 1995.

Provisional appication No. 60/003,491, James Lee and William Wood, Sep. 8, 1995.

U.S. application No. 08/554,374, Lyman, S., Nov. 8, 1995.

Achen,M.G. et al., "Vascular Endothelial Growth Factor D (VEGF–D) is a Ligand for the Tyrosine Kinases VEGF Receptor 2 (Flk1) and VEGF Receptor 3 (Flt4)," *Proceedings of the National Academy of Science*, USA, 95:548–553 (Jan., 1998).

Adams, M.D. et al., "Initial assessment of human gene diversity and expression patterns based upon 83 million nucleotides of cDNA sequence," *Nature*, 377(6547 Supplement):3–174 (Sep., 1995).

(List continued on next page.)

*Primary Examiner*—Christine Saoud
(74) *Attorney, Agent, or Firm*—Marshall, O'Toole, Gerstein, Murray & Borun

(57) ABSTRACT

Provided are ligands for the receptor tyrosine kinase, Flt4. Also provided are cDNAs and vectors encoding the ligands, pharmaceutical compositions and diagnostic reagents.

35 Claims, 30 Drawing Sheets

OTHER PUBLICATIONS

Cohen, T. et al., "VEGF$_{121}$, A Vascular Endothelial Growth Factor (VEGF) Isoform Lacking Heparin Binding Ability, Requires Cell–Surface Heparan Sulfates for Efficient Binding to the VEGF Receptors of Human Melanoma Cells" *Journal of Biological Chemistry*, 270(19):11322–11326 (May 12, 1995).

Genbank AA151613, "z127h03.s1 Soares pregnant uterus NbHPU Homo sapiens cDNA clone 503189 3'," Hillier, L. et al., Dated May 14, 1997.

Genbank AA425486 "zw46b06.r1 Soares total fetus Nb2HF8 9w Homo sapiens cDNA clone 773075 5' similar to SW:VEGF_ MOUSE Q00731 Vascular Endothelial Growth Factor Precursor," Deposited by Hillier, L. et al. Dated Oct. 16, 1997.

Genbank N31713, "yy15b12.s1 Homo sapiens cDNA clone 271295 3'," Deposited by Hillier, L. et al. Dated Jan. 10, 1996.

Genbank N31720, "yy15d12.s1 Homo sapiens cDNA clone 271319 3'," Deposited by Hillier, L. et al. Dated Jan. 10, 1996.

Genbank AA406492, "zv12g06.r1 Soares NhHMPu S1 Homo sapiens cDNA clone 75366 5'," Deposited by Hillier, L. et al. Dated May 17, 1997.

Genbank N50972, "yy94b08.s1 Homo sapiens cDNA clone 281175 3'," Deposited by Hillier, L. et al. Dated Feb. 14,1996.

Genbank AA421713, "zu24b03.s1 Soares NhHMPu S1 Homo sapiens cDNA clone 738893 3'," Deposited by Hillier, L. et al. Dated Oct. 16,1997.

Genbank N94399, "zb76f04.s1 Soares senescent fibroblasts NbHSF Homo sapiens cDNA clone 309535 3'," Deposited by Hillier, L et al. Dated Aug. 20, 1996.

Genbank H05177, "y185b08.rl Homo sapiens cDNA clone 44993 5'," Deposited by Hillier, L. et al. Dated Jun. 21, 1995.

Genbank AA479987, "zv18h12.s1 Soares NhHMPu S1 Homo sapiens cDNA clone 754055 3'," Deposited by Hillier, L. et al. Dated Aug. 8, 1997.

Genbank H05134, "y185b08.s1 Homo sapiens cDNA clone 44993 3'," Deposited by Hillier, L. et al. Dated Jun. 21, 1995.

Genbank, AA298182 "EST113866 Bone VII Homo sapiens cDNA 5' end," Deposited by Adams, M.D. et al. Dated Apr. 18, 1997.

Genbank AA298283, "EST113896 Bone VII Homo sapiens cDNA 5' end similar to similar to vascular endothelial growth factor," Deposited by Adams, M.D. et al. Dated Apr. 18, 1997.

Genbank T81481, "yd29f07.s1 Homo sapiens cDNA clone 109669 3'," Deposited by Hillier, L. et al. Dated Mar. 15, 1995.

Genbank AA425303, "zw46b06.s1 Soares total fetus Nb2HF8 9w Homo sapiens cDNA clone 773075 3', mRNA sequence," Deposited by Hillier, L. et al. Dated Oct. 16, 1997.

Genbank Z40230, "H. sapiens partial cDNA sequence; clone c–1wf11," Deposited by Genexpress. Dated Sep. 21, 1995.

Genbank Z44272, "H. sapiens partial cDNA sequence; clone c–1wf11," Deposited by Genexpress. Dated Sep. 21, 1995.

Genbank AA478766, "zv18h12.rl Soares NhHMPu S1 Homo sapiens cDNA clone 754055 5'," Deposited by Hillier, L. et al. Dated Aug. 8, 1997.

Genbank H96876, "yw04b12.s1 Soares melanocyte 2NbHM Homo sapiens cDNA clone 251231 3'," Depostied by Hillier, L. et al. Dated Nov. 25, 1996.

Genbank H96533, "yw04b12.r1 Soares melanocyte 2NbHM Homo sapiens cDNA clone 251231 5'," Deposited by Hillier, L. et al. Dated Nov. 25, 1996.

Genbank T81690, "yd29f07.r1 Homo sapiens cDNA clone 109669 5' similar to SP:BAR3_CHITE Q03376 BALBIANI RING PROTEIN 3," Deposited by Hillier, L. et al. Dated Mar. 15, 1995.

Genbank T84377, "yd37h08.r1 Homo sapiens cDNA clone 110463 5' similar to SP:BAR3_CHITE Q03376 BALBIANI RING PROTEIN 3," Deposited by Hillier, L. et al. Dated Mar. 16, 1995.

Genbank N42368, "yy15b11.rl Homo sapiens cDNA clone 271293 5', " Deposited by Hillier, L. et al. Dated Jan. 25, 1996.

Genbank N42374, "yy15b11.rl Homo sapiens cDNA clone 271317 5', " Deposited by Hillier, L. et al. Dated Jan. 25, 1996.

Genbank H81868, "yv83d09.s1 Homo sapiens cDNA clone 249329 3', " Deposited by Hillier, L. et al. Dated Nov. 9, 1995.

Genbank H81867, "yv83d09.rl Homo sapiens cDNA clone 249329 5', " Deposited bu Hillier, L. et al. Dated Nov. 9, 1995.

Genbank AA149461, "z127h03.r1 Soares pregnant uterus NbHPU Homo sapiens cDNA clone 503189 5' similar to SW:BAR3_CHITE Q03376 BALBIANI RING PROTEIN 3 PRECURSOR," Deposited by Hillier, L. et al. Dated May 14, 1997.

Genbank R77495, "yi79e04.s1 Homo sapiens cDNA clone 145470 3', " Deposited by Hillier, L. et al. Dated Jun. 7, 1995.

Genbank H07899, "y186g06.s1 Homo sapiens cDNA clone 45138 3', " Deposited by Hillier, L. et al. Dated Jun. 23, 1995.

Genbank T89295, "yd37h08.s1 Homo sapiens cDNA clone 110463 3', " Deposited by Hillier, L. et al. Dated Mar.20, 1995.

Genbank C21512, "HUMGS0010510, Human Gene Signature, 3'–directed cDNA sequence," Deposited by Okubo, K. Dated Oct. 1, 1996.

Genbank N82975, "TgESTzy53h10.r1 TgRH Tachyzoite cDNA Toxoplasma gondii cDNA clone tgzy53h10.r1 5'," Deposited by Hehl, A. et al. Dated Sep. 10, 1997.

Genbank AA285997, "vb88h06.r1 Soares mouse 3NbMS Mus musculus cDNA clone 764123 5', " Deposited by Marra, M. et al. Dated Apr. 9, 1997.

Genbank AA549856, "0929m3 gmbPfHB3.1, G. Roman Reddy Plasmodium falciparum genomic clone 0929m, " Deposited by Dame, J.B. et al. Dated Aug. 11, 1997.

Jeltsch, M. et al., "Hyperplasia of Lymphatic Vessels in VEGF–C Transgenic Mice," *Science*, 276:1423–1425 (May, 1997).

Joukov, V. et al., "Proteolytic Processing Regulates Receptor Specificity and Activity of VEGF–C," *EMBO Journal*, 16(13):3898–3911 (Jun., 1997).

Joukov, V. et al., "A Recombinant Mutant Vascular Endothelial Growth Factor–C that has Lost Vascular Endothelial Growth Factor Receptor–2 Binding, Activation, and Vascular Permeability Activities," *Journal of Biological Chemistry*, 273(12):6599–6602 (Mar. 20. 1998).

Lee, J. et al., "Vascular Endothelial Growth Factor Related Protein (vrp): A Ligand and Specific Activator of the Tyrosine Kinase Receptor Flt4," *EMBL Sequence Data Library*, XP002066361, accession No. U4142, Dated Jan. 10, 1996.

Andersson et al., "Assignment of Interchain Disulfide Bonds in platelet–Derived Growth Factor (PDGF) and Evidence for Agonist Activity of Monomeric PDGF," *J. Biol. Chem.*, 267(16):11260–11266 (Jun. 5, 1992).

Aprelikova et al., "FLT4, A Novel Class III Receptor Tyrosine Kinase in Chromosome 5q33–qter," *Cancer Research*, 52:746–748 (Feb. 1, 1992).

Ausprunk, et al., "Migration and Proliferation of Endothelial Cells in Preformed and Newly Formed Blood Vessels during Tumor Angiogenesis," *Microvasc. Res.*, 14:53–65 (1977).

Basilico et al., "The FGF Family of Growth Factors and Oncogenes," *Adv. Cancer Res.*, 59:145–165 (1992).

Berse et al., "Vascular Permeability Factor (Vascular Endothelial Growth Factor) Gene is Expressed Differentially in Normal Tissues, Macrophages, and Tumors," *Mol. Biol. Cell.*, 3:211–220 (Feb., 1992).

Betsholtz et al., "cDNA Sequence and Chromosomal Localization of Human Platelet–Derived Growth Factor A–Chain and Its Expression in Tumor Cell Lines," *Nature*, 320:695–699 (Apr., 1986).

Borg et al., "Biochemical Characterization of Two Isoforms of FLT4, a VEGF Receptor–Related Tyrosine Kinase," *Oncogene*, 10:973–84 (1995).

Breier et al., "Expression of Vascular Endothelial Growth Factor During Ebryonic Angiogenesis and Endothelial Cell Differentiation," *Development*, 114:521–532 (1992).

Cao et al., "Heterodimers of Placenta Growth Factor/Vascular Endothelial Growth Factor," *J. Biol. Chem.*, 271(6):3154–3162 (Feb. 9, 1996).

Cheng and Flanagan, "Identification and Cloning of ELF–1, A Developmentally Expressed Ligand for the Mek4 and Sek Receptor Tyrosine Kinases," *Cell*, 79:157–168 (Oct. 7, 1994).

Claesson–Welsh et al., "Identification and Structural Analysis of the A Type Receptor for Platelet–derived Growth Factor," *J. Biol. Chem.*, 264(3):1742–1747 (Jan. 25, 1989).

Coffin et al., "Angioblast Differentiation and Morphogenesis of the Vascular Endothelium in the Mouse Embryo," *Devel. Biol.*, 148:51–62 (1991).

Curran and Franza, "Fos and Jun: The AP–1 Connection," *Cell*, 55:395–397 (Nov. 4, 1988).

De Vries et al., "The fms–Like Tyrosine Kinase, a Receptor for Vascular Endothelial Growth Factor," *Science*, 255:989–991 (Feb. 21, 1992).

Dignam et al., "Balbiani Ring 3 in *Chironomus tentans* Encodes a 185–kDa Secretory Protein Which is Synthesized Throughout the Fourth Larval Instar," *Gene*, 88:133–140 (1990).

DiSalvo et al., "Purification and Characterization of a Naturally Occurring Vascular Endothelial Growth Factor: Placenta Growth Factor Heterodimer," *J. Biol. Chem.*, 270(13):7717–7723 (Mar. 31, 1995).

Don et al., "'Touchdown' PCR to Circumvent Spurious Priming During Gene Amplification," *Nucl. Acids Res.*, 19: 4008 (1991).

Dumont et al., "Dominant–negative and Targeted Null Mutations in the Endothelial Receptor Tyrosine Kinase, tek, Reveal a Critical Role in Vasculogenesis of the Embryo," *Genes Dev.*, 8:1897–1909 (1994).

Dumont et al., "Vascularization of the Mouse Embryo: A Study of flk–1, tek, tie and Vascular Endothelial Growth Factor Expression During Development," *Development Dynamics*, 203:80–92 (1995).

Dvorak et al., "Review: Vascular Permeability Factor/Vascular Endothelial Growth Factor, Microvascular Hyperpermeability, and Angiogenesis," *Amer. J. Path.*, 146:1029–1039 (1995).

Eichmann et al., "Two Molecules Related to the VEGF Receptor are Expressed in Early Endothelial Cells During Avian Embryonic Development," *Mech. Dev.*, 42:33–48 (1993).

Ferrara et al., "Molecular and Biological Properties of the Vascular Endothelial Growth Factor Family of Proteins," *Endocrine Rev.*, 13(1):18–32 (1992).

Finnerty et al., "Molecular Cloning of Murine FLT and FLT4," *Oncogene*, 8(11):2293–2298 (1993).

Flamme et al., "Vascular Endothelial Growth Factor (VEGF) and VEGF–Receptor 2 (flk–1) are Expressed During Vasculogenesis and Vascular Differentiation in the Quail Embryo," *Devel. Biol.*, 169:699–712 (1995).

Flanagan and Leder, "The kit Ligand: A Cell Surface Molecule Altered in Steel Mutant Fibroblasts," *Cell*, 63:185–194 (Oct. 5, 1990).

Folkman, "Angiogenesis in Cancer, Vascular, Rheumatoid and Other Disease," *Nature Med.*, 1(1):27–31 (1995).

Folkman et al., "Angiogenesis," *J. Biol. Chem.*, 267(16):10931–10934 (Jun. 5, 1992).

Folkman et al., "Long–term Culture of Capillary Endothelial Cells," *Proc. Nat'l Acad. Sci., USA*, 76(10):5217–5221 (Oct., 1979).

Fong et al., "Role of the Flt–1 Receptor Tyrosine Kinase in Regulating the Assembly of Vascular Endothelium," *Nature*, 376:66–70 (Jul. 6, 1995).

Fournier et al., "Mutation of Tyrosine Residue 1337 Abrogates Ligand–Dependent Transforming Capacity of the FLT4 Receptor," *Oncogene*, 11(5):921–931 (Sep. 7, 1995).

Friesel et al., "Molecular Mechanisms of Angiogenesis: Fibroblast Growth Factor Signal Transduction," *FASEB J.*, 9:919–25 (1995).

Galland et al., "The Flt4 Gene Encodes a Transmembrane Tyrosine Kinase Related to the Vascular Endothelial Growth Factor Receptor," *Oncogene*, 8:1233–1240 (1993).

Genbank S66407, "FLT4 Receptor Tyrosine Kinase Isoform FLT4 Long (3' Region, Alternatively Spliced) [Human, mRNA Partial, 216 nt].," Deposited by Pajusola et al., Dated Dec. 17, 1993.

Genbank U48800, "Mus Musculus Vascular Endothelial Growth Factor B Precursor (VEGF–B) mRNA, Complete Cds.," Deposited by Olofsson et al., Dated Aug. 19, 1996.

Genbank X15997, "Human Vascular Permeability Factor mRNA, Complete Cds.," Deposited by Keck et al., Dated Jun. 15, 1990.

Genbank X60280, "Vector Plasmid pLTRpoly DNA.," Deposted by Maekelae, T.P., Dated Jul. 16, 1996.

Genbank X68203, "*H. sapiens* mRNA for FLT4, Class III Receptor Tyrosine Kinase.," Deposited by Aprelikova, O., Dated Nov. 30, 1993.

Genbank X94216, "*Homo sapiens* mRNA for VEGF–C protein," Deposited by Joukov et al., Dated Feb. 6, 1996.

Harlow et al., *Antibodies, a Laboratory Manual*, Cold Spring Harbor Laboratory Press, pp. 72–137, 141–157, 287 & 321–358 (1988).

Heldin et al., "Structure of Platelet–Derived Growth Factor: Implications for Functional Properties," *Growth Factors*, 8:245–252 (1993).

Joukov et al., "A Novel Vascular Endothelial Growth Factor, VEGF–C, Is a Ligand for the Flt4 (VEGFR–3) and KDR (VEGFR–2) Receptor Tyrosine Kinases," *EMBO J.*, 15(2):290–298 (1996).

Kaipainen et al., "Expression of the FMS–Like Tyrosine Kinase 4 Gene Becomes Restricted to Lymphatic Endothelium During Development," *Proc. Nat'l Acad. Sci., USA*, 92:3566–3570 (Apr., 1995).

Kaipainen et al., "The Related FLT4, FLT1 and KDR Receptor Tyrosine Kinases Show Distinct Expression Patterns in Human Fetal Endothelial Cells," *J. Exp. Med.*, 178:2077–2088 (Dec., 1993).

Kaipainen et al., "Enhanced Expression of the Tie Receptor Tyrosine Kinase Messenger RNA in the Vascular Endothelium of Metastatic Melanomas," *Cancer Res.*, 54:6571–6577 (Dec. 15, 1994).

Kozak, "An Analysis of 5'–Non–Coding Sequences from 699 Vertebrate Messenger RNAs," *Nucl. Acids Res.* 15:8125–8148 (1987).

Lee et al., "Vascular Endothelial Growth Factor–Related Protein: A Ligand and Specific Activator of the Tyrosine Kinase Receptor Flt4," *Proc. Nat'l Acad. Sci., USA*, 93:1988–1992 (Mar., 1996).

Leung et al., "Vascular Endothelial Growth Factor Is a Secreted Angiogenic Mitogen," *Science*, 246:1306–1309 (Dec. 8, 1989).

Levy et al., "Post–transcriptional Regulation of Vascular Endothelial Growth Factor by Hypoxia," *J. Biol. Chem.*, 271(5):2746–2753 (Feb. 2, 1996).

Levy et al., "Transcriptional Regulation of the Rat Vascular Endothelial Growth Factor Gene by Hypoxia," *J. Biol. Chem.*, 270(22):13333–13340 (Jun. 2, 1995).

Lyman et al., "Molecular Cloning of a Ligand for the flt3/flk–2 Tyrosine Kinase Receptor: A Proliferative Factor for Primitive Hematopoietic Cells," *Cell*, 75:1157–1167 (Dec. 17, 1993).

Maglione et al., "Isolation of a Human Placenta cDNA Coding for a Protein Related to the Vascular Permeability Factor," *Proc. Nat'l Acad. Sci., USA*, 88:9267–9271 (Oct., 1991).

Maglione et al., "Two Alternative mRNAs Coding for the Angiogenic Factor, Placenta Growth Factor (P1GF) are Transcribed from a Single Gene of Chromosome 14," *Oncogene*, 8:925–931 (1993).

Mäkelä et al., "Plasmid pLTRpoly: A Versatile High–Efficiency Mammalian Expression Vector," *Gene*, 118: 293–294 (1992).

Matthews et al., "A Receptor Tyrosine Kinase cDNA Isolated from a Population of Enriched Primitive Hematopoietic Cells and Exhibiting Close Genetic Linkage to c–kit," *Proc. Nat'l Acad. Sci., USA*, 88:9026–9030 (Oct., 1991).

Metzelaar et al., "CD63 Antigen," *J. of Biol. Chem.*, 266(5):3239–3245 (Feb. 15, 1991).

Millauer et al., "Glioblastoma Growth Inhibited in vivo by a Dominant–Negative Flk–1 Mutant," *Nature*, 367:576–579 (Feb. 10, 1994).

Millauer et al., "High Affinity VEGF Binding and Developmental Expression Suggest Flk–1 as a Major Regulator of Vasculogenesis and Angiogenesis," *Cell*, 72:835–846 (Mar. 26, 1993).

Mitchell et al., "Transcription Factor AP–2 is Expressed in Neural Crest Cell Lineages During Mouse Embryogenesis," *Genes and Dev.*, 5:105–119 (1991).

Morgenstern et al., "Advanced Mammalian Gene Transfer: High Titre Retroviral Vectors With Multiple Drug Selection Markers and a Complementary Helper–Free Packaging Cell Line," *Nucl. Acids Res.*, 18(12):3587–3595 (1990).

Mount, S.M., "A Catalogue of Splice Junction Sequences," *Nucl. Acids Res.*, 10(2):459–472 (1982).

Mustonen et al., "Endothelial Receptor Tyrosine Kinases Involved in Angiogenesis," *J. Cell Biol.*, 129:895–898 (May, 1995).

Nelson and Sun, "The 50– and 58–kdalton Keratin Classes as Molecular Markers for Stratified Squamous Epithelia: Cell Culture Studies," *J. Cell Biol.*, 97:244–251 (Jul., 1983).

Neufeld et al., "Vascular Endothelial Growth Factor and Its Receptors," *Prog. Growth Fact. Res.*, 5:89–97 (1994).

Oefner et al., "Crystal Structure of Human Platelet–derived Growth Factor BB," *EMBO J.*, 11(11):3921–3926 (1992).

Oelrichs et al., "NYK/FLK–1: A Putative Receptor Tyrosine Kinase Isolated from E10 Embryonic Neuroepithelium is Expressed in Endothelial Cells of the Developing Embryo," *Oncogene*, 8:11–18 (1993).

Olofsson et al., "Vascular Endothelial Growth Factor B, A Novel Growth Factor for Endothelial Cells," *Proc. Nat'l Acad. Sci., USA*, 93:2576–2581 (Mar., 1996).

Paavonen et al., "Novel Human Vascular Endothelial Growth Factor Genes VEGF–B and VEGF–C Localize to Chromosomes 11q13 and 4q34, Respectively," *Circulation* 93(6):1079–1082 (Mar. 15, 1996).

Pajusola et al., "FLT4 Receptor Tyrosine Kinase Contains Seven Immunoglobulin–Like Loops and Is Expressed in Multiple Human Tissues and Cell Lines," *Cancer Res.*, 52:5738–5743 (Oct. 15, 1992).

Pajusola et al., "Signalling Properties of FLT4, a Proteolytically Processed Receptor Tyrosine Kinase Related to Two VEGF Receptors," *Oncogene*, 9:3545–3555 (1994).

Pajusola et al., "Two Human FLT4 Receptor Tyrosine Kinase Isoforms With Distinct Carboxy Terminal Tails are Produced by Alternative Processing of Primary Transcripts," *Oncogene*, 8: 2931–2937 (1993).

Park et al., "Placenta Growth Factor, Potentiation of Vascular Endothelial Growth Factor Bioactivity In vitro and In vivo, and High Affintiy Binding to Flt–1 but not to Flk–1/KDR," *J. Biol. Chem.*, 269(41):25646–25654 (Oct. 14, 1994).

Partanen et al., "A Novel Endothelial Cell Surface Receptor Tyrosine Kinase with Extracellular Epidermal Growth Factor Homology Domains," *Mol. & Cell. Biol.*, 12(4):1698–1707 (Apr., 1992).

Partanen et al., "Putative Tyrosine Kinases Expressed in K–562 Human Leukemia Cells," *Proc. Nat'l Acad. Sci., USA*, 87:8913–8917 (Nov., 1990).

Paulsson et al., "The Balbiani Ring 3 Gene in *Chironomus tentans* has a Diverged Repetitive Structure Split by Many Introns," *J. Mol. Biol.*, 211:331–349 (1990).

Pear et al., "Production of High–titer Helper–free Retroviruses by Transient Transfection," *Proc. Nat'l Acad. Sci., USA*, 90:8392–8396 (Sep., 1993).

Pertovaara et al., "Vascular Endothelial Growth Factor Is Induced in Response to Transforming Growth Factor–β in Fibroblastic and Epithelial Cells," *J. Biol. Chem.*, 269(9):6271–6274 (Mar. 4, 1994).

Peters et al., "Vascular Endothelial Growth Factor Receptor Expression during Embryogenesis and Tissue Repair Suggests a Role in Endothelial Differentiation and Blood Vessel Growth," *Proc. Nat'l Acad. Sci., USA*, 90:8915–8918 (Oct., 1993).

Pötgens et al., "Covalent Dimerization of Vascular Permeability Factor/Vascular Endothelial Growth Factor Is Essential for Its Biological Activity," *J. Biol. Chem.*, 269(52):32879–32885 (Dec. 30, 1994).

Puri et al., "The Receptor Tyrosine Kinase TIE is Required for Integrity and Survival of Vascular Endothelial Cells," *EMBO J.*, 14:5884–5891 (1995).

Quinn et al., "Fetal Liver Kinase 1 is a Receptor for Vascular Endothelial Growth Factor and is Selectively Expressed in Vascular Endothelium," *Proc. Nat'l Acad. Sci., USA*, 90:7533–7537 (Aug., 1993).

Risau et al., "Changes on the Vascular Extracellular Matrix During Embryonic Vasculogenesis and Angiogenesis," *Devel. Biol.*, 125:441–450 (1988).

Risau et al., "Platelet–Derived Growth Factor is Angiogenic In Vivo," *Growth Factors*, 7:261–266 (1992).

Risau, W., "Differentiation of Endothelium," *FASEB J.*, 9:926–933 (1995).

Sabin, F.R., "The Lymphatic System in Human Embryos, With A Consideration of the Morphology of the System as a Whole," *Am. J. Anat.*, 9(1):43–91 (1909).

Saksela et al., "Cell–Associated Plasminogen Activation: Regulation and Physiological Function ," *Ann. Rev. Cell Biol.*, 4:93–126 (1988).

Sambrook et al., *Molecular Cloning: a Laboratory Manual*, Second Edition, Cold Spring Harbor, New York: Cold Spring Harbor Laboratory (1989), pp. 2.60–2.79, 4.21–4.32, 7.3–7.36, and 9.47–9.51.

Sato et al., "Distinct Roles of the Receptor Tyrosine Kinases Tie–1 and Tie–2 in Blood Vessel Formation," *Nature*, 376:70–74 (Jul. 6, 1995).

Schneider et al., "A One–step Purification of Membrane Proteins Using a High Efficiency Immunomatrix," *J. Biol. Chem.*, 257(18):10766–70769 (Sep. 25, 1982).

Seetharam et al., "A Unique Signal Transduction from FLT Tyrosine Kinase, a Receptor for Vascular Endothelial Growth Factor VEGF," *Oncogene*, 10:135–147 (1995).

Senger et al., "Tumor Cells Secrete a Vascular Permeability Factor That Promotes Accumulation of Ascites Fluid," *Science*, 219:983–985 (Feb. 25, 1983).

Shalaby et al., "Failure of Blood–Island Formation and Vasculogenesis in Flk–1–deficient Mice," *Nature*, 376:62–66 (Jul. 6, 1995).

Shibuya et al., "Nucleotide Sequence and Expression of a Novel Human Receptor–Type Tyrosine Kinase Gene (flt) Closely Related to the fms Family," *Oncogene*, 5:519–524 (1990).

Shibuya, M., "Role of VEGF–FLT Receptor System in Normal and Tumor Angiogenesis," *Adv. Cancer Res.*, 67:281–316 (1995).

Shweiki et al., "Patterns of Expression of Vascular Endothelial Growth Factor (VEGF) and VEGF Receptors in Mice Suggest a Role in Hormonally Regulated Angiogenesis," *J. Clin. Invest.*, 91:2235–2243 (May, 1993).

Sitaras et al., "Constitutive Production of Platelet–Derived Growth Factor–Like Proteins by Human Prostate Carcinoma Cell Lines," *Cancer Research*, 48(7):1930–1935 (Apr. 1, 1988).

Southern and Berg, "Transformation of Mammalian Cells to Antibiotic Resistance with a Bacterial Gene Under Control of the SV40 Early Region Promoter," *J. Mol. Appl. Genet.*, 1:327–341 (1982).

Terman et al., "Identification of New Endothelial Cell Growth Factor Receptor Tyrosine Kinase," *Oncogene*, 6:1677–1683 (1991).

Terman et al., "Identification of the KDR Tyrosine Kinase as a Receptor for Vascular Endothelial Cell Growth Factor," *Biochem. Biophys. Res. Commun.*, 187:1579–1586 (Sep. 30, 1992).

Terman et al., "VEGF Receptor Subtypes KDR and FLT1 Show Different Sensitivities to Heparin and Placenta Growth Factor," *Growth Factors*, 11(3):187–195 (1994).

Tessier et al., "Enhanced Secretion From Insect Cells of a Foreign Protein Fused to the Honeybee Melittin Signal Peptide," *Gene*, 98: 177–183 (1991).

Tischer et al., "The Human Gene for Vascular Endothelial Growth Factor. Multiple Protein Forms are Encoded Through Alternative Exon Splicing," *J. Biol. Chem.*, 266(18):11947–11954 (Jun. 25, 1991).

Van der Geer et al., "Repeptor Protein–Tyrosine Kinases and Their Signal Transduction Pathways," *Ann. Rev. Cell Biol.*, 10:251–337 (1994).

Vassar et al., "Tissue–specific and Differentiation –specific Expression of a Human K14 Keratin Gene in Transgenic Mice," *Proc. Nat'l Acad,. Sci., USA*, 86:1563–1567 (Mar., 1989).

Vassar et al., "Transgenic Mice Provide New Insights Into the Role of TGF–α During Epidermal Development and Differentiation," *Genes & Dev.*, 5:714–727 (1991).

Västrik et al., "Expression of the Mad Gene During Cell Differentiation In Vivo and Its Inhibition of Cell Growth In Vitro," *J. Cell. Biol.*, 128(6):1197–1208 (Mar., 1995).

von Heijne, G., "A New Method for Predicting Signal Sequence Cleavage Sites," *Nucleic Acids Res.*, 14(11):4683–4690 (1986).

Waltenberger et al., "Different Signal Transduction Properties of KDR and Flt1, Two Receptors for Vascular Endothelial Growth Factor," *J. Biol. Chem*, 269(43):26988–26995 (Oct. 28, 1994).

Wanaka et al., "Expression of FGF Receptor Gene in Rat Development," *Development*, 111:455–468 (1991).

Wen et al., "Neu Differentiation Factor: A Transmembrane Glycoprotein Containing an EGF Domain and an Immunoglobulin Homology Unit," *Cell* 69:559–572 (May 1, 1992).

Yamane et al., "A New Communication System Between Hepatocytes and Sinusoidal Endothelial Cells in Liver Through Vascular Endothelial Growth Factor and Flt Tyrosine Kinase Receptor Family (Flt–1 and KDR/Flk–1)," *Oncogene*, 9:2683–2690 (1994).

* cited by examiner

```
                                                        MetThrValLeuTyrProGluTyr
GAGCAGTTACGGTCTCTGTGTCCAGTGTAGATGAACTCATGACTGTACTCTACCCAGAATAT
         10                  30                   50

TrpLysMetTyrLysCysGlnLeuArgLysGlyGlyTrpGlnHisAsnArgGluGlnAla
TGGAAAATGTACAAGTGTCAGCTAAGGAAAGGAGGCTGGCAACATAACAGAGAACAGCC
         70                  90                   110

AsnLeuAsnSerArgThrGluGluThrIleLysPheAlaAlaAlaHisTyrAsnThrGlu
AACCTCAACTCAAGGACAGAGAAGAGACTATAAAATTTGCTGCAGCACATTATAATACAGAG
         130                 150                  170

IleLeuLysSerIleAspAsnGluTrpArgLysThrGlnCysMetProArgGluValCys
ATCTTGAAAAGTATTGATAATGAGTGGAGAAAGACTCAATGCCACGGGAGGTGTGT
         190                 210                  230

IleAspValGlyLysGluPheGlyValAlaThrAsnThrPhePheLysProProCysVal
ATAGATGTGGGGAAGGAGTTTGGAGTCGCGACAAACACCTTCTTTAAACCTCCATGTGTG
         250                 270                  290

SerValTyrArgCysGlyGlyCysCysAsnSerGluGlyLeuGlnCysMetAsnThrSer
TCCGTCTACAGATGTGGGGGTTGCTGCAATAGTGAGGGGCTGCAGTGCATGAACACCAGC
         310                 330                  350

FIG. 9B
```

```
ThrSerTyrLeuSerLysThrLeuPheGluIleThrValProLeuSerGlnGlyProLys
ACGAGCTACCTCAGCAAGACGTTATTTGAAATTACAGTGCCTCTCTCTCAAGCCCCAAA
          370                 390                 410

ProValThrIleSerPheAlaAsnHisThrSerCysMetSerLysLeuAspVal
CCAGTAACAATCAGTTTTGCCAATCACACTTCCTGCCGATGCATGTCTAAACTGGATGTT
          430                 450                 470

TyrArgGlnValHisSerIleIleArgSerLeuProGlnAlaThrLeuProGlnCysGln
TACAGACAAGTTCATTCCATTATTAGACGTTCCCTGCCAGCAACACTACCACAGTGTCAG
   490                 510                 530

AlaAlaAsnLysThrCysProThrAsnTyrMetTrpAsnAsnHisIleCysArgCysLeu
GCAGCGAACAAGACCTGCCCCACCAATTACATGTGGAATAATCACATCTGCAGATGCCTG
          550                 570                 590

AlaGlnGluAspPheMetPheSerSerAspAlaGlyAspAspSerThrAspGlyPheHis
GCTCAGGAAGATTTTATGTTTTCCTCGGATGCTGGAGATGACTCAACAGATGGATTCCAT
          610                 630                 650

AspIleCysGlyProAsnLysGluLeuAspGluGluThrCysGlnCysValCysArgAla
GACATCTGTGGACCCAACAAGGAGCTGGATGAAGAGACCTGTCAGTGTGTCTGCAGAGCG
          670                 690                 710

GlyLeuArgProAlaSerCysGlyProHisLysGluLeuAspArgAsnSerCysGlnCys
GGGCTTCGGCCTGCCAGCTGTGGACCCCACAAAGAACTAGACAGAAACTCATGCCAGTGT
          730                 750                 770
```

FIG. 9C

```
ValCysLysAsnLysLeuPheProSerGlnCysGlyAlaAsnArgGluPheAspGluAsn
GTCTGTAAAAACAAACTCTTCCCCAGCCAATGTGGGCCAACCGAGAATTGATGAAAAC
         790                      810                      830

ThrCysGlnCysValCysLysArgThrCysProArgAsnGlnProLeuAsnProGlyLys
ACATGCCAGTGTGTGTATGTAAAAGAACCTGCCCCAGAAATCAACCCCTAAATCCTGAAAA
         850                      870                      890

CysAlaCysThrGluCysSerProGlnLysCysLeuLeuLysGlyLysLysPheHis
TGTGCCTGTGAATGTACAGAAAGTCCACAGAAATGCTTGTTAAAGGAAAGAAGTTCCAC
         910                      930                      950

HisGlnThrCysSerCysTyrArgArgProCysThrAsnArgGlnLysAlaCysGluPro
CACCAAACATGCAGCTGTTACAGACGGCCATGTACGAACCGCCAGAAGGCTTGTGAGCCA
         970                      990                      1010

GlyPheSerTyrSerGluGluValCysArgCysValProSerTyrTrpLysArgProGln
GGATTTTCATATAGTGAAGAAGTGTGTCGTTGTGTCCCTTCATATTGGAAAAGACCACAA
         1030                     1050                     1070

MetSerEnd
ATGAGCTAAGATTGTACTGTTTTCCAGTTCATCGATTTCTATTATGGAAAACTGTGTTG
         1090                     1110                     1130
```

FIG. 9D

```
                1                                                         50
PDGF-A     .MRTWACLLL LGCGYLAHAL AEEAEIPREL IERLARSQIH SIRDLQRLLE
PDGF-B     MNRCWA.LFL SLCCYLRLVS AEGDPIPEEL YEMLSDHSIR SFDDLQRLLH
P1GF-1     .......... .......... .......... ....MPVM RLFPC..FLQ LLAGLAL...
P1GF-2     .......... .......... .......... ....MPVM RLFPC..FLQ LLAGLAL...
VEGF121    .......... .......... .......... ........M NFLLS..WVH WSLALLLYLH
VEGF165    .......... .......... .......... ........M NFLLS..WVH WSLALLLYLH
VEGF189    .......... .......... .......... ........M NFLLS..WVH WSLALLLYLH
VEGF206    .......... .......... .......... ........M NFLLS..WVH WSLALLLYLH
FLT4-L     .......... .......... .......... ........M TVLYPEYWKM YKCQLRKGGW 51                                                        100
PDGF-A     IDSVGAEDAL ETSLRAHGSH AINHVPEKRP VPIRRKRSI. ......EEAIP
PDGF-B     GDP.GEEDGA ELDLNMTRSH SGGELES... .LARGRRSLG SLTIAEPAMI
P1GF-1     PAVPPQQW.. .......... ALSAG NGSSEVEVVP FQE.VWGR..
P1GF-2     PAVPPQQW.. .......... ALSAG NGSSEVEVVP FQE.VWGR..
VEGF121    HAKWSQAA.. ........PMAEG GGQNHHEVVK FMD.VYQR..
VEGF165    HAKWSQAA.. ........PMAEG GGQNHHEVVK FMD.VYQR..
VEGF189    HAKWSQAA.. ........PMAEG GGQNHHEVVK FMD.VYQR..
VEGF206    HAKWSQAA.. ........PMAEG GGQNHHEVVK FMD.VYQR..
FLT4-L     QHNREQANLN SRTEETIKFA AAHYNTEILK SIDNEWRK..
```

FIG. 10A

```
             101                                                             150
PDGF-A       AVCKTRTVIY  EIPRSQVDPT  SANFLIWPPC  VEVKRCTGCC  NTSSVKCQPS
PDGF-B       AECKTRTEVF  EISRRLIDRT  NANFLVWPPC  VEVQRCSGCC  NNRNVQCRPT
P1GF-1       SYCRALERLV  DVVSEYPS..  EVEHMFSPSC  VSLLRCTGCC  GDENLHCVPV
P1GF-2       SYCRALERLV  DVVSEYPS..  EVEHMFSPSC  VSLLRCTGCC  GDENLHCVPV
VEGF121      SYCHPIETLV  DIFQEYPD..  EIEYIFKPSC  VPLMRCGGCC  NDEGLECVPT
VEGF165      SYCHPIETLV  DIFQEYPD..  EIEYIFKPSC  VPLMRCGGCC  NDEGLECVPT
VEGF189      SYCHPIETLV  DIFQEYPD..  EIEYIFKPSC  VPLMRCGGCC  NDEGLECVPT
VEGF206      SYCHPIETLV  DIFQEYPD..  EIEYIFKPSC  VPLMRCGGCC  NDEGLECVPT
FLT4-L       TQCMPREVCI  DVGKEFGV..  ATNTFFKPPC  VSVYRCGGCC  NSEGLQCMNT 151                                                             200
PDGF-A       RVHHRSVKVA  KVEYVRKKPK  LKEVQVRLEE  HLECACAT..  ..........SN
PDGF-B       QVQLRPVQVR  KIEIVRKKPI  FKKATVTLED  HLACKCETVA  AARPVTRSPG
P1GF-1       ETANVTMQLL  KIRSG..DRP  .SYVELTFSQ  HVRCECRPLR  EKMKPER....
P1GF-2       ETANVTMQLL  KIRSG..DRP  .SYVELTFSQ  HVRCECRPLR  EKMKPERRR.
VEGF121      EESNITMQIM  RIKPH..QGQ  .HIGEMSFLQ  HNKCECRPKK  DRARQEKCD.
VEGF165      EESNITMQIM  RIKPH..QGQ  .HIGEMSFLQ  HNKCECRPKK  DRARQEN...
VEGF189      EESNITMQIM  RIKPH..QGQ  .HIGEMSFLQ  HNKCECRPKK  DRARQEKKS.
VEGF206      EESNITMQIM  RIKPH..QGQ  .HIGEMSFLQ  HNKCECRPKK  DRARQEKKS.
FLT4-L       STSYLSKTLF  EITVPLSQGP  .KPVTISFAN  HTSCRCMSKL  DVYRQHSII
```

FIG. 10B

```
                                                                                        250
         201
PDGF-A   LNPDHREEET DVR........ .......... VRRPPKGKHR KFKHTHDKTA LKETLGA...
PDGF-B   GSQEQRAKTP QTRVTIRTVR ..........    ...CGDAVPR R.........  .........
PIGF-1   .......... .......... ..PKGRGK     RRREKQRPTD CHLCGDAVPR R.........  .........
PIGF-2   .......... .......... ....KPRR..   .......... .......... .......... .......... P
VEGF121  .......... .......... .VRGKGK       GQKRKRKKSR YKSWSV.... .......... .......... 
VEGF165  .......... .......... .VRGKGK       GQKRKRKKSR YKSWSV.... .......... .......... 
VEGF189  .......... .......... .VRGKGK       GQKRKRKKSR YKSWSVYVGA RCC.....L  MPWSLPGPHP
VEGF206  .......... .......... .VRGKGK       GQKRKRKKSR YKSWSVYVGA RCC.....L  MPWSLPGPHP
FLT4-L   RRSLPATLPQ CQAANKTCPT NYMWNNHICR    CLAQEDFMFS SDAGDDSTDG 300
         251
PDGF-A   .......... .......... CGPCSERRKH LFVQDPQTCK CSCKNTDSRC KARQLELNER TCRCDKPRR.
PDGF-B   .......... .......... CGPCSERRKH LFVQDPQTCK CSCKNTDSRC KARQLELNER TCRCDKPRR.
PIGF-1   .......... .......... CGPCSERRKH LFVQDPQTCK CSCKNTDSRC KARQLELNER TCRCDKPRR.
PIGF-2   .......... .......... CGPCSERRKH LFVQDPQTCK CSCKNTDSRC KARQLELNER TCRCDKPRR.
VEGF121  .......... .......... .......... .......... .......... .......... ..........
VEGF165  .......... .......... .......... .......... .......... .......... ..........
VEGF189  .......... .......... .......... .......... .......... .......... ..........
VEGF206  .......... .......... .......... .......... .......... .......... ..........
FLT4-L   .......... .......... FHDICGPNKE RAGLRPASCG PHKELDRNSC QCVCKNKLFP
```

FIG. 10C

```
          301                                                                 350
PDGF-A    ..........  ..........  ..........  ..........  ..........
PDGF-B    ..........  ..........  ..........  ..........  ..........
P1GF-1    ..........  ..........  ..........  ..........  ..........
P1GF-2    ..........  ..........  ..........  ..........  ..........
VEGF121   ..........  ..........  ..........  ..........  ..........
VEGF165   ..........  ..........  ..........  ..........  ..........
VEGF189   ..........  ..........  ..........  ..........  ..........
VEGF206   ..........  ..........  ..........  ..........  ..........
FLT4-L    SQCGANREFD  ENTCQCVCKR  TCPRNQPLNP  GKCACECTES  PQKCLLKGKK 351                                                       395
PDGF-A    ..........  ..........  ..........  ..........  .....
PDGF-B    ..........  ..........  ..........  ..........  .....
P1GF-1    ..........  ..........  ..........  ..........  .....
P1GF-2    ..........  ..........  ..........  ..........  .....
VEGF121   ..........  ..........  ..........  ..........  .....
VEGF165   ..........  ..........  ..........  ..........  .....
VEGF189   ..........  ..........  ..........  ..........  .....
VEGF206   ..........  ..........  ..........  ..........  .....
FLT4-L    FHHQTCSCYR  RPCTNRQKAC  EPGFSYSEEV  CRCVPSYWKR  PQMS
```

FIG. 10D

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

TGTCCTCGCT GTCCTTGTCT                                                    20

(2) INFORMATION FOR SEQ ID NO:2:

(i) SEQUENCE CHARACTERISTICS:
       (A) LENGTH: 70 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

ACATGCATGC CACCATGCAG CGGGGCGCCG CGCTGTGCCT GCGACTGTGG CTCTGCCTGG         60

GACTCCTGGA                                                               70

(2) INFORMATION FOR SEQ ID NO:3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

ACATGCATGC CCCGCCGGTC ATCC                                               24

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

CGGAATTCCC CATGACCCCA AC                                                 22

(2) INFORMATION FOR SEQ ID NO:5:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

CCATCGATGG ATCCTACCTG AAGCCGCTTT CTT                33

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ATTTAGGTGA CACTATA                                  17

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCATCGATGG ATCCCGATGC TGCTTAGTAG CTGT                34

(2) INFORMATION FOR SEQ ID NO:8:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Pro Met Thr Pro Thr Thr Tyr Lys Gly Ser Val Asp Asn Gln Thr Asp
1            5                  10               15

Ser Gly Met Val Leu Ala Ser Glu Glu Phe Glu Gln Ile Glu Ser Arg
          20                 25               30

His Arg Gln Glu Ser Gly Phe Arg
        35              40

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CTGGAGTCGA CTTGGCGGAC T                             21

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:10:

CGCGGATCCC TAGTGATGGT GATGGTGATG TCTACCTTCG ATCATGCTGC CCTTATCCTC      60

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCCAAGCTTG GATCCAAGTG GCTACTCCAT GACC      34

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTTGCCTGTG ATGTGCACCA      20

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Xaa Glu Glu Thr Ile Lys Phe Ala Ala Ala His Tyr Asn Thr Glu Ile
1               5                   10                  15

Leu Lys (2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GCAGARGARA CNATHAA      17

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Glu Glu Thr Ile Lys
1               5

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

GCAYTTNARD ATYTCNGT                                                     18

(2) INFORMATION FOR SEQ ID NO:17:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Thr Glu Ile Leu Lys
1               5

(2) INFORMATION FOR SEQ ID NO:18:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

ATTCGCTGCA GCACACTACA AC                                                22

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

TCNGTGTTGT AGTGTGCTG                                                    19

(2) INFORMATION FOR SEQ ID NO:20:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:20:

Ala Ala His Tyr Asn Thr Glu
1               5

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TAATACGACT CACTATAGGG                                              20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTTGTAGTGT GCTGCAGCGA ATTT                                         24

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Lys Phe Ala Ala Ala His Tyr Asn
1               5

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TCACTATAGG GAGACCCAAG C                                            21

(2) INFORMATION FOR SEQ ID NO:25:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
TCACTATAGG GAGACCCAAG CTTGGTACCG AGCTCGGATC CACTAGTAAC GGCCGCCAGT      60

GTGGTGGAAT TCGACGAACT CATGACTGTA CTCTACCCAG AATATTGGAA AATGTACAAG     120

TGTCAGCTAA GGCAAGGAGG CTGGCAACAT AACAGAGAAC AGGCCAACCT CAACTCAAGG     180

ACAGAAGAGA CTATAAAATT CGCTGCAGCA CACTACAAC                            219
```

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
ACAGAGAACA GGCCAACC                                                   18
```

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
TCTAGCATTT AGGTGACAC                                                  19
```

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
AAGAGACTAT AAAATTCGCT GCAGC                                           25
```

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
CCCTCTAGAT GCATGCTCGA                                                 20
```

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GTTGTAGTGT GCTGCAGCGA ATTT 24

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TCACTATAGG GAGACCCAAG C 21

(2) INFORMATION FOR SEQ ID NO:32:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 37..1086

(ix) FEATURE:
        (A) NAME/KEY: mat_peptide
        (B) LOCATION: 136..1086

(xi) SEQUENCE DESCRIPTION: SEQ ID NO:32:

```
GAGCAGTTAC GGTCTGTGTC CAGTGTAGAT GAACTC ATG ACT GTA CTC TAC CCA      54
                                       Met Thr Val Leu Tyr Pro
                                       -33              -30

GAA TAT TGG AAA ATG TAC AAG TGT CAG CTA AGG AAA GGA GGC TGG CAA     102
Glu Tyr Trp Lys Met Tyr Lys Cys Gln Leu Arg Lys Gly Gly Trp Gln
    -25                 -20                 -15

CAT AAC AGA GAA CAG GCC AAC CTC AAC TCA AGG ACA GAA GAG ACT ATA     150
His Asn Arg Glu Gln Ala Asn Leu Asn Ser Arg Thr Glu Glu Thr Ile
        -10                  -5                   1               5

AAA TTT GCT GCA GCA CAT TAT AAT ACA GAG ATC TTG AAA AGT ATT GAT     198
Lys Phe Ala Ala Ala His Tyr Asn Thr Glu Ile Leu Lys Ser Ile Asp
                 10                  15                  20

AAT GAG TGG AGA AAG ACT CAA TGC ATG CCA CGG GAG GTG TGT ATA GAT     246
Asn Glu Trp Arg Lys Thr Gln Cys Met Pro Arg Glu Val Cys Ile Asp
                 25                  30                  35

GTG GGG AAG GAG TTT GGA GTC GCG ACA AAC ACC TTC TTT AAA CCT CCA     294
Val Gly Lys Glu Phe Gly Val Ala Thr Asn Thr Phe Phe Lys Pro Pro
                 40                  45                  50

TGT GTG TCC GTC TAC AGA TGT GGG GGT TGC TGC AAT AGT GAG GGG CTG     342
Cys Val Ser Val Tyr Arg Cys Gly Gly Cys Cys Asn Ser Glu Gly Leu
        55                  60                  65

CAG TGC ATG AAC ACC AGC ACG AGC TAC CTC AGC AAG ACG TTA TTT GAA     390
Gln Cys Met Asn Thr Ser Thr Ser Tyr Leu Ser Lys Thr Leu Phe Glu
70                  75                  80                  85

ATT ACA GTG CCT CTC TCT CAA GGC CCC AAA CCA GTA ACA ATC AGT TTT     438
Ile Thr Val Pro Leu Ser Gln Gly Pro Lys Pro Val Thr Ile Ser Phe
                 90                  95                 100

GCC AAT CAC ACT TCC TGC CGA TGC ATG TCT AAA CTG GAT GTT TAC AGA     486
Ala Asn His Thr Ser Cys Arg Cys Met Ser Lys Leu Asp Val Tyr Arg
```

-continued

```
                105                 110                 115
CAA GTT CAT TCC ATT ATT AGA CGT TCC CTG CCA GCA ACA CTA CCA CAG      534
Gln Val His Ser Ile Ile Arg Arg Ser Leu Pro Ala Thr Leu Pro Gln
        120                 125                 130

TGT CAG GCA GCG AAC AAG ACC TGC CCC ACC AAT TAC ATG TGG AAT AAT      582
Cys Gln Ala Ala Asn Lys Thr Cys Pro Thr Asn Tyr Met Trp Asn Asn
    135                 140                 145

CAC ATC TGC AGA TGC CTG GCT CAG GAA GAT TTT ATG TTT TCC TCG GAT      630
His Ile Cys Arg Cys Leu Ala Gln Glu Asp Phe Met Phe Ser Ser Asp
150                 155                 160                 165

GCT GGA GAT GAC TCA ACA GAT GGA TTC CAT GAC ATC TGT GGA CCA AAC      678
Ala Gly Asp Asp Ser Thr Asp Gly Phe His Asp Ile Cys Gly Pro Asn
                170                 175                 180

AAG GAG CTG GAT GAA GAG ACC TGT CAG TGT GTC TGC AGA GCG GGG CTT      726
Lys Glu Leu Asp Glu Glu Thr Cys Gln Cys Val Cys Arg Ala Gly Leu
            185                 190                 195

CGG CCT GCC AGC TGT GGA CCC CAC AAA GAA CTA GAC AGA AAC TCA TGC      774
Arg Pro Ala Ser Cys Gly Pro His Lys Glu Leu Asp Arg Asn Ser Cys
        200                 205                 210

CAG TGT GTC TGT AAA AAC AAA CTC TTC CCC AGC CAA TGT GGG GCC AAC      822
Gln Cys Val Cys Lys Asn Lys Leu Phe Pro Ser Gln Cys Gly Ala Asn
    215                 220                 225

CGA GAA TTT GAT GAA AAC ACA TGC CAG TGT GTA TGT AAA AGA ACC TGC      870
Arg Glu Phe Asp Glu Asn Thr Cys Gln Cys Val Cys Lys Arg Thr Cys
230                 235                 240                 245

CCC AGA AAT CAA CCC CTA AAT CCT GGA AAA TGT GCC TGT GAA TGT ACA      918
Pro Arg Asn Gln Pro Leu Asn Pro Gly Lys Cys Ala Cys Glu Cys Thr
                250                 255                 260

GAA AGT CCA CAG AAA TGC TTG TTA AAA GGA AAG AAG TTC CAC CAC CAA      966
Glu Ser Pro Gln Lys Cys Leu Leu Lys Gly Lys Lys Phe His His Gln
            265                 270                 275

ACA TGC AGC TGT TAC AGA CGG CCA TGT ACG AAC CGC CAG AAG GCT TGT     1014
Thr Cys Ser Cys Tyr Arg Arg Pro Cys Thr Asn Arg Gln Lys Ala Cys
        280                 285                 290

GAG CCA GGA TTT TCA TAT AGT GAA GAA GTG TGT CGT TGT GTC CCT TCA     1062
Glu Pro Gly Phe Ser Tyr Ser Glu Glu Val Cys Arg Cys Val Pro Ser
    295                 300                 305

TAT TGG AAA AGA CCA CAA ATG AGC TAAGATTGTA CTGTTTTCCA GTTCATCGAT    1116
Tyr Trp Lys Arg Pro Gln Met Ser
310                 315

TTTCTATTAT GGAAAACTGT GTTG                                          1140
```

(2) INFORMATION FOR SEQ ID NO:33:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO:33:

```
Met Thr Val Leu Tyr Pro Glu Tyr Trp Lys Met Tyr Lys Cys Gln Leu
-33             -30                 -25                 -20

Arg Lys Gly Gly Trp Gln His Asn Arg Glu Gln Ala Asn Leu Asn Ser
        -15                 -10                 -5

Arg Thr Glu Glu Thr Ile Lys Phe Ala Ala Ala His Tyr Asn Thr Glu
    1               5                  10                  15

Ile Leu Lys Ser Ile Asp Asn Glu Trp Arg Lys Thr Gln Cys Met Pro
                20                  25                  30
```

```
Arg Glu Val Cys Ile Asp Val Gly Lys Glu Phe Gly Val Ala Thr Asn
            35                  40                  45

Thr Phe Phe Lys Pro Pro Cys Val Ser Val Tyr Arg Cys Gly Gly Cys
            50                  55                  60

Cys Asn Ser Glu Gly Leu Gln Cys Met Asn Thr Ser Thr Ser Tyr Leu
            65                  70                  75

Ser Lys Thr Leu Phe Glu Ile Thr Val Pro Leu Ser Gln Gly Pro Lys
 80                  85                  90                  95

Pro Val Thr Ile Ser Phe Ala Asn His Thr Ser Cys Arg Cys Met Ser
            100                 105                 110

Lys Leu Asp Val Tyr Arg Gln Val His Ser Ile Ile Arg Arg Ser Leu
            115                 120                 125

Pro Ala Thr Leu Pro Gln Cys Gln Ala Ala Asn Lys Thr Cys Pro Thr
            130                 135                 140

Asn Tyr Met Trp Asn Asn His Ile Cys Arg Cys Leu Ala Gln Glu Asp
            145                 150                 155

Phe Met Phe Ser Ser Asp Ala Gly Asp Asp Ser Thr Asp Gly Phe His
160                 165                 170                 175

Asp Ile Cys Gly Pro Asn Lys Glu Leu Asp Glu Glu Thr Cys Gln Cys
            180                 185                 190

Val Cys Arg Ala Gly Leu Arg Pro Ala Ser Cys Gly Pro His Lys Glu
            195                 200                 205

Leu Asp Arg Asn Ser Cys Gln Cys Val Cys Lys Asn Lys Leu Phe Pro
            210                 215                 220

Ser Gln Cys Gly Ala Asn Arg Glu Phe Asp Glu Asn Thr Cys Gln Cys
            225                 230                 235

Val Cys Lys Arg Thr Cys Pro Arg Asn Gln Pro Leu Asn Pro Gly Lys
240                 245                 250                 255

Cys Ala Cys Glu Cys Thr Glu Ser Pro Gln Lys Cys Leu Leu Lys Gly
            260                 265                 270

Lys Lys Phe His His Gln Thr Cys Ser Cys Tyr Arg Arg Pro Cys Thr
            275                 280                 285

Asn Arg Gln Lys Ala Cys Glu Pro Gly Phe Ser Tyr Ser Glu Glu Val
            290                 295                 300

Cys Arg Cys Val Pro Ser Tyr Trp Lys Arg Pro Gln Met Ser
305                 310                 315

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

TGAGTGATTTGTAGCTGCTGTG                                             22

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:35:

TATTGCAGCAACCCCCACATCT                                                  22

(2) INFORMATION FOR SEQ ID NO:36:

(i) SEQUENCE CHARACTERISTICS:
        (A) LENGTH: 196 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:36:

Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ala Glu Asp Ala Leu Glu Thr Ser Leu Arg
50                      55                  60

Ala His Gly Ser His Ala Ile Asn His Val Pro Glu Lys Arg Pro Val
65                  70                  75                  80

Pro Ile Arg Arg Lys Arg Ser Ile Glu Glu Ala Ile Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
            130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Ser Asn Leu Asn Pro Asp His Arg Glu Glu Glu
            180                 185                 190

Thr Asp Val Arg
        195

(2) INFORMATION FOR SEQ ID NO:37:

(i) SEQUENCE CHARACTERISTICS:
        (A) LENGTH: 241 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:37:

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
            35                  40                  45

```
His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala (2) INFORMATION FOR SEQ ID NO:38:

(i) SEQUENCE CHARACTERISTICS:
        (A) LENGTH: 149 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:38:

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140
```

```
Ala Val Pro Arg Arg
145

(2) INFORMATION FOR SEQ ID NO:39:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:39:

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
        50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Arg Arg Pro
130                 135                 140

Lys Gly Arg Gly Lys Arg Arg Glu Lys Gln Arg Pro Thr Asp Cys
145                 150                 155                 160

His Leu Cys Gly Asp Ala Val Pro Arg Arg
                165                 170

(2) INFORMATION FOR SEQ ID NO:40:

(i) SEQUENCE CHARACTERISTICS:
        (A) LENGTH: 147 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:40:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95
```

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Cys Asp Lys
            130                 135             140

Pro Arg Arg
145

(2) INFORMATION FOR SEQ ID NO:41:

(i) SEQUENCE CHARACTERISTICS:
        (A) LENGTH: 191 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:41:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
            130                 135             140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

(2) INFORMATION FOR SEQ ID NO:42:

(i) SEQUENCE CHARACTERISTICS:
        (A) LENGTH: 215 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:42:

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly

-continued

```
                20                  25                  30
Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
            85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
        210                 215
```

(2) INFORMATION FOR SEQ ID NO:43:

(i) SEQUENCE CHARACTERISTICS:
        (A) LENGTH: 232 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:43:

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
            85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
```

```
             145                 150                 155                 160
Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

(2) INFORMATION FOR SEQ ID NO:44:

(i) SEQUENCE CHARACTERISTICS:
  (A) LENGTH: 1997 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 352..1608

(xi) SEQUENCE DESCRIPTION: SEQ ID NO:44:

```
CCCGCCCCGC CTCTCCAAAA AGCTACACCG ACGCGGACCG CGGCGGCGTC CTCCCTCGCC      60

CTCGCTTCAC CTCGCGGGCT CCGAATGCGG GGAGCTCGGA TGTCCGGTTT CCTGTGAGGC     120

TTTTACCTGA CACCCGCCGC CTTTCCCCGG CACTGGCTGG GAGGGCGCCC TGCAAAGTTG     180

GGAACGCGGA GCCCCGGACC CGCTCCCGCC GCCTCCGGCT CGCCCAGGGG GGGTCGCCGG     240

GAGGAGCCCG GGGGAGAGGG ACCAGGAGGG GCCCGCGGCC TCGCAGGGGC GCCCGCGCCC     300

CCACCCCTGC CCCCGCCAGC GGACCGGTCC CCCACCCCCG GTCCTTCCAC C ATG CAC      357
                                                         Met His
                                                           1

TTG CTG GGC TTC TTC TCT GTG GCG TGT TCT CTG CTC GCC GCT GCG CTG      405
Leu Leu Gly Phe Phe Ser Val Ala Cys Ser Leu Leu Ala Ala Ala Leu
        5                   10                  15

CTC CCG GGT CCT CGC GAG GCG CCC GCC GCC GCC GCC GCC TTC GAG TCC      453
Leu Pro Gly Pro Arg Glu Ala Pro Ala Ala Ala Ala Ala Phe Glu Ser
    20                  25                  30

GGA CTC GAC CTC TCG GAC GCG GAG CCC GAC GCG GGC GAG GCC ACG GCT      501
Gly Leu Asp Leu Ser Asp Ala Glu Pro Asp Ala Gly Glu Ala Thr Ala
35                  40                  45                  50

TAT GCA AGC AAA GAT CTG GAG GAG CAG TTA CGG TCT GTG TCC AGT GTA      549
Tyr Ala Ser Lys Asp Leu Glu Glu Gln Leu Arg Ser Val Ser Ser Val
                55                  60                  65

GAT GAA CTC ATG ACT GTA CTC TAC CCA GAA TAT TGG AAA ATG TAC AAG      597
Asp Glu Leu Met Thr Val Leu Tyr Pro Glu Tyr Trp Lys Met Tyr Lys
            70                  75                  80

TGT CAG CTA AGG AAA GGA GGC TGG CAA CAT AAC AGA GAA CAG GCC AAC      645
Cys Gln Leu Arg Lys Gly Gly Trp Gln His Asn Arg Glu Gln Ala Asn
        85                  90                  95

CTC AAC TCA AGG ACA GAA GAG ACT ATA AAA TTT GCT GCA GCA CAT TAT      693
Leu Asn Ser Arg Thr Glu Glu Thr Ile Lys Phe Ala Ala Ala His Tyr
    100                 105                 110

AAT ACA GAG ATC TTG AAA AGT ATT GAT AAT GAG TGG AGA AAG ACT CAA      741
Asn Thr Glu Ile Leu Lys Ser Ile Asp Asn Glu Trp Arg Lys Thr Gln
115                 120                 125                 130
```

```
TGC ATG CCA CGG GAG GTG TGT ATA GAT GTG GGG AAG GAG TTT GGA GTC        789
Cys Met Pro Arg Glu Val Cys Ile Asp Val Gly Lys Glu Phe Gly Val
            135                 140                 145

GCG ACA AAC ACC TTC TTT AAA CCT CCA TGT GTG TCC GTC TAC AGA TGT        837
Ala Thr Asn Thr Phe Phe Lys Pro Pro Cys Val Ser Val Tyr Arg Cys
            150                 155                 160

GGG GGT TGC TGC AAT AGT GAG GGG CTG CAG TGC ATG AAC ACC AGC ACG        885
Gly Gly Cys Cys Asn Ser Glu Gly Leu Gln Cys Met Asn Thr Ser Thr
            165                 170                 175

AGC TAC CTC AGC AAG ACG TTA TTT GAA ATT ACA GTG CCT CTC TCT CAA        933
Ser Tyr Leu Ser Lys Thr Leu Phe Glu Ile Thr Val Pro Leu Ser Gln
        180                 185                 190

GGC CCC AAA CCA GTA ACA ATC AGT TTT GCC AAT CAC ACT TCC TGC CGA        981
Gly Pro Lys Pro Val Thr Ile Ser Phe Ala Asn His Thr Ser Cys Arg
195                 200                 205                 210

TGC ATG TCT AAA CTG GAT GTT TAC AGA CAA GTT CAT TCC ATT ATT AGA       1029
Cys Met Ser Lys Leu Asp Val Tyr Arg Gln Val His Ser Ile Ile Arg
            215                 220                 225

CGT TCC CTG CCA GCA ACA CTA CCA CAG TGT CAG GCA GCG AAC AAG ACC       1077
Arg Ser Leu Pro Ala Thr Leu Pro Gln Cys Gln Ala Ala Asn Lys Thr
            230                 235                 240

TGC CCC ACC AAT TAC ATG TGG AAT AAT CAC ATC TGC AGA TGC CTG GCT       1125
Cys Pro Thr Asn Tyr Met Trp Asn Asn His Ile Cys Arg Cys Leu Ala
            245                 250                 255

CAG GAA GAT TTT ATG TTT TCC TCG GAT GCT GGA GAT GAC TCA ACA GAT       1173
Gln Glu Asp Phe Met Phe Ser Ser Asp Ala Gly Asp Asp Ser Thr Asp
            260                 265                 270

GGA TTC CAT GAC ATC TGT GGA CCA AAC AAG GAG CTG GAT GAA GAG ACC       1221
Gly Phe His Asp Ile Cys Gly Pro Asn Lys Glu Leu Asp Glu Glu Thr
275                 280                 285                 290

TGT CAG TGT GTC TGC AGA GCG GGG CTT CGG CCT GCC AGC TGT GGA CCC       1269
Cys Gln Cys Val Cys Arg Ala Gly Leu Arg Pro Ala Ser Cys Gly Pro
                295                 300                 305

CAC AAA GAA CTA GAC AGA AAC TCA TGC CAG TGT GTC TGT AAA AAC AAA       1317
His Lys Glu Leu Asp Arg Asn Ser Cys Gln Cys Val Cys Lys Asn Lys
            310                 315                 320

CTC TTC CCC AGC CAA TGT GGG GCC AAC CGA GAA TTT GAT GAA AAC ACA       1365
Leu Phe Pro Ser Gln Cys Gly Ala Asn Arg Glu Phe Asp Glu Asn Thr
            325                 330                 335

TGC CAG TGT GTA TGT AAA AGA ACC TGC CCC AGA AAT CAA CCC CTA AAT       1413
Cys Gln Cys Val Cys Lys Arg Thr Cys Pro Arg Asn Gln Pro Leu Asn
            340                 345                 350

CCT GGA AAA TGT GCC TGT GAA TGT ACA GAA AGT CCA CAG AAA TGC TTG       1461
Pro Gly Lys Cys Ala Cys Glu Cys Thr Glu Ser Pro Gln Lys Cys Leu
355                 360                 365                 370

TTA AAA GGA AAG AAG TTC CAC CAC CAA ACA TGC AGC TGT TAC AGA CGG       1509
Leu Lys Gly Lys Lys Phe His His Gln Thr Cys Ser Cys Tyr Arg Arg
                375                 380                 385

CCA TGT ACG AAC CGC CAG AAG GCT TGT GAG CCA GGA TTT TCA TAT AGT       1557
Pro Cys Thr Asn Arg Gln Lys Ala Cys Glu Pro Gly Phe Ser Tyr Ser
            390                 395                 400

GAA GAA GTG TGT CGT TGT GTC CCT TCA TAT TGG AAA AGA CCA CAA ATG       1605
Glu Glu Val Cys Arg Cys Val Pro Ser Tyr Trp Lys Arg Pro Gln Met
            405                 410                 415

AGC TAAGATTGTA CTGTTTTCCA GTTCATCGAT TTTCTATTAT GGAAAACTGT           1658
Ser

GTTGCCACAG TAGAACTGTC TGTGAACAGA GAGACCCTTG TGGGTCCATG CTAACAAAGA    1718

CAAAAGTCTG TCTTTCCTGA ACCATGTGGA TAACTTTACA GAAATGGACT GGAGCTCATC    1778
```

```
TGCAAAAGGC CTCTTGTAAA GACTGGTTTT CTGCCAATGA CCAAACAGCC AAGATTTTCC      1838

TCTTGTGATT TCTTTAAAAG AATGACTATA TAATTTATTT CCACTAAAAA TATTGTTTCT      1898

GCATTCATTT TTATAGCAAC AACAATTGGT AAAACTCACT GTGATCAATA TTTTTATATC      1958

ATGCAAAATA TGTTTAAAAT AAAATGAAAA TTGTATTAT                             1997

(2) INFORMATION FOR SEQ ID NO:45:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:45:

Met His Leu Leu Gly Phe Phe Ser Val Ala Cys Ser Leu Leu Ala Ala
  1               5                  10                  15

Ala Leu Leu Pro Gly Pro Arg Glu Ala Pro Ala Ala Ala Ala Ala Phe
             20                  25                  30

Glu Ser Gly Leu Asp Leu Ser Asp Ala Glu Pro Asp Ala Gly Glu Ala
         35                  40                  45

Thr Ala Tyr Ala Ser Lys Asp Leu Glu Glu Gln Leu Arg Ser Val Ser
 50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
```

```
305                 310                 315                 320
Asn Lys Leu Phe Pro Ser Gln Cys Gly Ala Asn Arg Glu Phe Asp Glu
                325                 330                 335
Asn Thr Cys Gln Cys Val Cys Lys Arg Thr Cys Pro Arg Asn Gln Pro
            340                 345                 350
Leu Asn Pro Gly Lys Cys Ala Cys Glu Cys Thr Glu Ser Pro Gln Lys
            355                 360             365
Cys Leu Leu Lys Gly Lys Lys Phe His His Gln Thr Cys Ser Cys Tyr
        370                 375             380
Arg Arg Pro Cys Thr Asn Arg Gln Lys Ala Cys Glu Pro Gly Phe Ser
385                 390                 395                 400
Tyr Ser Glu Glu Val Cys Arg Cys Val Pro Ser Tyr Trp Lys Arg Pro
                405                 410                 415
Gln Met Ser
```

RECEPTOR LIGAND

This is a continuation-in-part of U.S. patent application Ser. No. 08/510,133, filed Aug. 1, 1995.

FIELD OF THE INVENTION

The present invention generally relates to the field of genetic engineering and more particularly to growth factors for endothelial cells and growth factor genes.

BACKGROUND OF THE INVENTION

Developmental growth, the remodelling and regeneration of adult tissues, as well as solid tumor growth, can only occur when accompanied by blood vessel formation. Angioblasts and hematopoietic precursor cells differentiate from the mesoderm and form the blood islands of the yolk sac and the primary vascular system of the embryo. The development of blood vessels from these early (in situ) differentiating endothelial cells is termed vasculogenesis. Major embryonic blood vessels are believed to arise via vasculogenesis, whereas the formation of the rest of the vascular tree is thought to occur as a result of vascular sprouting from pre-existing vessels, a process called angiogenesis, Risau, et al., *Devel. Biol.*, 125:441–450 (1988).

Endothelial cells give rise to several types of functionally and morphologically distinct vessels. When organs differentiate and begin to perform their specific functions, the phenotypic heterogeneity of endothelial cells increases. Upon angiogenic stimulation, endothelial cells may re-enter the cell cycle, migrate, withdraw from the cell cycle and subsequently differentiate again to form new vessels that are functionally adapted to their tissue environment. Endothelial cells undergoing angiogenesis degrade the underlying basement membrane and migrate, forming capillary sprouts that project into the perivascular stroma. Ausprunk, et al., *Microvasc. Rev.*, 14:51–65 (1977). Angiogenesis during tissue development and regeneration depends on the tightly controlled processes of endothelial cell proliferation, migration, differentiation, and survival. Dysfunction of the endothelial cell regulatory system is a key feature of many diseases. Most significantly, tumor growth and metastasis have been shown to be angiogenesis dependent. Folkman, et al., *J. Biol. Chem.*, 267: 10931–10934 (1992).

Key signals regulating cell growth and differentiation are mediated by polypeptide growth factors and their transmembrane receptors, many of which are tyrosine kinases. Autophosphorylated peptides within the tyrosine kinase insert and carboxyl-terminal sequences of activated receptors are commonly recognized by kinase substrates involved in signal transduction for the readjustment of gene expression in responding cells. Several families of receptor tyrosine kinases have been characterized. Van der Geer, et al., *Ann. Rev. Cell Biol.*, 10:251–337 (1994). The major growth factors and receptors transducing angiogenic stimuli are schematically shown in FIG. 1.

Fibroblast growth factors are also known to be involved in the regulation of angiogenesis. They have been shown to be mitogenic and chemotactic for cultured endothelial cells. Fibroblast growth factors also stimulate the production of proteases, such as collagenases and plasminogen activators, and induce tube formation by endothelial cells. Saksela, et al., *Ann. Rev. Cell Biol.*, 4:93–126 (1988). There are two general classes of fibroblast growth factors, FGF-1 and FGF-2, both of which lack conventional signal peptides. Both types have an affinity for heparin and FGF-2 is bound to heparin sulfate proteoglycans in the subendothelial extracellular matrix from which it may be released after injury. Heparin potentiates the stimulation of endothelial cell proliferation by angiogenic FGFs, both by protecting against denaturation and degradation and dimerizing the FGFs. Cultured endothelial cells express the FGF-1 receptor but no significant levels of other high-affinity fibroblast growth factor receptors.

Among other ligands for receptor tyrosine kinases, the platelet derived growth factor, PDGF-BB, has been shown to be weakly angiogenic in the chick chorioallantoic membrane. Risau, et al., *Growth Factors*, 7:261–266 (1992). Transforming growth factor α (TGFα) is an angiogenic factor secreted by several tumor cell types and by macrophages. Hepatocyte growth factor (HGF), the ligand of the c-met proto-oncogene-encoded receptor, also is strongly angiogenic.

Recent evidence shows that there are endothelial cell specific growth factors and receptors that may be primarily responsible for the stimulation of endothelial cell growth, differentiation and certain differentiated functions. The best studied of these is vascular endothelial growth factor (VEGF), a member of the PDGF family. Vascular endothelial growth factor is a dimeric glycoprotein of disulfide-linked 23 kDa subunits. Other reported effects of VEGF include the mobilization of intracellular calcium, the induction of plasminogen activator and plasminogen activator inhibitor-1 synthesis, stimulation of hexose transport in endothelial cells, and promotion of monocyte migration in vitro. Four VEGF isoforms, encoded by distinct mRNA splice variants, appear to be equally capable of stimulating mitogenesis in endothelial cells. However, each isoform has a different affinity for cell surface proteoglycans, which behave as low affinity receptors for VEGF. The 121 and 165 amino acid isoforms of VEGF are secreted in a soluble form, whereas the isoforms of 189 and 206 amino acid residues remain cell surface associated and have a strong affinity for heparin.

VEGF was originally purified from several sources on the basis of its mitogenic activity toward endothelial cells, and also by its ability to induce microvascular permeability, hence it is also called vascular permeability factor (VPF). VEGF produces signals through two receptor tyrosine kinases, VEGFR-1 (FLT-1) and VEGFR-2 (KDR/Flk-1), which are expressed specifically on endothelial cells. The VEGF-related placenta growth factor (PlGF) was recently shown to bind to VEGFR-1 with high affinity. PlGF was able to enhance the growth factor activity of VEGF, but it did not stimulate endothelial cells on its own. Naturally occurring VEGF/PlGF heterodimers were nearly as potent mitogens as VEGF homodimers for endothelial cells.

The pattern of VEGF expression suggests its involvement in the development and maintenance of the normal vascular system and in tumor angiogenesis. During murine development, the entire 7.5 day post-coital (p.c.) endoderm expresses VEGF and the ventricular neuroectoderm produces VEGF at the capillary ingrowth stage. See Breier, et al., *Development*, 114:521–523 (1992). On day two of quail development, the vascularized area of the yolk sac as well as the whole embryo show expression of VEGF. In addition, epithelial cells next to fenestrated endothelia in adult mice show persistent VEGF expression, suggesting a role in the maintenance of this specific endothelial phenotype and function.

Two high affinity receptors for VEGF have been characterized. These are VEGFR-1/Flt-1 (fms-like tyrosine kinase- 1) and VEGFR-2/Kdr/Flk-1 (kinase insert domain containing receptor/fetal liver kinase-1). Those receptors are classified in the PDGF-receptor family, but they have seven rather than five immunoglobulin-like loops in their extracellular domain and they possess a longer kinase insert than normally observed in this family. The expression of VEGF receptors occurs mainly in vascular endothelial cells, although some may be present on monocytes and melanoma cells. Only endothelial cells have been reported to proliferate in response to VEGF, and endothelial cells from different sources show different responses. Thus, the signals mediated through VEGFR-1 and VEGFR-2 appear to be cell type specific.

The Flt4 receptor tyrosine kinase (VEGFR-3) is closely related in structure to the products of the VEGFR-1 and VEGFR-2 genes. Despite this similarity, the mature form of Flt4 differs from the VEGF receptors in that it is proteolytically cleaved in the extracellular domain into two disulfide-linked polypeptides. Pajusola et al., *Cancer Res.*, 52:5738–5743 (1992). The 4.5 and 5.8 kb Flt4 mRNAs encode polypeptides which differ in their C-termini due to the use of alternative 3' exons. The VEGFs do not show specific binding to Flt4 or induce its autophosphorylation.

Expression of Flt4 appears to be more restricted than expression of VEGFR-1 or VEGFR-2. The expression of Flt4 first becomes detectable by in situ hybridization in the angioblasts of head mesenchyme, the cardinal vein, and extraembryonically in the allantois of 8.5 day p.c. mouse embryos. In 12.5 day p.c. embryos the Flt4 signal is observed in developing venous and presumptive lymphatic endothelia, but arterial endothelia appear negative. During later stages of development, Flt4 mRNA becomes restricted to developing lymphatic vessels. Only the lymphatic endothelia and some high endothelial venules express Flt4 mRNA in adult human tissues and increased expression occurs in lymphatic sinuses in metastatic lymph nodes and in lymphangioma. These results support the theory of the venous origin of lymphatic vessels.

Five endothelial cell specific receptor tyrosine kinases, Flt-1 (VEGFR-1), KDR/Flk-1 (VEGFR-2), Flt4, Tie and Tek/Tie-2 have so far been described, which possess the intrinsic tyrosine kinase activity essential for signal transduction. Targeted mutations inactivating Flt-1, Flk-1, Tie and Tek in mouse embryos have indicated their essential and specific roles in vasculogenesis and angiogenesis at the molecular level. VEGFR-1 and VEGFR-2 bind VEGF with high affinity (Kd 16 pM and 760 pM, respectively) and VEGFR-1 also binds the related placenta growth factor (PlGF; Kd about 200 pM), while the ligands for Tie, Tek, and Flt4 have not yet been reported.

SUMMARY OF THE INVENTION

The present invention provides a ligand for the Flt4 receptor tyrosine kinase. Thus, the invention provides a purified and isolated polypeptide which specifically binds to the Flt4 receptor tyrosine kinase. In a preferred embodiment, the ligand comprises a fragment of the amino acid sequence shown in SEQ ID NO: 33 which specifically binds to the Flt4 receptor tyrosine kinase.

The present invention also provides a precursor of an Flt4 ligand, wherein the precursor comprises the amino acid sequence shown in SEQ ID NO: 33. Thus, the invention includes a purified and isolated polypeptide having the amino acid sequence shown in SEQ ID NO: 33.

A putative 33 amino acid signal peptide has been identified in the amino acid sequence shown in SEQ ID NO: 33. Thus, in a related aspect, the invention includes a purified and isolated polypeptide comprising amino acids 1–317 of SEQ ID NO: 33. The Flt4 ligand precursor is proteolytically cleaved upon expression to produce an approximately 23 kD peptide which is the Flt4 ligand (herein designated VEGF-C). Thus, the invention includes a polypeptide having an amino acid sequence comprising a portion of SEQ ID NO:33, the portion encoding a fragment capable of specifically binding to Flt4. A preferred fragment has a molecular weight of about 23 kDa as assessed by SDS-PAGE under reducing conditions. In a preferred embodiment of the invention, an Flt4 ligand is provided which is the cleavage product of the precursor peptide shown in SEQ ID NO: 33 and which has a molecular weight of approximately 23 kD under reducing conditions.

Evidence suggests that the amino acids essential for retaining Flt4 ligand activity are contained within approximately amino acids 1–120 of SEQ ID NO: 33, and that the proteolytic cleavage to produce a mature, naturally-occurring Flt4 ligand occurs within approximately amino acids 1–180 of SEQ ID NO: 33. Accordingly, preferred polypeptides of the invention include polypeptides comprising amino acids 1–120, 1–121, 1–122, 1–123, 1–124 . . . 1–178, 1–179, and 1–180 of SEQ ID NO: 33, wherein said polypeptides specifically bind to an Flt4 receptor tyrosine kinase. A preferred Flt4 ligand comprises approximately amino acids 1–120 of SEQ ID NO: 33. Another preferred polypeptide of the invention comprises approximately amino acids 1–180 of SEQ ID NO: 33.

The present invention also provides a cDNA encoding a novel polypeptide, designated VEGF-C, that is structurally homologous to VEGF. VEGF-C is a ligand for the FLT4 receptor tyrosine kinase (VEGFR-3), a receptor tyrosine kinase related to VEGFR-1 and VEGFR-2 that does not bind VEGF. VEGFR-3 is expressed in venous and lymphatic endothelia of fetal tissues and predominantly in lymphatic endothelial of adult tissues. Kaipainen et al., *Cancer Res.*, 54:6571–77 (1994); Kaipainen et al., *Proc. Natl. Acad. Sci. USA*, 92:3566–70 (1995).

Thus, in a preferred embodiment, the invention includes a purified and isolated nucleic acid (e.g., a DNA or an RNA) encoding an Flt4 ligand precursor. Due to the degeneracy of the genetic code, numerous such coding sequences are possible, each having in common the coding of the amino acid sequence shown in SEQ ID NO: 33. As set forth above, the invention includes polypeptides which comprise a portion of the amino acid sequence shown in SEQ ID NO: 33 and which bind the Flt4 receptor tyrosine kinase (herein designated VEGFR-3); the invention also is intended to include nucleic acids encoding these polypeptides. Ligand precursors according to the invention, when expressed in an appropriate host cell, produce, via cleavage, a peptide which binds specifically to the Flt4 receptor tyrosine kinase (VEGFR-3). The nucleotide sequence shown in SEQ ID NO:32 contains a preferred nucleotide sequence encoding the Flt4 ligand (VEGF-C).

The present invention also provides a cell line which produces an Flt4 ligand. The ligand may be purified and isolated directly from the cell culture medium. Also provided are vectors comprising a DNA encoding the Flt4 ligand, and host cells comprising the vectors. Preferred vectors of the invention are capable of expressing the Flt4 ligand under the control of appropriate promoters and other control sequences. A preferred vector of the invention is plasmid pFLT4-L, having ATCC accession no. 97231.

The invention further includes a method of making polypeptides of the invention. In a preferred method, a nucleic acid or vector of the invention is expressed in a host cell, and a polypeptide of the invention is purified from the host cell or the host cell growth medium.

In another aspect, the invention includes an antibody which is specifically reactive with polypeptides of the invention. Antibodies, both monoclonal and polyclonal, may be made against a ligand of the invention according to standard techniques in the art. Such antibodies may be used in diagnostic applications to monitor angiogenesis, vascularization, lymphatic vessels and their disease states, wound healing, or certain hematopoietic or leukemia cells, or they may be used to block or activate the Flt4 receptor.

Ligands according to the invention may be labeled with a detectable label and used to identify their corresponding receptors in situ. Labeled Flt4 ligand and anti-Flt4 ligand antibodies may be used as imaging agents in the detection of lymphatic vessels, high endothelial venules, and Flt4 receptors expressed in histochemical tissue sections. The ligand or antibody may be covalently or non-covalently coupled to a suitable supermagnetic, paramagnetic, electron dense, echogenic, or radioactive agent for imaging. Other, non-radioactive labels, such as biotin and avidin, may also be used.

The present invention also provides diagnostic and clinical applications for claimed ligands. In a preferred embodiment, Flt4 ligands or precursors are used to accelerate angiogenesis, e.g., during wound healing, or to promote the endothelial functions of lymphatic vessels. Ligands may be applied in any suitable manner using an appropriate pharmaceutically-acceptable vehicle. Ligands also may be used to quantify future metastatic risk by assaying biopsy material for the presence of active receptors or ligands in a binding assay or kit using detectably-labeled ligand. An Flt4 ligand according to the invention also may be used to promote re-growth or permeability of lymphatic vessels in, for example, organ transplant patients. Ligands according to the invention also may be used to treat or prevent inflammation, edema, aplasia of the lymphatic vessels, lymphatic obstruction, elephantiasis, and Milroy's disease. Finally, Flt4 ligands may be used to stimulate lymphocyte production and maturation, and to promote or inhibit trafficking of leukocytes between tissues and lymphatic vessels or to affect migration in and out of the thymus.

Inhibitors of the Flt4 ligand may be used to control endothelial cell proliferation and lymphangiomas. For example, such inhibitors may be used to arrest metastatic growth or spread, or to control other aspects of endothelial cell expression and growth. Inhibitors include antibodies, antisense oligonucleotides, and peptides which block the Flt4 receptor, all of which are intended as aspects of the invention.

BRIEF DESCRIPTION OF THE DRAWING

FIGS. 9B–D show the nucleotide and deduced amino acid sequence of the coding portion of Flt4 ligand cDNA. The cleavage site for the putative signal pepetide is indicated with a shaded triangle.

FIGS. 10A–D show a comparison of the deduced amino acid sequences of PDGF-A (SEQ ID NO: 36); PDGF-B (SEQ ID NO: 37); two PlGF isoforms (SEQ ID NOs: 38 and 39); four VEGF isoforms (SEQ ID NOs: 40–43); and Flt4 ligand (VEGF-C) (SEQ ID NO: 33).

DETAILED DESCRIPTION OF THE INVENTION

Figure 1:
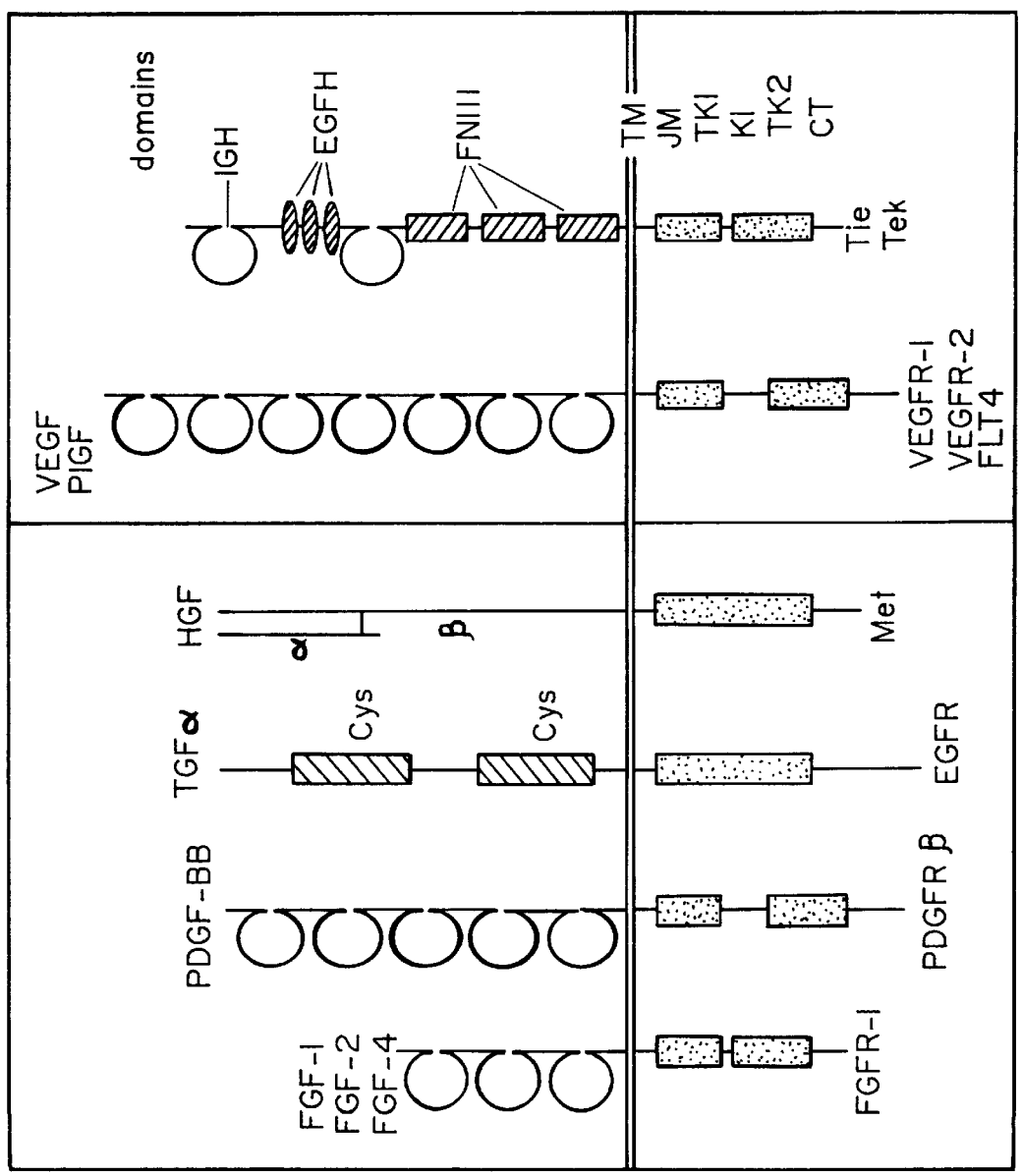
FIG. 1 is a schematic diagram showing major endothelial cell receptor tyrosine kinases and growth factors involved in vasculogenesis and angiogenesis.

Described herein is the isolation of a novel vascular endothelial growth factor and the cloning of a DNA encoding this growth factor from a cDNA library prepared from the human prostatic adenocarcinoma cell line PC-3. The isolated cDNA encodes a protein which is proteolytically processed and secreted to cell culture medium. The secreted protein, designated VEGF-C, binds to the extracellular domain of Flt4 (designated VEGFR-3) and induces tyrosine autophosphorylation of Flt4 and VEGFR-2. VEGF-C also stimulates the migration of endothelial cells in collagen gel.

The present invention also is directed to novel growth factors which are ligands for the Flt4 receptor tyrosine kinase (VEGFR-3). Ligands of the invention are members of a family of platelet-derived growth factors/vascular endothelial growth factors which promote mitosis and proliferation of vascular endothelial cells and/or mesodermal cells. Ligands recognizing the Flt4 receptor tyrosine kinase were purified from a PC-3 prostatic adenocarcinoma cell line (ATCC CRL1435). When applied to a population of cells expressing the Flt4 receptor, ligands of the invention stimulate autophosphorylation, resulting in receptor activation. The invention also provides inhibitors of the Flt4 receptor, including antibodies directed against the ligand. A ligand according to the invention may be coexpressed as a larger precursor which is cleaved to produce the ligand. A coexpressed region in some cases results from alternative splicing of RNA of the ligand gene. Such a co-expressed region may be a function of the particular expression system used to obtain the ligand. The skilled artisan understands that in recombinant production of proteins, additional sequence may be expressed along with a functional peptide depending upon the particular recombinant construct used to express the protein, and subsequently removed to obtain the desired ligand. In some cases the recombinant ligand can be made lacking certain residues of the endogenous/natural ligand. Moreover, it is well-known in that conservative replacements may be made in a protein which do not alter the function of the protein. Accordingly, it is anticipated that such alterations are within the scope of the claims. It is intended that the precursor sequence shown in SEQ ID NO: 33 is capable of stimulating the Flt4 ligand without any further processing in a manner similar to that in which VEGF stimulates its receptor in its unprocessed form.

Results reported herein show that VEGFR-3 transmits signals for a novel growth factor. This conclusion is based on the specific binding of VEGF-C to recombinant Flt4EC (Flt4 extracellular domain) protein and the induction of VEGFR-3 autophosphorylation by medium from VEGF-C transfected cells. In contrast, VEGF and PlGF did not show specific binding to VEGFR-3 or induce its autophosphorylation.

A major part of the difference in the observed molecular mass of the purified and recombinant VEGF-C and the deduced molecular mass of the VEGF-C encoded by the VEGF-C open reading frame (ORF) may be due to proteolytic removal of sequences in the carboxyl terminal region of the latter. Proteolytic processing of the VEGF-C precursor may occur at more than one cleavage site because the 32 kD molecular mass of the recombinant secreted ligand was also less than the deduced molecular mass of VEGF-C ORF without the signal peptide. By extrapolation from studies of the structure of PDGF (Heldin, et al., *Growth Factors*, 8:245–52 (1993)), one can speculate that the region critical for receptor binding and activation by VEGF-C is contained within the amino-terminal first 180 or so amino acid residues of the secreted of VEGF-C protein lacking the signal sequence. In fact, the region critical for receptor binding and activation by VEGF-C is believed to be contained within the first approximately 120 amino acid residues of the secreted VEGF-C protein lacking the signal sequence. Thus, the 23 kD polypeptide binding VEGFR-3 is likely to represent the VEGF-homologous domain. After biosynthesis, the nascent VEGF-C polypeptide may be glycosylated at three putative N-linked glycosylation sites identified in the deduced VEGF-C amino acid sequence.

The carboxyl terminal amino acid sequences, which increase the length of the VEGF-C polypeptide in comparison with other ligands of this family, show a pattern of spacing of cysteine residues reminiscent of the Balbiani ring 3 protein (BR3P) sequence (Dignam and Case, *Gene*, 88:133–40 (1990); Paulsson, et al., *J. Mol. Biol.*, 211:331–49 (1990)). This novel C-terminal silk protein-like structural motif of VEGF-C may fold into an independent domain, which, on the basis of the considerations above, is at least partially cleaved off after biosynthesis. Interestingly, at least one cysteine motif of the BR3P type is also found in the carboxyl terminus of VEGF. In our experiments both the putative precursor and cleaved ligand were detected in the cell culture media, although processing was apparently cell-associated on the basis of the pulse-chase experiments. The determination of the amino terminal sequence of the isolated carboxyl terminal fragment will allow the identification of the proteolytic processing site. The generation of antibodies against different parts of the VEGF-C molecule will allow the exact determination of the precursor-product relationship and ratio, their cellular distribution, and the kinetics of processing and secretion.

VEGF-C has a conserved pattern of eight cysteine residues, which may participate in the formation of intra- and interchain disulfide bonds, creating an antiparallel dimeric biologically active molecule, similar to PDGF. Mutational analysis of the cysteine residues involved in the interchain disulfide bridges has shown that, in contrast to PDGF, VEGF dimers need to be held together by these covalent interactions in order to maintain biological activity. Disulfide linking of the VEGF-C polypeptide chain was evident in the analysis of VEGF-C in nonreducing conditions.

VEGFR-3, which thus distinguishes between VEGF and VEGF-C, is closely related in structure to VEGFR-1 and VEGFR-2. Finnerty, et al., *Oncogene*, 8:2293–98 (1993); Galland, et al., *Oncogene*, 8:1233–40 (1993); Pajusola, et al., *Cancer Res.*, 52:5738–43 (1992). However, the mature form of VEGFR-3 differs from the two other VEGFRs in that is is proteolytically cleaved in the extracellular domain into two disulfide-linked polypeptides. Pajusola, et al., *Oncogene*, 9:3545–55 (1994). Another difference is that the 4.5 and 5.8 kb VEGFR-3 mRNAs encode polypeptides differing in their C-termini and apparently in their signalling properties due to the use of alternative 3' exons. Borg et al., *Oncogene*, 10:973–84 (1995); Pajusola et al., *Oncogene*, 8:2931–37 (1993).

Besides VEGFR-3, VEGFR-2 tyrosine kinase also is activated in response to VEGF-C. VEGFR-2 mediated signals cause striking changes in the morphology, actin reorganization and membrane ruffling of porcine aortic endothelial cells overexpressing this receptor. In these cells, VEGFR-2 also mediated ligand-induced chemotaxis and mitogenicity. Waltenberger et al., *J. Biol. Chem*, 269:26988–95 (1994). Similarly, the receptor chimera CSF-1R/VEGFR-3 was mitogenic when ectopically expressed in NIH3T3 fibroblastic cells, but not in porcine aortic endothelial cells (Pajusola et al., 1994). Consistent with such results, the bovine capillary endothelial cells (BCE), which express VEGFR-2 mRNA but very little or no VEGFR-1 or VEGFR-3 mRNAs, showed enhanced migration when stimulated with VEGF-C. As shown here, light microscopy of the BCE cell cultures in collagen gel also suggested that VEGF-C stimulated the proliferation of these cells. The already existing data thus indicate that the VEGF ligands and receptors show a great specificity in their signalling, which may be cell type dependent.

The expression pattern of the VEGFR-3 (Kaipainen et al., *Proc. Natl. Acad. Sci. USA*, 92:3566–70 (1995)) suggests that VEGF-C may function in the formation of the venous and lymphatic vascular systems during embryogenesis. Constitutive expression of VEGF-C in adult tissues shown herein further suggests that this gene product also is involved in the maintenance of the differentiated functions of the lymphatic endothelium where VEGFR-3 is expressed (Kaipainen et al., 1995). Lymphatic capillaries do not have well formed basal laminae and an interesting possibility remains that the silk-like BR3P motif is involved in producing a supramolecular structure which could regulate the availability of VEGF-C in tissues. However, as shown here, VEGF-C also activates VEGFR-2, which is abundant in proliferating endothelial cells of vascular sprouts and branching vessels of embryonic tissues, but decreased in adult tissues. Millauer et al., *Nature,* 367:576–78 (1993). These data have suggested that VEGFR-2 is a major regulator of vasculogenesis and angiogenesis. VEGF-C may thus have a unique effect in lymphatic endothelium and a more redundant function shared with VEGF in angiogenesis and possibly permeability regulation of several types of endothelia. Because VEGF-C stimulates VEGFR-2 and promotes endothelial migration, a utility for VEGF-C is suggested as an inducer of angiogenesis of blood and lymphatic vessels in wound healing, tissue transplantation, in eye diseases, in the formation of collateral vessels around arterial stenoses and into injured tissues after infarction.

Taken together, these results show an increased complexity of signalling in the vascular endothelium. They reinforce the concept that when organs differentiate and begin to perform their specific functions, the phenotypic heterogeneity of endothelial cells increases in several types of functionally and morphologically distinct vessels. However, upon suitable angiogenic stimuli, endothelial cells can re-enter the cell cycle, migrate, withdraw from the cell cycle and subsequently differentiate again to form new vessels that are functionally adapted to their tissue environment. This process of angiogenesis concurrent with tissue development and regeneration depends on the tightly controlled balance between positive and negative signals for endothelial cell proliferation, migration, differentiation and survival. Previously-identified growth factors promoting angiogenesis include the fibroblast growth factors, hepatocyte growth factor/scatter factor, PDGF and TGF-α. (See, e.g., Folkman, *Nature Med.* 1:27–31 (1995); Friesel and Maciag, *FASEB J.* 9:919–25 (1995); Mustonen and Alitalo, *J. Cell Biol.,* 129:895–98 (1995). However, VEGF has been the only growth factor relatively specific for endothelial cells. The newly identified factors VEGF-B and VEGF-C thus increase our understanding of the complexity of the specific and redundant positive signals for endothelial cells involved in vasculogenesis, angiogenesis, permeability and perhaps also other endothelial functions.

Also described herein is the localization of the VEGF-C gene in human chromosomes by analysis of somatic cell hybrids and fluorescence in situ hybridization (FISH). Southern blotting and polymerase chain reaction analysis of somatic cell hybrids and fluorescence in situ hybridization of metaphase chromosomes was used to assess the chromosomal localization of the VEGF-C gene. The VEGF-C gene was located on chromosome 4q34, close to the human aspartylglucosaminidase gene previously mapped to 4q34–35. The VEGF-C locus in 4q34 is a candidate target for mutations leading to vascular malformations or cardiovascular diseases. Expression studies by Northern blotting and hybridization show abundant VEGF-C expression in heart and skeletal muscle; other tissues, such as lung and kidney, also express this gene. Whereas PlGF is predominantly expressed in the placenta, the expression patterns of the three VEGFs overlap in many tissues, which suggests that they may form heterodimers and interact to exert their physiological functions.

Targeted mutagenesis leading to inactivation of the VEGF receptor loci in the mouse genome has shown that VEGFR-1 is necessary for the proper organization of endothelial cells forming the vascular endothelium, while VEGFR-2 is necessary for the generation of both endothelial and hematopoietic cells. This suggests that the four genes of the VEGF family can be targets for mutations leading to vascular malformations or cardiovascular diseases.

The following Examples illustrate preferred embodiments of the invention, wherein the isolation, characterization, and function of Flt4 ligands and ligand-encoding nucleic acids according to the invention are shown.

EXAMPLE 1

Production of pLTRFlt41 Expression Vector

Figure 2A:
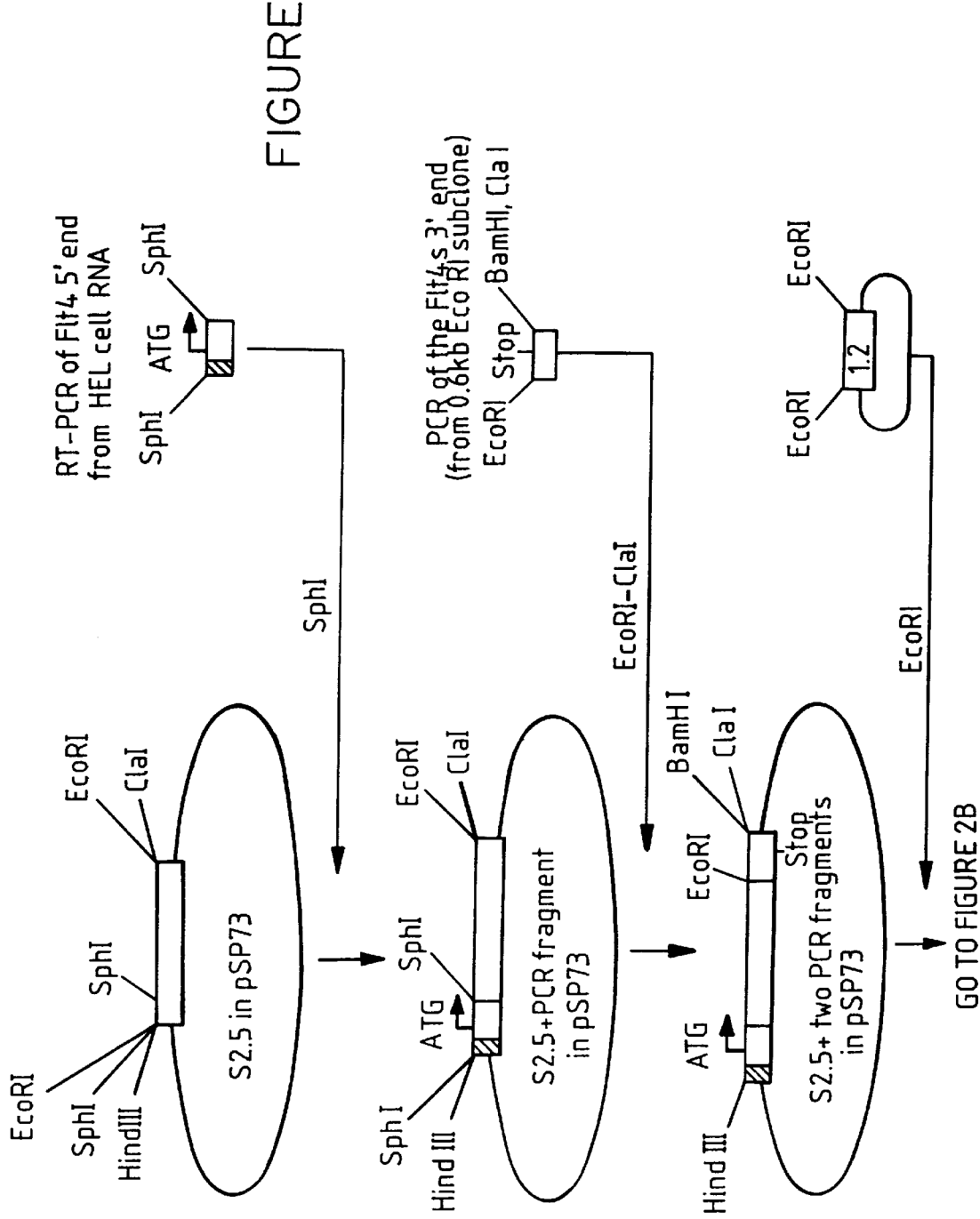
FIGS. 2A and 2B schematically depict the construction of the pLTRFlt4l expression vector.
Figure 2B:
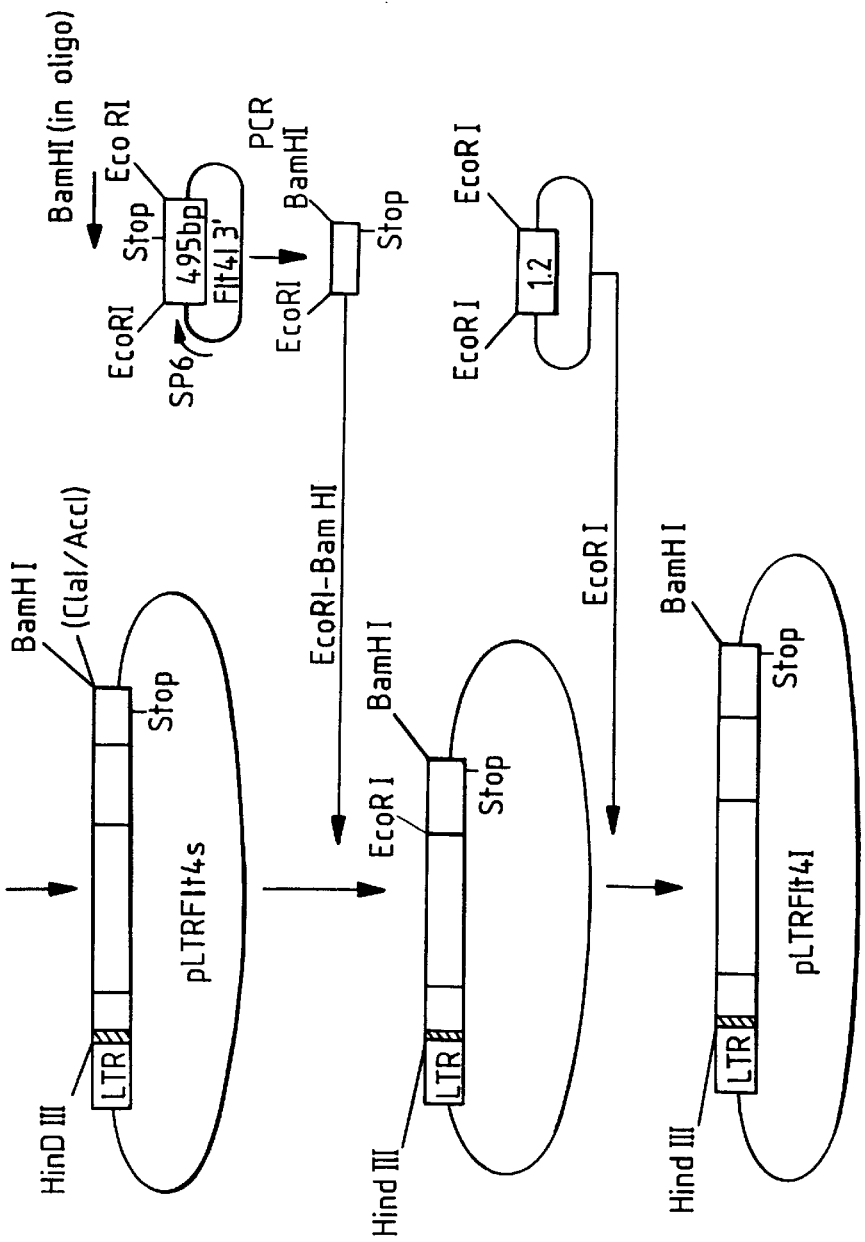

Construction of the LTR-Flt41 vector is schematically shown in FIGS. 2A and 2B. The full-length Flt4s cDNA (Genbank Accession No. X68203) was assembled by first subcloning the S2.5 fragment, reported in Pajusola et al., *Cancer Res.* 52:5738–5743 (1992), incorporated by reference herein, containing base pairs 56–2534 of the Flt4s into the EcoRI site of the pSP73 vector (Promega, Madison, Wis.).

Since cDNA libraries used for screening of Flt4 cDNAs did not contain its most 5' protein-coding sequences, inverse PCR was used for the amplification of the 5' end of Flt4 corresponding to the first 12 amino acid residues (MQRGAALCLRLW). Poly(A)$^+$ RNA was isolated from HEL cells and double-stranded cDNA copy was synthesized using the Amersham cDNA Synthesis System Plus kit and a gene specific primer: 5'-TGTCCTCGCTGTCCTTGTCT-3' (SEQ ID NO: 1), which was located 195 bp downstream of the 5' end of clone S2.5. Double stranded cDNA was treated with T4 DNA polymerase to blunt the ends and cDNA was purified with Centricon 100 filters (Amicon Inc., Beverly, Mass.). Circularization was made in a total volume of 150 ul. The reaction mixture contained ligation buffer, 5% PEG-8000, 1 mM DTT and 8U of T4 DNA ligase (New England Biolabs). Ligation was carried out at 16° C. for 16 hours. Fifteen μl of this reaction mix was used in a standard 100 ul PCR reaction containing 100 ng of specific primers including SacI and PstI restriction sites, present in this segment of the Flt4 cDNA, and 1 unit of Taq DNA polymerase (Perkin Elmer Cetus). Two rounds of PCR were performed using 33 cycles (denaturation at 95° C. for 1 minute, annealing at 55° C. for 2 minutes and elongation at 72° C. for 4 minutes). The PCR mixture was treated sequentially with the SacI and PstI restriction enzymes and after purification with MagicPCR Preps (Promega) DNA fragments were subcloned into the pGEM3Zf(+) vector for sequencing. The sequence obtained corresponds to the 5' end of the Flt4s cDNA clone deposited in the Genbank Database as Accession No. X68203.

The sequence encoding the first 12 amino acid residues was added to the expression construct by ligating an SphI digested PCR fragment amplified using reverse transcription-PCR of poly(A)$^+$ RNA isolated from the HEL cells using the oligonucleotides 5'-ACAT<u>GCATGC</u> CAC-CATGCAG CGGGGCGCCG CGCTGTGCCT GCGACT-GTGG CTCTGCCTGG GACTCCTGGA-3' (SEQ ID NO: 2)(forward primer, SphI site underlined, the translational start codon marked in bold follows an optimized Kozak consensus sequence Kozak, *Nucl. Acids Res.* 15: 8125–8148, 1987) and 5'-ACAT<u>GCATGC</u> CCCGCCGGT CATCC-3' (SEQ ID NO: 3) (reverse primer, SphI site underlined) to the 5' end of the S2.5 fragment, thus replacing unique SphI fragment of the S2.5 plasmid. The resulting vector was digested with EcoRI and ClaI and ligated to a 138 bp PCR fragment amplified from the 0.6 kb EcoRI fragment (base pairs 3789 to 4416 in the Genbank X68203 sequence) which encodes the 3' end of Flt4s shown in FIG. 1 of Pajusola et al., Cancer Res. 52:5738–5743, 1992, using the oligonucleotides 5'-CG<u>GAATTC</u>CC CATGACCCCA AC-3' (SEQ ID NO: 4) (forward, EcoRI site underlined) and 5'-CC <u>ATCGAT</u>GG ATCCTACCTG AAGCCGCTTT CTT-3' (SEQ ID NO: 5) (reverse, ClaI site underlined). The coding domain was completed by ligation of the 1.2 kb EcoRI fragment (base pairs 2535–3789 of sequence X68203) into the above construct. The complete cDNA was subcloned as a HindIII-ClaI(blunted) fragment (this ClaI site was also included in the 3' primer used to construct the 3' end of the coding sequence) to the pLTRpoly expression vector reported in Mäkelä et al., Gene, 118: 293–294 (1992) (Genbank accession number X60280), incorporated by reference herein, using its HindIII-Acc I(blunted) restriction sites.

The long form of Flt4 was produced by replacing the 3'-end of the short form as follows: The 3' region of the Flt4l cDNA was PCR-amplified using a gene specific and a pGEM 3Z vector specific (SP6 promoter) oligonucleotide 5'-ATTTAGGTGACACTATA-3' (SEQ ID NO: 6) as reverse and forward primers, respectively, and an Flt4l cDNA clone containing a 495 bp EcoRI fragment extending downstream of the EcoRI site at nucleotide 3789 of the Genbank X68203 sequence (the sequence downstream of this EcoRI site is deposited as the Flt4 long form 3' sequence having Genbank accession number S66407). The gene specific oligonucleotide contained a BamHI restriction site located right after the end of the coding region. The sequence of that (reverse primer) oligonucleotide was 5'-CCATCGAT <u>GGATCCC</u>GATGCTGCTTAGTAGCTGT-3' (SEQ ID NO: 7) (BamHI site is underlined). The PCR product was digested with EcoRI and BamHI and transferred in frame to LTRFlt4s vector fragment from which the coding sequences downstream of the EcoRI site at base pair 2535 (see sequence X68203) had been removed by EcoRI-BamHI digestion. Again, the coding domain was completed by ligation of the 1.2 kb EcoRI fragment (base pairs 2535–3789 of sequence X68203) back into the resulting construct.

EXAMPLE 2

Production and Analysis of Flt4l Transfected Cells

NIH3T3 cells (60% confluent) were co-transfected with 5 μg of the pLTRFlt4l construct and 0.25 μg of the pSV2neo vector (ATCC) containing the neomycin phosphotransferase gene, using the DOTAP liposome-based transfection reagents (Boehringer Mannheim, Mannheim, Germany). One day after the transfection the cells were transferred into selection media containing 0.5 mg/ml geneticin (GIBCO, Grand Island, N.Y.). Colonies of geneticin-resistant cells were isolated and analyzed for expression of the Flt4 proteins. Cells were lysed in boiling lysis buffer containing 3.3% SDS (sodium dodecyl sulphate), 125 mM Tris, pH 6.8. Protein concentrations of the samples were measured by the BCA method (Pierce, Rockford, Ill.). About 50 μg of protein of each lysate were analyzed for the presence of Flt4 by 6% SDS-polyacrylamide gel electrophoresis (SDS-PAGE) and immunoblotting using antisera against the carboxyl terminus of Flt4 and the ECL method (Amersham).

For production of anti-Flt4 antiserum the Flt4 cDNA fragment encoding the 40 carboxy-terminal amino acid residues of the short form: NH2- PMTPTTYKG SVDN- QTDSGM VLASEEFEQI ESRHRQESGFR-COOH (SEQ ID NO: 8) was cloned as a 657 bp EcoRI-fragment into the pGEX-1λT bacterial expression vector (Pharmacia) in frame with the glutathione-S-transferase coding region. The resultant GST-Flt4S fusion protein was produced in E. coli and purified by affinity chromatography using a glutathione-Sepharose 4B column. The purified protein was lyophilized, dissolved in phosphate buffered saline (PBS), mixed with Freund's adjuvant and used for immunization of rabbits at biweekly intervals using methods standard in the art (Harlow and Lane, Antibodies, A Laboratory Manual, Cold Spring Harbor Laboratory Press, 1988). Antisera were used after the fourth booster immunization for immunoprecipitation of Flt4 from the transfected cells and cell clones expressing Flt4 were used for ligand stimulation analysis.

EXAMPLE 3

Figure 3:
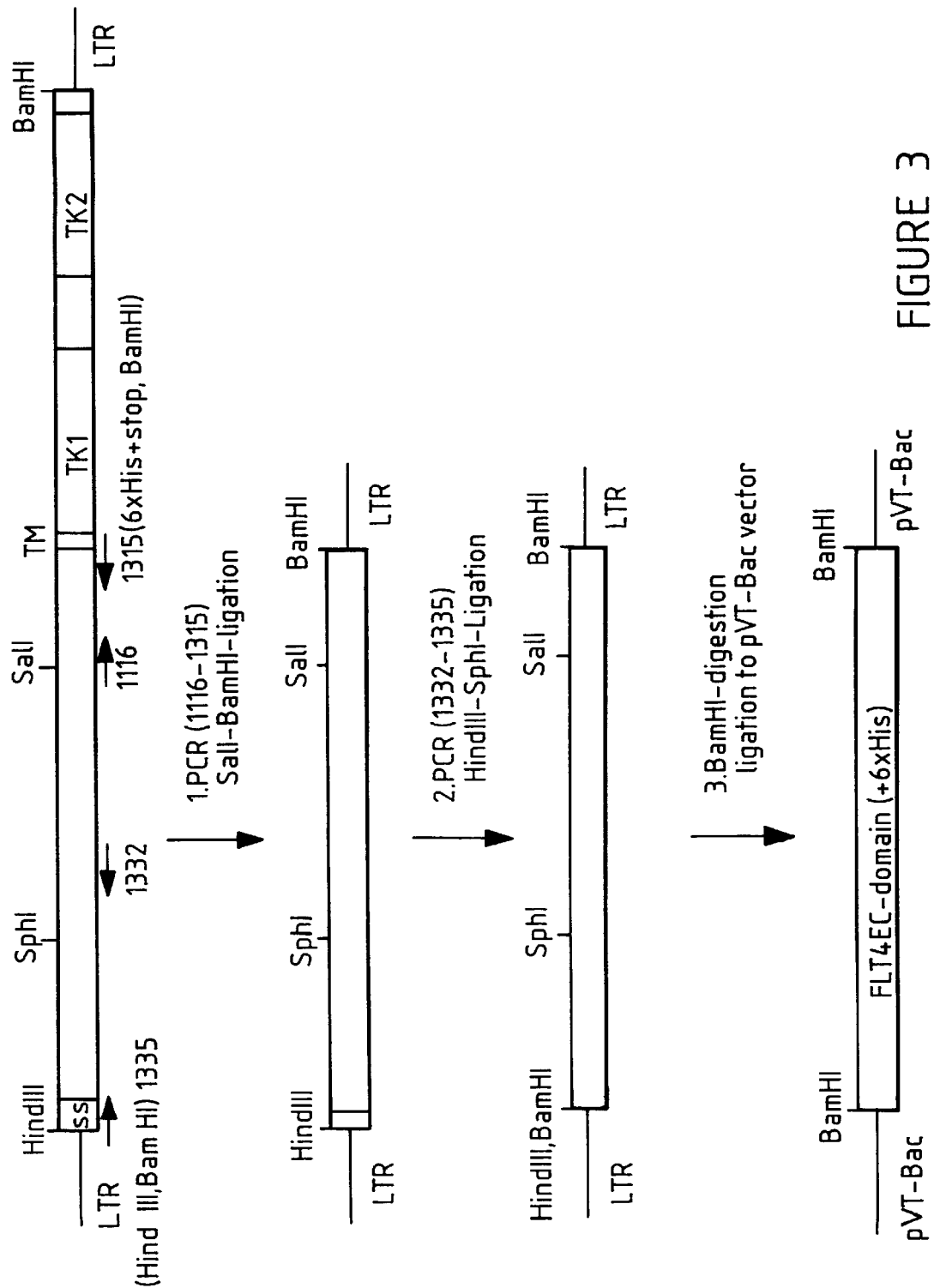
FIG. 3 schematically depicts the construction of the baculovirus vector encoding a secreted soluble Flt4 extracellular domain (Flt4EC).

Construction of a Flt4 EC Baculovirus Vector and Expression and Purification of its Product The construction of an Flt4 extracellular domain (EC) baculovirus vector is schematically shown in FIG. 3. The Flt4-encoding cDNA has been prepared in both a long form and a short form, each being incorporated in a vector under control of the Moloney murine leukemia virus LTR promoter. The nucleotide sequence of the short form of the Flt4 receptor is available on the Genbank database as Accession No. X68203 and the specific 3' segment of the long form cDNA is available as Accession No. S66407.

The ends of a cDNA segment encoding Flt4 extracellular domain (EC) were modified as follows: The 3' end of Flt4 cDNA sequence (Genbank Accession Number X68203) which encodes the extracellular domain was amplified using primer 1116 5'-CTGGA<u>GTCGAC</u>TTGGCGGACT-3' (SEQ ID NO: 9, SalI site underlined) and primer 1315 5'-CGC <u>GGATCCC</u>TAGTGATGGTGATGGTGATGTCTACCTTC GATCATGCT GCCCTTAT CCTC-3' (SEQ ID NO: 10, BamHI site underlined). The sequence complementary to that of primer 1315 continues after the Flt4 reading frame and encodes 6 histidine residues for binding to a Ni-NTA column (Qiagen, Hilden, Germany) followed by a stop codon, and an added Bam HI site. The amplified fragment was digested with SalI and BamHI and used to replace a unique SalI-BamHI fragment in the LTRFlt4 vector shown in FIG. 3. The SalI-BamHI fragment that was replaced encodes the Flt4 transmembrane and cytoplasmic domains.

The 5' end without the Flt4 signal sequence encoding region was amplified by PCR using the primer. 1335 5'-CCC<u>AAGCTTGGATCC</u>AAGTGGCTACTCCATGACC-3' (SEQ ID NO: 11) (the primer contains added HindIII (AAGCTT) and BamHI (GGATCC) restriction sites, which are underlined) and primer 1332 5'-GTTGCCTGTGATGTGCACCA-3' (SEQ ID NO: 12). The amplified fragment was digested with HindIII and SphI (the HindIII site (AAGCTT) is underlined in primer 1335 and the SphI site is within the amplified region of the Flt4l cDNA). The resultant HindIII-SphI fragment was used to replace a HindIII-SphI fragment in the modified LTRFlt4l vector described immediately above (the HindIII site is in the 5' junction of the Flt4 insert with the pLTRpoly portion of the vector, the SphI site is in Flt4 cDNA). The resultant Flt4EC insert was then ligated as a BamHI fragment into the BamHI site in the pVTBac plasmid as disclosed in Tessier et al., Gene 98: 177–183 (1991), incorporated by reference herein. The orientation was confirmed to be correct by partial sequencing so that the open reading frame of the signal sequence-encoding portion of the vector continued in frame with the Flt4 sequence. That construct was transfected together with the baculovirus genomic DNA into SF-9 cells by lipofection. Recombinant virus was purified, amplified and used for infection of High-Five cells (Invitrogen, San Diego, Calif.) using methods standard in the art. The Flt4 extracellular domain (Flt4EC) was purified from the culture medium of the infected High-Five cells using Ni-NTA affinity chromatography according to manufacturer's instructions (Qiagen) for binding and elution of the 6xHis tag encoded in the COOH-terminus of the recombinant Flt4 extracellular domain.

EXAMPLE 4

Isolation of Flt4 Ligand from Conditioned Media

An Flt4 ligand according to the invention was isolated from conditioned media from PC-3 prostatic adenocarcinoma cell line CRL1435 from the American Type Culture Collection and cultured as instructed by the supplier in Ham's F-12 Nutrient mixture (GIBCO) containing 7% fetal calf serum. In order to prepare the conditioned media, confluent PC-3 cells were cultured for 7 days in Ham's F-12 Nutrient mixture (GIBCO) in the absence of fetal bovine serum. Medium was then cleared by centrifugation at 10,000 g for 20 minutes. The medium was then screened to determine its ability to induce tyrosine phosphorylation of Flt4 by exposure to NIH3T3 cells which had been transfected with Flt4-encoding cDNA using the pLTRFlt4l vector. For receptor stimulation experiments, subconfluent NIH3T3 cells were starved overnight in serum-free DMEM medium (GIBCO) containing 0.2% BSA. The cells were stimulated with the conditioned media for 5 minutes, washed twice with cold PBS containing 100 uM vanadate and lysed in RIPA buffer (10 mM Tris pH 7.5, 50 mM NaCl, 0.5% sodium deoxycholate, 0.5% Nonidet P40 (BDH, Poole, England), 0.1% SDS, 0.1 U/ml Aprotinin (Boehringer Mannheim), 1 mM vanadate) for receptor immunoprecipitation analysis. The lysates were centrifuged for 20 minutes at 15,000×g. The supernatants were incubated for 2 hours on ice with 3 ul of the antiserum against the Flt4 C-terminus described in Example 2 and also in Pajusola, et al. *Oncogene* 8: 2931–2937, (1993), incorporated by reference herein.

After a 2 hour incubation in the presence of anti-Flt4 antiserum, protein A-Sepharose (Pharmacia) was added and incubation was continued for 45 minutes with rotation. The immunoprecipitates were washed three times with the immunoprecipitation buffer and twice with 10 mM Tris, pH7.5 before analysis in SDS-PAGE. Polypeptides were transferred to nitrocellulose and analyzed by Western blotting using Flt4- or phosphotyrosine-specific antisera and the ECL method (Amersham International, Buckinghamshire, England). Anti-phosphotyrosine monoclonal antibodies (anti-PTyr; PY20) were purchased from Transduction Laboratories (Lexington, Ky.). In some cases, the filters were restained with a second antibody after stripping. The stripping of the filters was done for 30 minutes at 5° C. in 100 mM 2-mercaptoethanol, 2% SDS, 62.5 mM Tris-HCl pH 6.7 with occasional agitation.

Figure 4:
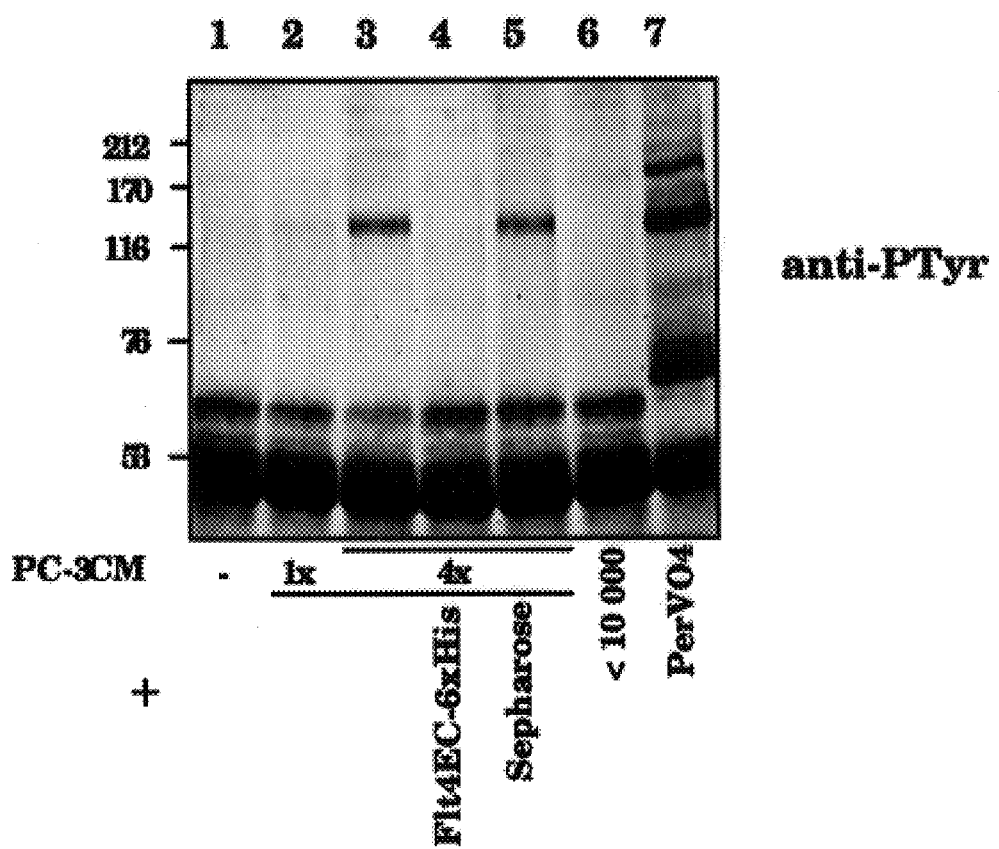
FIG. 4 shows results of stimulation of Flt4 autophosphorylation by conditioned medium from PC-3 cell cultures.
Figures 5A, 5B:
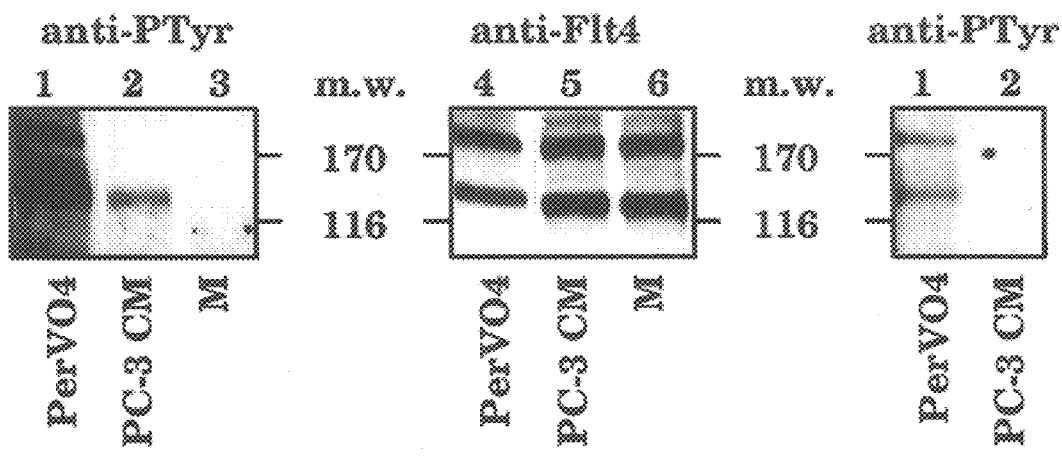
FIGS. 5A, 5B, and 5C show that the major tyrosyl phosphorylated polypeptide of Flt4-transfected cells stimulated with PC-3 conditioned medium is the 125 kD Flt4 polypeptide (VEGFR-3).
Figure 5C:
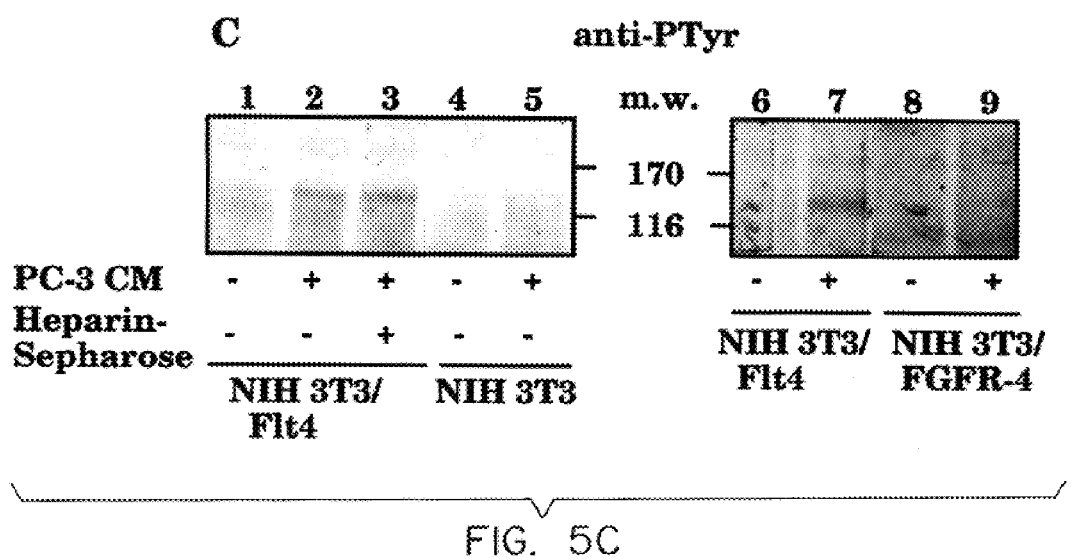

As shown in FIG. 4, the PC-3 cell conditioned medium stimulated tyrosine phosphorylation of a 125 kD polypeptide when Flt4-expressing NIH3T3 cells were treated with the indicated preparations of media, lysed, and the lysates were immunoprecipitated with anti-Flt4 antiserum followed by SDS-PAGE, Western blotting, and staining using anti-PTyr antibodies. The resulting band was weakly phosphorylated upon stimulation with unconcentrated PC-3 conditioned medium (lane 2). The 125 kD band comigrated with the tyrosine phosphorylated, processed form of the mature Flt4 from pervanadate-treated cells (compare lanes 2 and 7 of FIG. 4, see also FIG. 5A). Comigration was confirmed upon restaining with anti-Flt4 antibodies as is also shown in FIG. 5A (panel on the right). In order to show that the 125 kD polypeptide is not a non-specific component of the conditioned medium reactive with anti-phosphotyrosine antibodies, 15 ul of conditioned medium were separated by SDS-PAGE, blotted on nitrocellulose and the blot was stained with anti-PTyr antibodies. No signal was obtained (FIG. 5B). Also, unconditioned medium failed to stimulate Flt4 phosphorylation, as shown in FIG. 4, lane 1.

As shown in FIG. 4, lane 3, stimulating activity was considerably increased when the PC-3 conditioned medium was concentrated four-fold using a Centricon-10 concentrator (Amicon). FIG. 4, lane 4, shows that pretreatment of the concentrated PC-3 conditioned medium with 50 ul of the Flt4 extracellular domain coupled to CNBr-activated sepharose CL-4B (Pharmacia; about 1 mg of Flt4EC domain/ml sepharose resin) completely abolished Flt4 tyrosine phosphorylation. Similar pretreatment of the conditioned medium with unsubstituted sepharose CL-4B did not affect stimulatory activity, as shown in FIG. 4, lane 5. Also, the flow through obtained after concentration, which contained proteins of less than 10,000 molecular weight, did not stimulate Flt4 phosphorylation, as shown in FIG. 4, lane 6.

The foregoing data show that PC-3 cells produce a ligand which binds to the extracellular domain of Flt4 and activates this receptor.

EXAMPLE 5

Purification of the Flt4 Ligand

The ligand expressed by PC-3 cells as characterized in Example 4 was purified and isolated using a recombinantly-produced Flt4 extracellular domain (Flt4EC) in affinity chromatography.

Two harvests of serum-free conditioned medium, comprising a total of 8 L, were collected from 500 confluent 15 cm diameter culture dishes containing confluent layers of PC-3 cells. The conditioned medium was clarified by centrifugation at 10,000×g and concentrated 80-fold using an Ultrasette Tangential Flow Device (Filtron, Northborough, Mass.) with a 10 kD cutoff Omega Ultrafiltration membrane according to the manufacturer's instructions. Recombinant Flt4 extracellular domain was expressed in a recombinant baculovirus cell system and purified by affinity chromatography on Ni-agarose (Ni-NTA affinity column obtained from Qiagen). The purified extracellular domain was coupled to CNBr-activated Sepharose CL-4B at a concentration of 5 mg/ml and used as an affinity matrix for ligand affinity chromatography.

Concentrated conditioned medium was incubated with 2 ml of the recombinant Flt4 extracellular domain-Sepharose affinity matrix in a rolling tube at room temperature for 3 hours. All subsequent purification steps were at +4° C. The affinity matrix was then transferred to a column (Pharmacia) with an inner diameter of 15 mm and washed successively with 100 ml of PBS and 50 ml of 10 mM Na-phosphate buffer (pH 6.8). Bound material was eluted step-wise with 100 mM glycine-HCl, successive 6 ml elutions having pHs of 4.0, 2.4, and 1.9. Several 2 ml fractions of the eluate were collected in tubes containing 0.5 ml 1 M Na-phosphate (pH 8.0). Fractions were mixed immediately and dialyzed in 1 mM Tris-HCl (pH 7.5). Aliquots of 75 ul each were analyzed for their ability to stimulate tyrosine phosphorylation of Flt4. The ultrafiltrate, 100 ul aliquots of the concentrated conditioned medium before and after ligand affinity chromatography, as well as 15-fold concentrated fractions of material released from the Flt4 extracellular domain-Sepharose matrix during the washings were also analyzed for their ability to stimulate Flt4 tyrosine phosphorylation.

Figure 6:
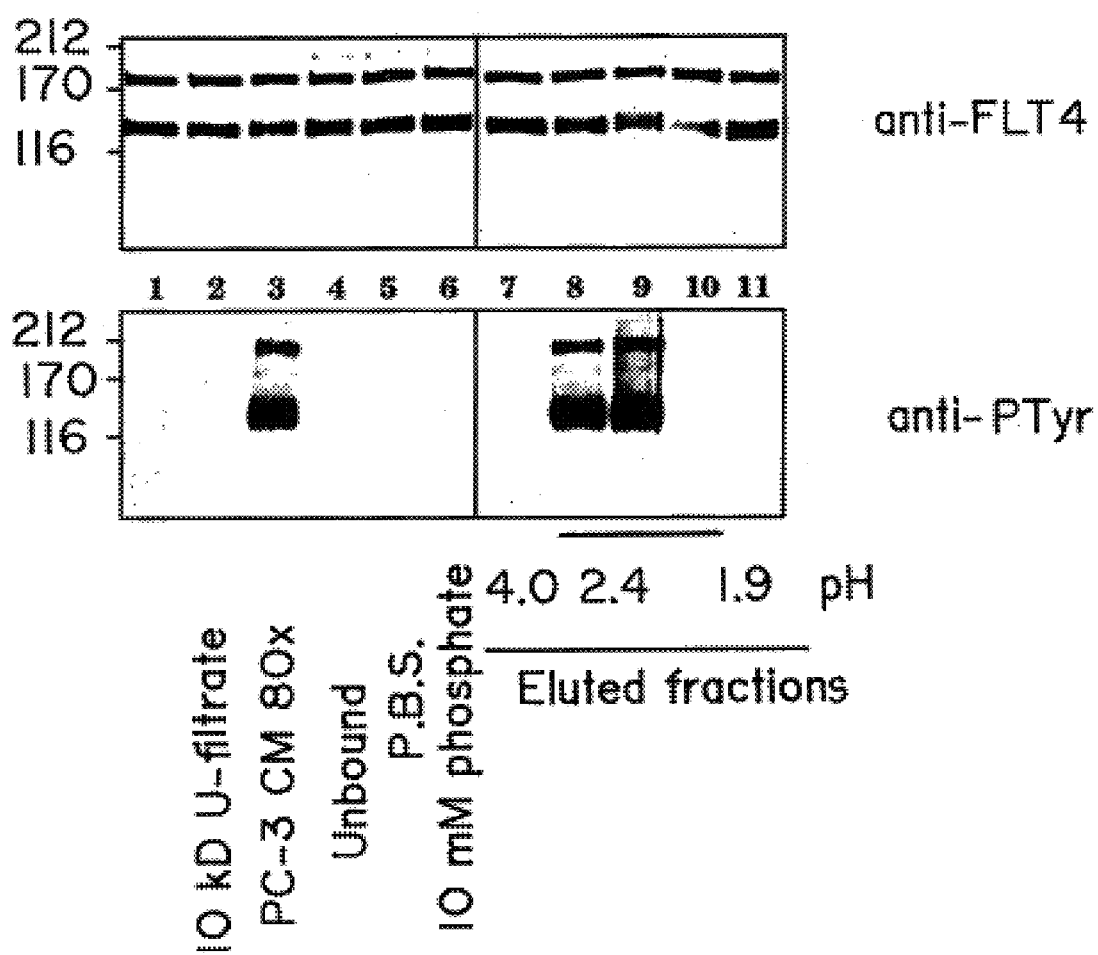
FIG. 6 shows Western analysis of the Flt4 ligand activity isolated from PC-3 conditioned medium.

As shown in FIG. 6, lane 3, the concentrated conditioned medium induced prominent tyrosine phosphorylation of Flt4 in transfected NIH3T3 cells overexpressing Flt4. This activity was not observed in conditioned medium taken after medium was exposed to the Flt4 Sepharose affinity matrix described above (lane 4). The specifically-bound Flt4-stimulating material was retained on the affinity matrix upon washes in PBS, 10 mM Na-phosphate buffer (pH 6.8), and at pH 4.0 (lanes 5–7, respectively), and it was eluted in the first two 2 ml aliquots at pH 2.4 (lanes 8 and 9). A further decrease of the pH of the elution buffer did not cause release of additional Flt4-stimulating material (lane 11).

Figure 7:
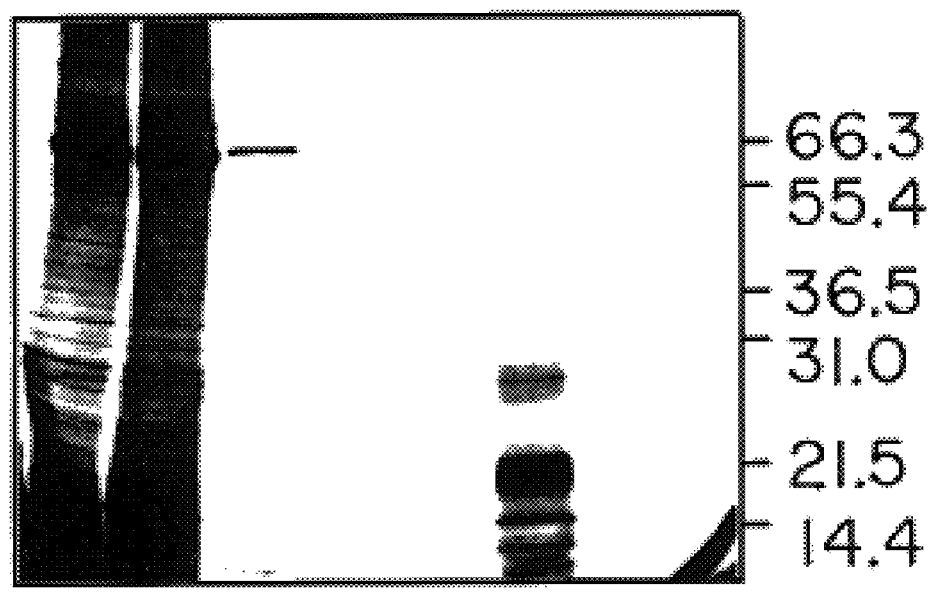
FIG. 7 shows results of gel electrophoresis of chromatographic fractions from the affinity purification of Flt4 ligand (VEGF-C) isolated from PC-3 conditioned medium.
Figure 7:
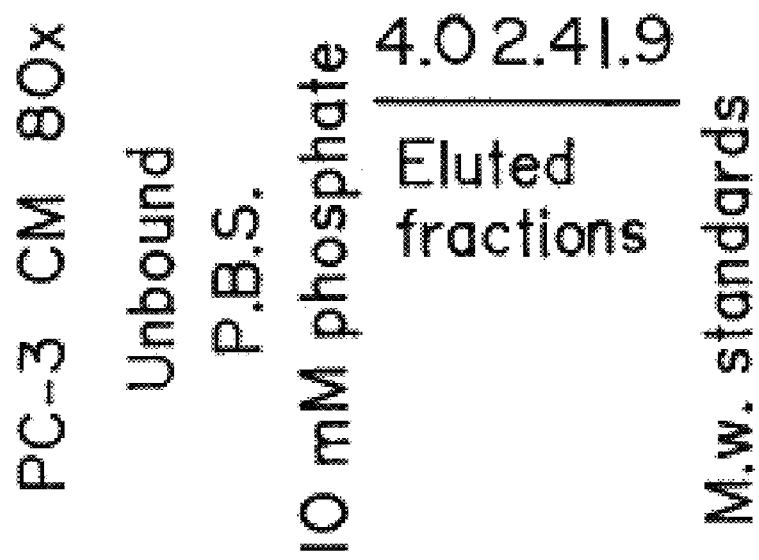
Figure 8:
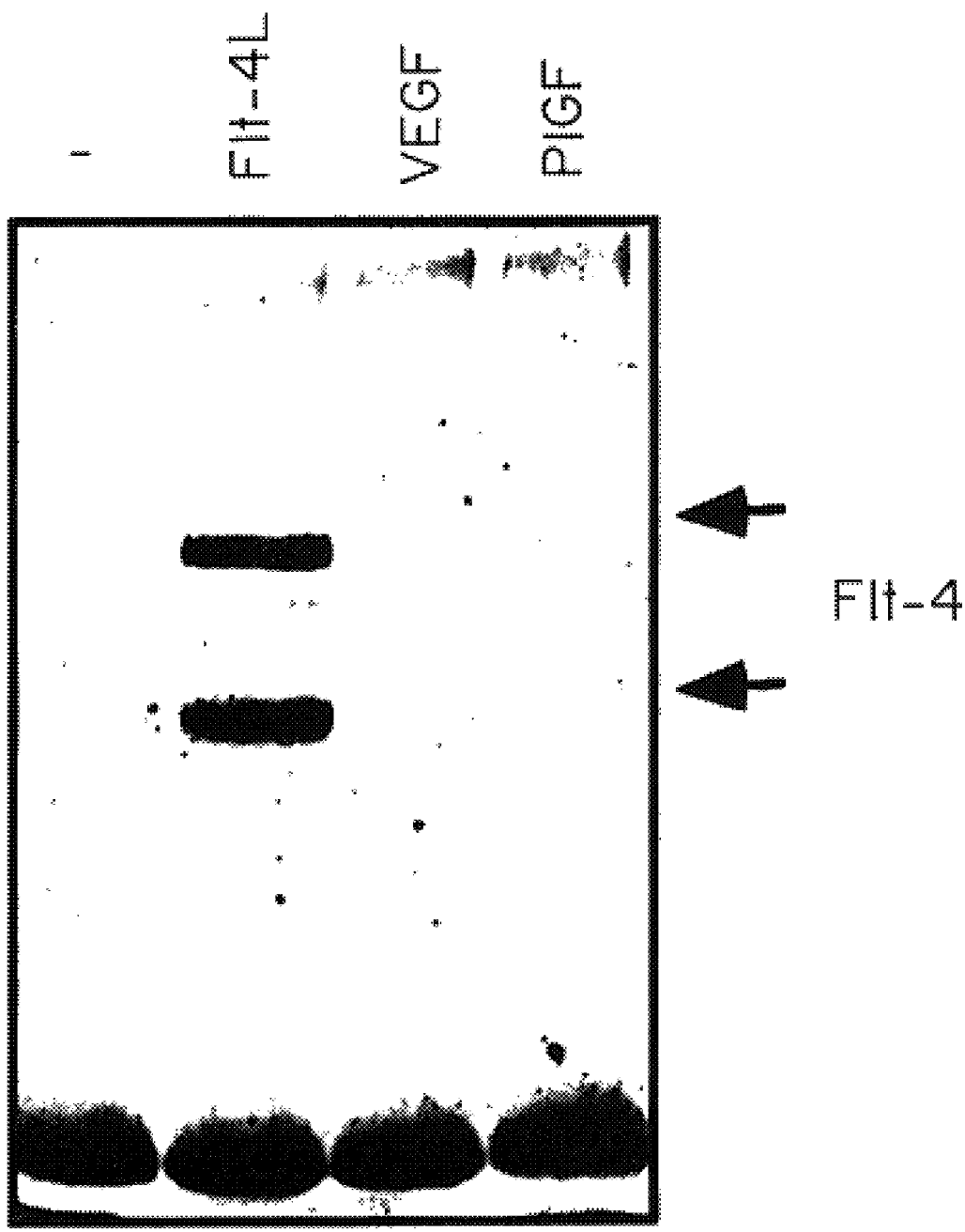
FIG. 8 shows results of Western analysis of Flt4 autophosphorylation induced by either the Flt4 ligand (VEGF-C), VEGF, or PlGF.

Small aliquots of the chromatographic fractions were concentrated in a SpeedVac concentrator (Savant, Farmingdale, N.Y.) and subjected to SDS-PAGE under reducing conditions with subsequent silver staining of the gel. As shown in FIG. 7, the major polypeptide, having a molecular weight of approximately 23 kD (reducing conditions), was detected in the fractions containing Flt4 stimulating activity (corresponding to lanes 8 and 9 in FIG. 6). That polypeptide was not found in the other chromatographic fractions. On the other hand, all other components detected in the two active fractions were also distributed in the starting material and in small amounts in the other washing and elution steps after their concentration. Similar results were obtained in three independent affinity purifications, indicating that the 23 kD polypeptide specifically binds to Flt4 and induces its tyrosine phosphorylation.

Fractions containing the 23 kD polypeptide were combined, dried in a SpeedVac concentrator and subjected to SDS-PAGE in a 12.5% gel. The proteins from the gel were then electroblotted to Immobilon-P (PVDF) transfer membrane (Millipore, Marborough, Mass.) and visualized by staining of the blot with Coomassie blue R-250. The region containing only the stained 23 kD band was cut from the blot and was subjected to N-terminal amino acid sequence analysis in a Prosite Protein Sequencing System (Applied Biosystems, Foster City, Calif.). The data were analyzed using a 610A Data Analysis System (Applied Biosystems). Analysis revealed a single N-terminal sequence of $NH_2$-XEETIKFAAAHYNTEILK-COOH (SEQ ID NO: 13).

EXAMPLE 6

Construction of PC-3 Cell cDNA Library in a Eukaryotic Expression Vector

Poly(A)$^+$ RNA was isolated from five 15 cm diameter confluent dishes of PC-3 cells by a single step method using oligo(dT) (Type III, Collaborative Research) cellulose affinity chromatography (Sambrook et al., Molecular Cloning, A Laboratory Manual; Cold Spring Harbor Laboratory Press, 1989). The yield was 70 μg. Six micrograms of the Poly(A)$^+$ RNA were used to prepare an oligo(dT)-primed cDNA library in the mammalian expression vector pcDNA I and the Librarian kit of Invitrogen according to the instructions included in the kit. The library was estimated to contain about $10^6$ independent recombinants with an average insert size of approximately 1.8 kb.

EXAMPLE 7

Amplification of the Unique Nucleotide Sequence Encoding the Flt4 Ligand

Figure 9A:
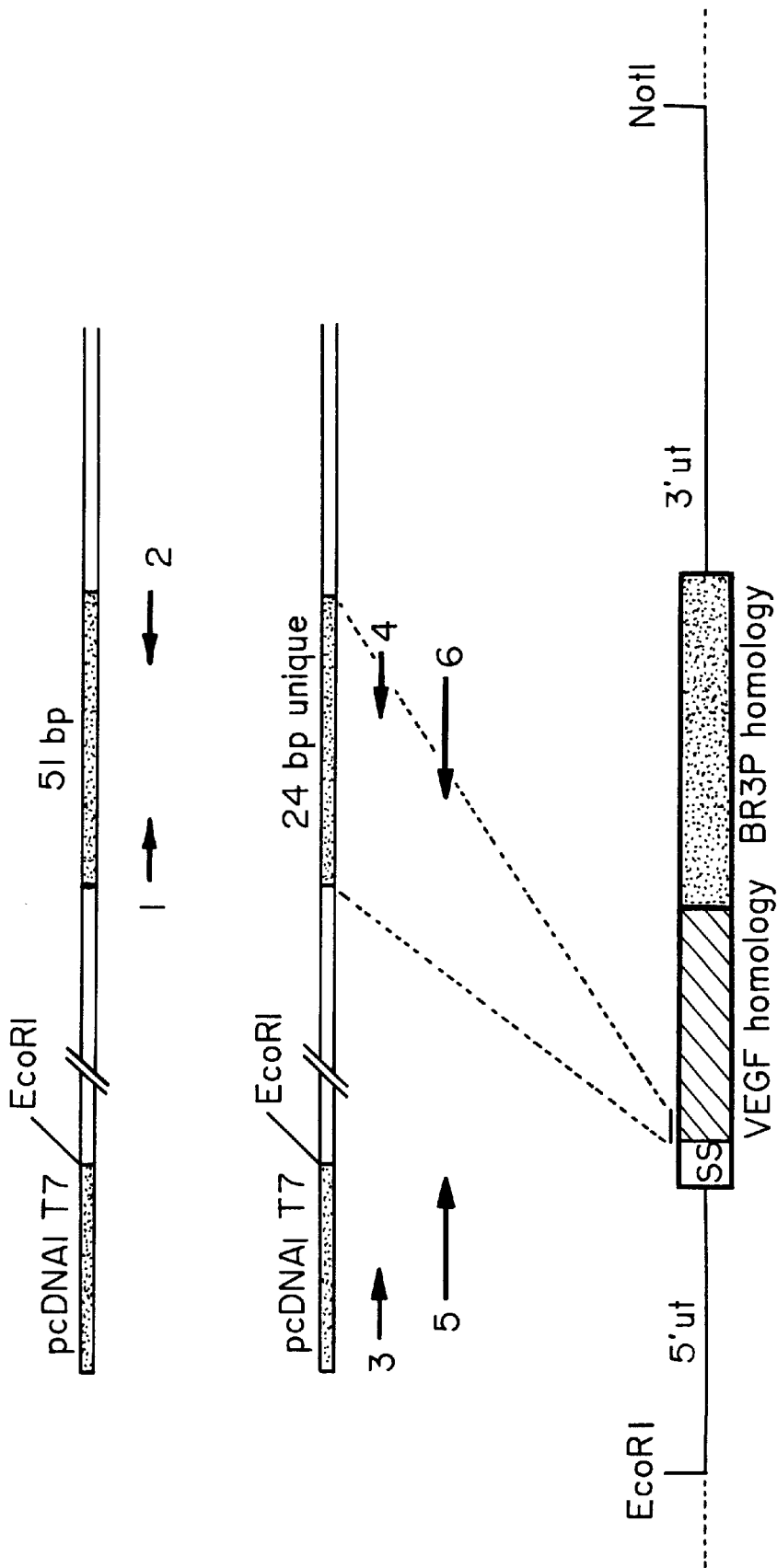
FIG. 9A schematically depicts the cloning and analysis of the Flt4 ligand, VEGF-C. The VEGF-C coding sequence (shaded boxes) and signal sequence (ss) are depicted between 5' and 3' untranslated (ut) nucleic acid regions.

Degenerate oligonucleotides were designed based on the N-terminal amino acid sequence of the isolated Flt4 ligand and were used as primers in a polymerase chain reaction (PCR) to amplify cDNA encoding the Flt4 ligand from a PC-3 cell library. The overall strategy is schematically depicted in FIG. 9A, where the different primers have been marked with arrows.

The PCR was carried out using 1 μg of DNA from the amplified PC-3 cDNA library and a mixture of sense-strand primers comprising 5'-GCAGARGARACNATHAA-3' (SEQ ID NO: 14)(wherein R is A or G, N is A,G,C or T and H is A, C or T), encoding amino acid residues 2–6 (EETIK, SEQ ID NO: 15) and antisense-strand primers 5'-GCAYTTNARDATYTCNGT-3' (SEQ ID NO: 16) (wherein Y is C or T and D is A, G or T), corresponding to amino acid residues 14–18 (TEILK, SEQ ID NO: 17). Three extra nucleotides (GCA) were added to the 5'-terminus of each primer to increase annealing stability. Two successive PCR runs were carried out using 1 U per reaction of DynaZyme (F-500L, Finnzymes), a thermostable DNA polymerase, in a buffer supplied by the manufacturer (10 mM Tris-HCl, pH 8.8 at 25° C., 1.5 mM $MgCl_2$, 50 mM KCl, 0.1% Triton-X100), at an extension temperature of 72° C. The first PCR run was carried out for 43 cycles. The first three cycles were run at an annealing temperature of 33° C. for 2 minutes, and the remaining cycles were run at 42° C. for 1 minute.

The region of the gel containing a weak band of the expected size (57 bp) was cut out from the gel and eluted. The eluted material was reamplified for 30 cycles using the same primer pairs described above at 42° C. for 1 minute. The amplified fragment was cloned into a pCR II vector (Invitrogen) using the TA cloning kit (Invitrogen) and sequenced using the radioactive dideoxynucleotide sequencing method of Sanger. Six clones were analyzed and all contained the sequence encoding the expected peptide (amino acids 2–18 of the Flt4 ligand precursor). Nucleotide sequence spanning the region from the third nucleotide of codon 6 to the third nucleotide of codon 13 (the extension region) was identical in all six clones: 5'-ATTCGCTGCAGCACACTACAAC-3' (SEQ ID NO: 18) and thus was considered to represent an amplified product from the unique sequence encoding part of the amino terminus of the Flt4 ligand.

EXAMPLE 8

Amplification of the 5'-end of the cDNA Encoding the Flt4 Ligand

Based on the unique nucleotide sequence encoding the N-terminus of the isolated Flt4 ligand, two pairs of nested primers were designed to amplify, in two subsequent PCR-reactions, the complete 5'-end of the corresponding cDNAs from one microgram of DNA from the above-described PC-3 cDNA library. First, amplification was performed with primer 5'-TCNGTGTTGTAGTGTGCTG-3' (SEQ ID NO: 19), which is the antisense-strand primer corresponding to amino acid residues 9–15 (AAHYNTE, SEQ ID NO: 20), and sense-strand primer 5'-TAATACGACTCACTATAGGG-3' (SEQ ID NO: 21), corresponding to the T7 RNA promoter of the pcDNAI vector used for construction of the library. "Touchdown"

PCR was used as disclosed in Don, et al., *Nucl. Acids Res.*, 19: 4008 (1991), incorporated by reference herein. The annealing temperature of the two first cycles was 62° C. and subsequently the annealing temperature was decreased in every other cycle by 1° C. until a final temperature of 53° C. was reached, at which temperature 16 additional cycles were conducted. Annealing time was 1 minute and extension at each cycle was conducted at 72° C. for 1 minute. Multiple amplified DNA fragments were obtained in the first reaction. The products of the first amplification (1 ul of a 1:100 dilution in water) were used in the second amplification reaction employing the nested primers 5'-GTTGTAGTGTGCTGCAGCGAATT-3' (SEQ ID NO: 22), an antisense-strand primer corresponding to amino acid residues 6–13 (KFAAAHYN, SEQ ID NO: 23) of the Flt4 ligand, and 5'-TCACTATAGGGAGACCCAAGC-3' (SEQ ID NO: 24), a sense-strand primer corresponding to nucleotides 2179–2199 of the pcDNAI vector. The sequences of these sense and antisense primers overlapped with the 3' ends of the corresponding primers used in the first PCR. "Touchdown" PCR was carried out by decreasing the annealing temperature from 72° C. to 66° C. and continuing with 18 additional cycles at 66° C. The annealing time was 1 minute and extension at each cycle was carried out at 72° C. for 2 minutes. One major product of about 220 bp and three minor products of about 270 bp, 150 bp, and 100 bp were obtained.

The amplified fragment of approximately 220 bp was cut out from the agarose gel, cloned into a pCRII vector using the TA cloning kit (Invitrogen) and sequenced. Three recombinant clones were analyzed and they contained the sequence 5'-TCACTATAGGGAGACCCAAGCTTGGTACCGAGCT CGGATCCACTAGT AACGGCCGCCAGTGTGGTG- GAATTC<u>GACGAACTCATGACTGTACTCT ACCCAGAATATTGGAAAATGTACAAGTGTCAGCTAA GGCAAGGAGGC TGGCAACATAACAGAGAACAGGCCAACCTCAACTC AAGGACAGAAG AGACTATAAAATTCGCTGCAGCACACTACAAC</u>- 3' (SEQ ID NO: 25). The beginning of the sequence represents the pcDNAI vector and the underlined sequence represents the amplified product of the 5'-end of the insert. The ATG codon located upstream of that sequence in the same reading frame is followed by an open reading frame containing the amplified product of the putative signal sequence and the first 13 amino acid residues of the secreted Flt4 ligand. The cloning of the 5' end of the Flt4 cDNA, as described in the preceding two examples, is depicted schematically in FIG. 9A.

EXAMPLE 9

Amplification of the 3'-end of cDNA Encoding the Flt4 Ligand

Based upon the amplified 5'-sequence of the clones encoding the Flt4 ligand, two pairs of non-overlapping nested primers were designed to amplify the 3'-portion of the FLT4-L clones. The sense-strand primer 5'-ACAGAGAACAGGCCAACC-3' (SEQ ID NO: 26) and antisense-strand primer 5'-TCTAGCATTTAGGTGACAC-3' (SEQ ID NO: 27) corresponding to nucleotides 2311–2329 of the pcDNAI vector were used in a first "touchdown" PCR. The annealing temperature of the reaction was decreased 1° C. every two cycles from 72° C. to 52° C., at which temperature 15 additional cycles were carried out. The annealing time was 1 minute and extension at each cycle was carried out at 72° C. for 3 minutes. DNA fragments of several sizes were obtained in the first amplification. Those products were diluted 1:200 in water and reamplified in PCR using the second pair of primers: 5'-AAGAGACTATAAAATTCGCTGCAGC-3' (SEQ ID NO: 28) and 5'-CCCTCTAGATGCATGCTCGA-3' (SEQ ID NO: 29) (antisense-strand primer corresponding to nucleotides 2279–2298 of the pcDNAI vector). Two DNA fragments were obtained, having sizes of 1350 bp and 570 bp. Those fragments were cloned into a pCRII vector and the inserts of the clones were sequenced. Both of these fragments were found to contain sequences encoding an amino acid sequence homologous to the VEGF sequence.

EXAMPLE 10

Screening the PC-3 Cell cDNA Library Using the 5' PCR Fragment of Flt4 Ligand cDNA A 219 bp 5'-terminal fragment of Flt4 ligand cDNA was amplified by PCR using the 5' PCR fragment described above and primers 5'-GTTGTAGTGTGCTGCAGCGAATTT-3' (antisense-strand primer, SEQ ID NO: 30) and 5'-TCACTATAGGGAGACCCAAGC-3' (SEQ ID NO: 31) (sense-primer corresponding to nucleotides 2179–2199 of the pcDNAI vector). The amplified product was subjected to digestion with EcoRI (Boehringer Mannheim) to remove the portion of the DNA sequence amplified from the pcDNAI vector and the resulting 153 bp fragment encoding the 5' end of the Flt4 ligand was labeled with [$^{32}$P]-dCTP using the Klenow fragment of *E. coli* DNA polymerase I (Boehringer Mannheim). That fragment was used as a probe for hybridization screening of the amplified PC-3 cell cDNA library.

Filter replicas of the library were hybridized with the radioactively labeled probe at 42° C. for 20 hours in a solution containing 50% formamide, 5×SSPE, 5×Denhardt's solution, 0.1% SDS and 0.1 mg/ml denatured salmon sperm DNA. Filters were washed twice in 1×SSC, 0.1% SDS for 30 minutes at room temperature, then twice for 30 minutes at 65° C. and exposed overnight.

On the basis of autoradiography, 10 positive recombinant bacterial colonies hybridizing with the probe were chosen from the library. Plasmid DNA was purified from these colonies and analyzed by EcoRI and NotI digestion and agarose gel electrophoresis followed by ethidium bromide staining. The ten plasmid clones were divided into three groups on the basis of the presence of insert sizes of approximately 1.7, 1.9 and 2.1 kb, respectively. Inserts of plasmids from each group were sequenced using the T7 oligonucleotide as a primer and walking primers for subsequent sequencing reactions.

Sequence analysis showed that all clones contain the open reading frame encoding the NH2-terminal sequence of the Flt4 ligand. Furthermore, the 2.1 and 1.9 kb clones also contained sequences encoding the signal sequence (FIG. 9A, SS). The 5' end of the 1.7 kb clone began within the signal sequence-encoding portion. Dideoxy sequencing was continued using walking primers in the downstream direction. An 1140 nucleotide portion of the sequence of the longest clone is shown in FIGS. 9B through 9D. As can be seen in that figure, after the putative signal sequence the open reading frame terminates in a TAA stop codon 318 amino acid residues further downstream from the 33 amino acid signal sequence. When compared with sequences in the GenBank Database, the predicted protein product of this reading frame was found to be homologous with the predicted amino acid sequences of the PDGF/VEGF family of growth factors, as shown in FIGS. 10A through 10D.

EXAMPLE 11

Stimulation of Flt4 Autophosphorylation by the Protein Product of the Flt4 Ligand Vector The 2.1 kb insert of the Flt4-L clone in pcDNAI vector containing the open reading frame encoding the sequence shown in FIGS. 9B through 9D (SEQ ID NO: 32) was cut out from the vector using HindIII and NotI restriction enzymes, isolated from a preparative agarose gel and ligated to the corresponding sites in the pREP7 expression vector (Invitrogen). The pREP7 vector containing the above cloned insert was transfected into 293-EBNA cells (Invitrogen) using the calcium phosphate transfection method (Sambrook et al., Molecular Cloning, A Laboratory Manual; Cold Spring Harbor Laboratory Press, 1989). About 48 hours after transfection the medium of the transfected cells was changed to DMEM medium lacking fetal calf serum and incubated for 36 h. The thus conditioned medium was then collected, centrifuged at 5000×g for 20 minutes, the supernatant was concentrated 5-fold using Centriprep 10 (Amicon) and used to stimulate NIH3T3 cells expressing LTRFlt4l, as in Example 4. The cells were lysed, immunoprecipitated using anti-Flt4 antiserum and analyzed by Western blotting using anti-phosphotyrosine antibodies.

Figure 11:
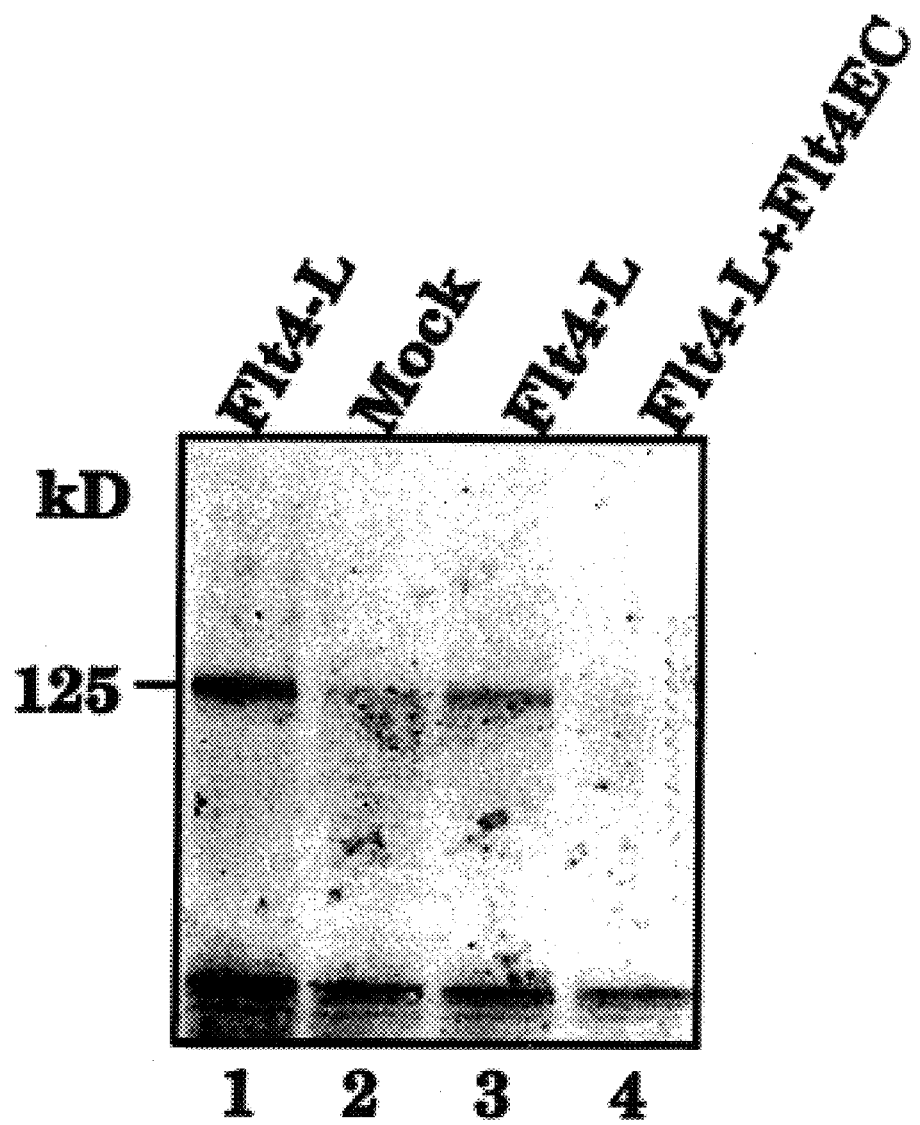
FIG. 11 shows the stimulation of autophosphorylation of the Flt4 receptor by conditioned medium from cells transfected with the Flt4-L (VEGF-C) expression vector.

As can be seen from FIG. 11, lanes 1 and 3, the conditioned medium from two different dishes of the transfected cells stimulated Flt4 autophosphorylation in comparison with the medium from mock-transfected cells, which gave only background levels of phosphorylation of the Flt4 receptor (lane 2). When the concentrated conditioned medium was pre-absorbed with 20 µl of a slurry of Flt4EC domain coupled to Sepharose (see example 4), no phosphorylation was obtained (lane 4), showing that the activity responsible for Flt4 autophosphorylation was indeed the Flt4 ligand. Thus, these results demonstrate that the Flt4-L plasmid vector clone having an approximately 2.1 kb insert and containing the open reading frame shown in FIG. 9B is expressed into a Flt4 ligand in cells transfected with the Flt4-L expression vector clone, and thus is biologically active. The sequence encoded by that open reading frame is shown in SEQ ID NO: 33. Plasmid pFLT4-L has been deposited with the American Type Culture Collection, 12301 Parklawn Drive, Rockville, Md. 20852 as accession number 97231. The approximately 2.1 kb cDNA insert of the deposited plasmid pFLT4-L was sequenced and found to have a nucleotide sequence that includes the 1997 nucleotides of sequence set forth in SEQ ID NO: 44. The nucleotide sequence set forth in SEQ ID NO: 44 encodes the 419 residue amino acid sequence set forth in SEQ ID NO: 45.

However, the predicted molecular weight of the mature protein product deduced from the reading frame specified in SEQ ID NOs: 32–33 is 35881 and the Flt4 ligand from PC-3 cell cultures had an approximate molecular weight of 23 kD under reducing conditions. It is thus possible that the Flt4-L mRNA may be first translated into a precursor, from which the mature ligand is derived by proteolytic cleavage. The difference in the observed molecular weight of the isolated Flt4 ligand and the deduced molecular weight of the disclosed open reading frame of the Flt4 ligand sequence may then derive from sequences in the carboxyl terminal region of the latter. Also, the Flt4 ligand may be glycosylated at two putative N-linked glycosylation sites conforming to the consensus which can be identified in the deduced Flt4 ligand amino acid sequence (N-residues underlined in FIGS. 10B and 10C.

The carboxyl terminal amino acid sequences, which increase the predicted molecular weight of the Flt4 ligand subunit in comparison with other ligands of this family, show a pattern of spacing of cysteine residues reminiscent of the Balbiani ring protein 3 (BR3P) sequence (Dignam and Case, Gene 88, 133–140, 1990), as depicted in FIG. 9A. Such a sequence may encode an independently folded domain present in a Flt4 ligand precursor and it may be involved, for example, in the regulation of secretion, solubility, stability, cell surface localization or activity of the Flt4 ligand. Interestingly, at least one cysteine motif of the BR3P type is also found in the VEGF carboxy terminal amino acid sequences.

Thus, the Flt4-L mRNA may be first translated into a precursor from the mRNA corresponding to the Flt4-L clone, from which the mature ligand is derived by proteolytic cleavage. To define the mature Flt4 ligand product one first expresses the cDNA clone, which is deposited in the pcDNAI expression vector, in cells, such as COS cells. One uses antibodies generated against Flt4-L-encoded peptides, such as amino terminal 23 amino acid peptide or bacterial Flt4 fusion proteins, such as a GST-fusion protein, to raise antibodies against the VEGF-homologous domain of Flt4 ligand. One then follows the biosynthesis and processing of the Flt4 ligand in the transfected cells by pulse-chase analysis using radioactive cysteine for labelling of the cells, immunoprecipitation and gel electrophoresis. Using antibodies against the two domains of the product of the Flt4-L clone material for radioactive or nonradioactive aminoterminal sequence analysis is isolated. The determination of the NH2-terminal sequence of the carboxyl terminal fragment allows for identification of the proteolytic processing site. This is confirmed by site-directed mutagenesis of the amino acid residues adjacent to the cleavage site, which would prevent the cleavage.

On the other hand, the Flt4 ligand is characterized by progressive 3' deletions in the 3' coding sequences of the Flt4 ligand precursor clone, resulting in carboxy-terminal truncations of its protein product. The activities of such truncated forms are assayed by, for example, studying Flt4 autophosphorylation induced by the truncated proteins when applied to cultures of cells, such as NIH3T3 cells expressing LTRFlt4. By extrapolation from studies of the structure of the related platelet derived growth factor (PDGF, reference Heldin et al., Growth Factors 8:245–252 (1993)) one determines that the region critical for receptor activation by the Flt4 ligand is contained within its first approximately 180 amino acid residues of the secreted VEGF-C protein lacking the signal sequence, and apparently within the first approximately 120 amino acid residues.

On the other hand, the difference between the molecular weights of the purified ligand and the open reading frame of the Flt4 precursor clone may be due to the fact that the soluble ligand was produced from an alternatively spliced mRNA which would also be present in the PC-3 cells, from which the isolated ligand was derived. To isolate such alternative cDNA clones one uses cDNA fragments of the deposited clone and PCR primers made according to the sequence provided as well as techniques standard in the art to isolate or amplify alternative cDNAs from the PC-3 cell cDNA library. One may also amplify using reverse transcription (RT)-PCR directly from the PC-3 mRNA using the primers provided in the sequence of the Flt4-L clone. Alternative cDNA sequences are determined from the resulting cDNA clones. One can also isolate genomic clones corresponding to the Flt4-L transcript from a human genomic DNA library using methods standard in the art and to sequence such clones or their subcloned fragments to reveal the corresponding exons. Alternative exons can then be identified by a number of methods standard in the art, such as heteroduplex analysis of cDNA and genomic DNA, which are subsequently characterized.

EXAMPLE 12

Expression of the Flt4L Gene

Figure 12:
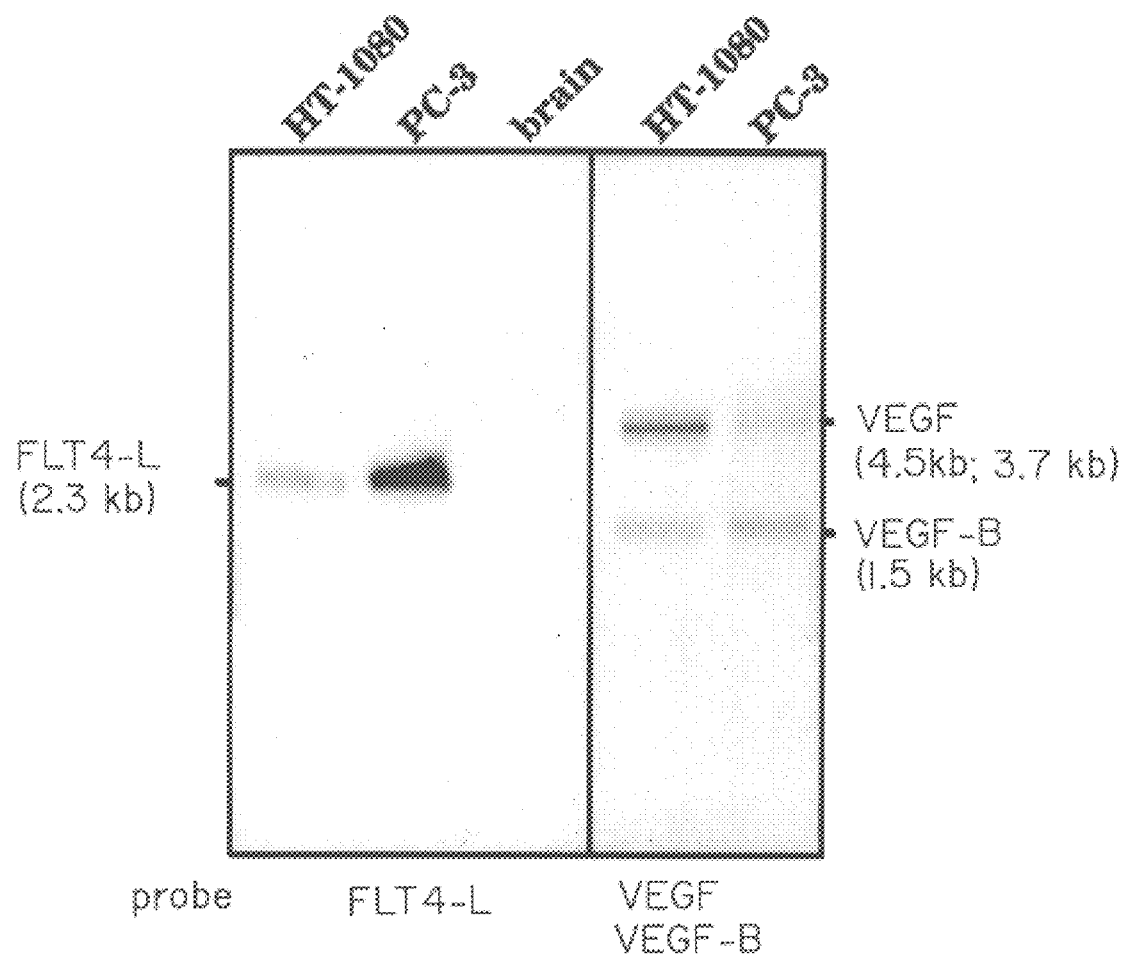
FIG. 12 shows Northern blotting analysis of Flt4-L (VEGF-C) mRNA in tumor cell lines and in brain tissue.

Expression of transcripts corresponding to the Flt4 ligand (VEGF-C) was analyzed by hybridization of Northern blots containing isolated poly(A)$^+$ RNA from HT-1080 and PC-3 human tumor cell lines. The probe was the radioactively labelled insert of the 2.1 kb cDNA clone (specific activity $10^8$–$10^9$ cpm/mg of DNA). The blot was hybridized overnight at 42° C. using 50% formamide, 5×SSPE buffer, 2% SDS, 10×Denhardt's solution, 100 mg/ml salmon sperm DNA and $1 \times 10^6$ cpm of the labelled probe/ml. The blot was washed at room temperature for 2×30 minutes in 2×SSC containing 0.05% SDS, and then for 2×20 min at 52° C. in 0.1×SSC containing 0.1% SDS. The blot was then exposed at −70° C. for three days using intensifying screens and Kodak XAR film. Both cell lines expressed an Flt4 ligand mRNA of about 2.3 kb, as well as VEGF and VEGF-B mRNA:s (FIG. 12).

EXAMPLE 13

VEGF-C Chains are Proteolytically Processed after Biosynthesis and Disulfide Linked The predicted molecular mass of the secreted polypeptide, as deduced from the VEGF-C ORF specified in SEQ ID NOs: 32 and 33, is 35,881 kD, suggesting that VEGF-C mRNA may be first translated into a precursor, from which the mature ligand of 23 kD is derived by proteolytic cleavage.

To study this, metabolic labelling of 293 EBNA cells transfected with the VEGF-C construct was carried out by addition of 100 μCi/ml of Pro-mix™ L-[$^{35}$S] in vitro cell labelling mix (Amersham) to the culture medium devoid of cysteine and methionine. After two hours, the cell layers were washed twice with PBS and the medium was then replaced with DMEM-0.2% BSA. After 1, 3, 6, 12 and 24 hours of subsequent incubation, the culture medium was collected, clarified by centrifugation, and concentrated, and VEGF-C was bound to 30 μl of a slurry of Flt4EC-Sepharose overnight at +4° C., followed by three washes in PBS, two washes in 20 mM Tris-HCl (pH 7.5), alkylation, SDS-PAGE and autoradiography.

Figure 13A:
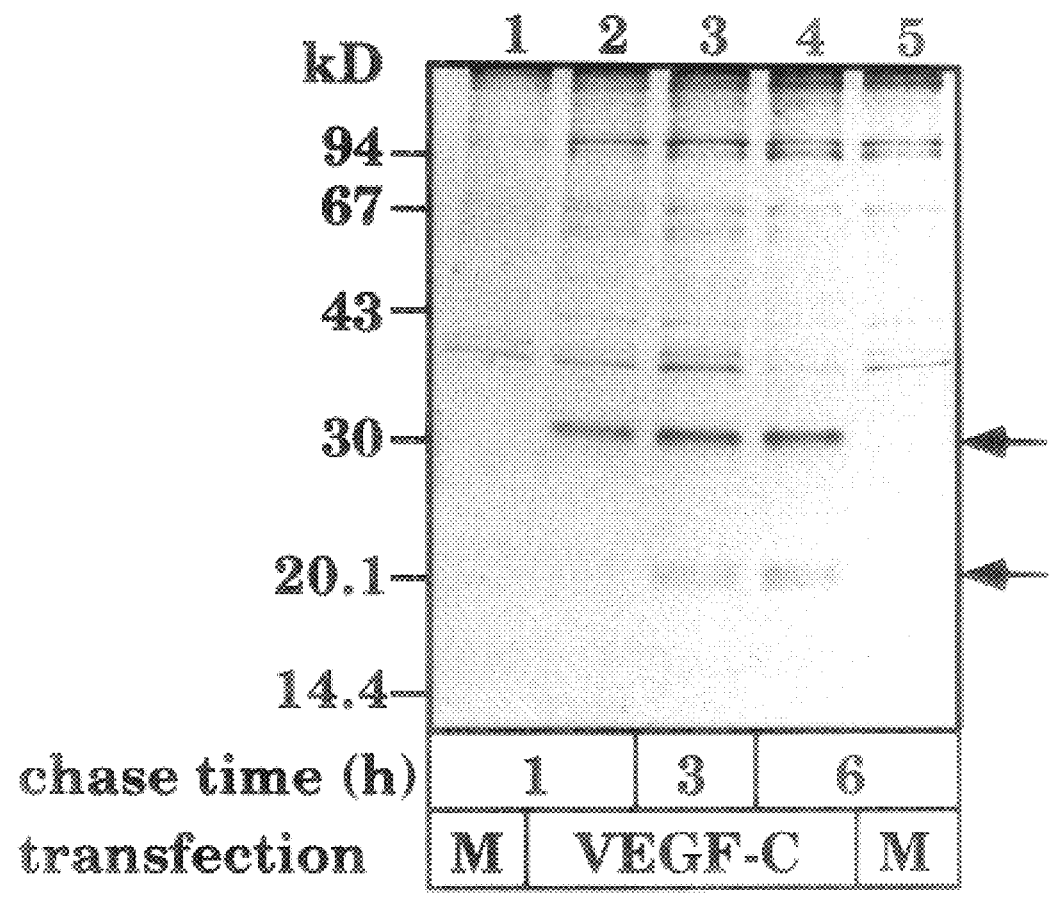
FIG. 13A is an autoradiograph showing recombinant VEGF-C isolated following a pulse-chase experiment and electrophoresed via SDS-PAGE under reducing conditions.

These experiments demonstrated that a putative precursor polypeptide of 32 kD apparent molecular mass was bound to the Flt4EC affinity matrix from the CM of metabolically labelled cells transfected with a VEGF-C expression vector (FIG. 13A). Increased amounts of a 23 kD receptor-binding polypeptide accumulated in the culture medium during a subsequent chase period of 3 h, but not thereafter (lanes 2–4 and data not shown), suggesting that the 23 kD form is produced by proteolytic processing, which is cell-associated and incomplete, at least in the transiently transfected cells. The arrows in FIG. 13A indicate the 32 kDa and 23 kDa polypeptides of secreted VEGF-C.

Figure 13B:
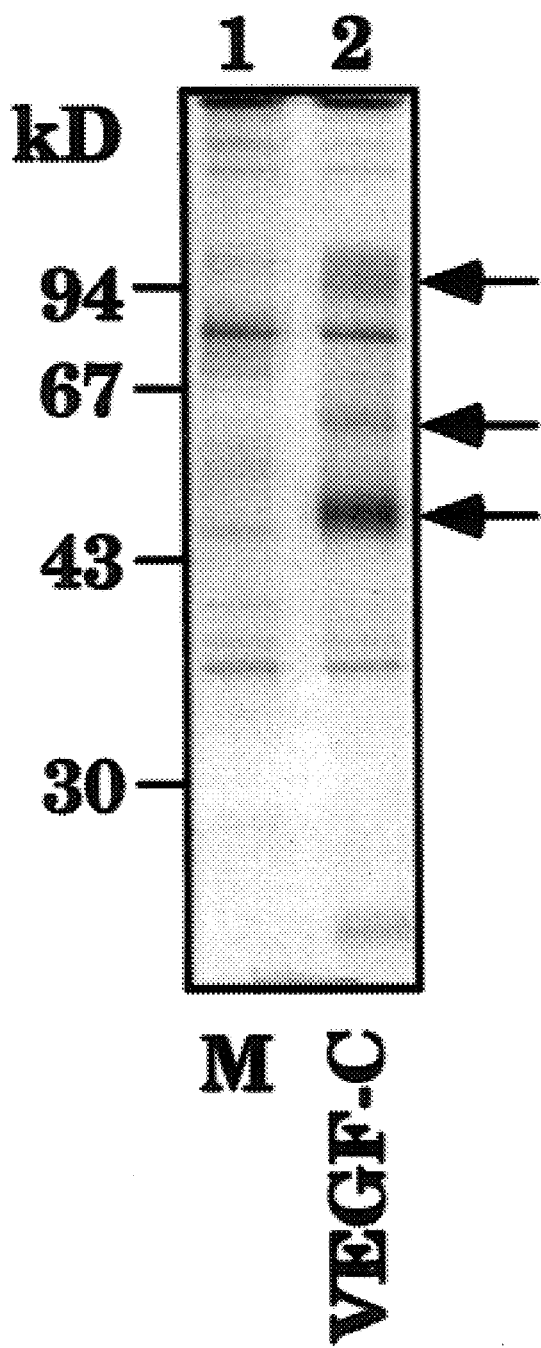
FIG. 13B is a photograph of polyacrylamide gel showing that recombinant VEGF-C forms are disulfide-linked in nonreducing conditions.

In a related experiment, VEGF-C isolated using Flt4EC-Sepharose after a 4 h continuous metabolic labelling was analyzed by polyacrylamide gel electrophoresis in nonreducing conditions (FIG. 13B). Higher molecular mass forms were observed under nonreducing conditions, suggesting that the VEGF-C polypeptides can form disulfide-linked dimers and/or multimers (arrows in FIG. 13B).

EXAMPLE 14

Stimulation of VEGFR-2 Autophosphorylation by VEGF-C

Conditioned medium (CM) from 293 EBNA cells transfected with the VEGF-C vector also was used to stimulate porcine aortic endothelial (PAE) cells expressing VEGFR-2. Pajusola et al., *Oncogene*, 9:3545–55 (1994); Waltenberger et al., *J. Biol. Chem.*, 269:26988–95 (1994). The cells were lysed and immunoprecipitated using VEGFR-2—specific antiserum (Waltenberger et al., 1994).

PAE-KDR cells (Waltenberger et al., 1994) were grown in Ham's F12 medium-10% fetal calf serum (FCS). Confluent NIH3T3-Flt4 cells or PAE-KDR cells were starved overnight in DMEM or Ham's F12 media, respectively, supplemented with 0.2% bovine serum albumin (BSA) and then incubated for 5 min. with the analyzed media. Recombinant human VEGF (R&D Systems) and PDGF-BB were used as a control stimulating agents. The cells were washed twice with ice-cold tris-buffered saline (TBS) containing 100 mM sodium orthovanadate and lysed in RIPA buffer containing 1 mM phenylmethylsulfonyl fluoride (PMSF), 0.1 U/ml aprotinin and 1 mM sodium orthovanadate. The lysates were sonicated, clarified by centrifugation at 16,000 g for 20 min. and incubated for 3–6 h on ice with 3–5 μl of antisera specific for Flt4 (Pajusola et al., 1993), VEGFR-2 or PDGFR-β (Claesson-Welsh et al., *J. Biol. Chem.*, 264:1742–47 (1989); Waltenberger et al., 1994). Immunoprecipitates were bound to protein A-Sepharose, washed three times with RIPA containing 1 mM PMSF, 1 mM sodium orthovanadate, twice with 10 mM Tris-HCl (pH 7.4) and subjected to SDS-PAGE in a 7% gel. Polypeptides were transferred to nitrocellulose by Western blotting and analyzed using PY20 phosphotyrosine-specific monoclonal antibodies (Transduction Laboratories) or receptor-specific antiserum and ECL method (Amersham).

Figure 14A:
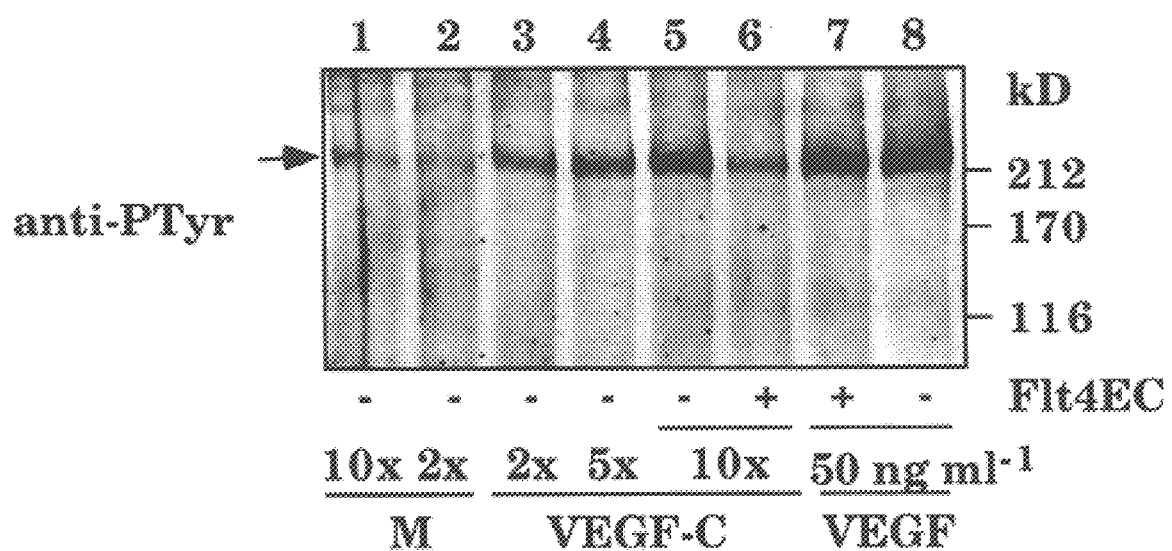
FIGS. 14A and 14B depict Western blots showing that VEGF-C stimulates autophosphorylation of VEGFR-2 (KDR) but has no effect on PDGFR-β phosphorylation.
Figure 14B:
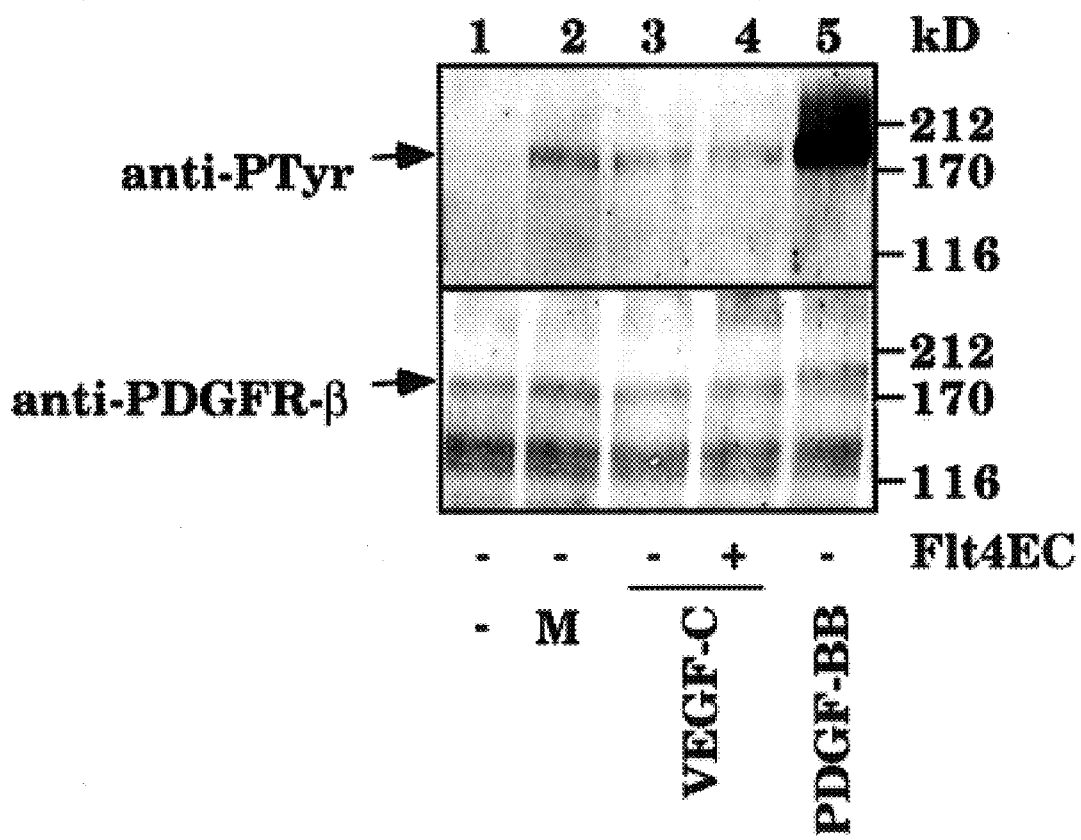

The results of the experiment are presented in FIGS. 14A and 14B. As shown in FIG. 14A, PAE cells expressing VEGFR-2 were stimulated with 10- or 2-fold concentrated medium from mock-transfected 293-EBNA cells (lanes 1 and 2), or with 2-, 5- or 10-fold concentrated medium from 293-EBNA cell cultures expressing the recombinant VEGF-C (lanes 3–6). VEGFR-2 was immunoprecipitated with specific antibodies and analyzed by SDS-PAGE and Western blotting using phosphotyrosine antibodies. For comparison, the stimulations were carried out with non-conditioned medium containing 50 ng/ml of purified recombinant VEGF (lanes 7 and 8). Lanes 6 and 7 show stimulation with VEGF-C- or VEGF- containing media pretreated with Flt4EC. As depicted in FIG. 14B, PDGFR-β-expressing NIH3T3 cells were stimulated with non-conditioned medium (lane 1), 5-fold concentrated CM from mock-transfected (lane 2) or VEGF-C—transfected (lanes 3 and 4) cells, or with non-conditioned medium containing 50 ng/ml of recombinant human PDGF-BB (lane 5). Medium containing VEGF-C was also pretreated with recombinant Flt4EC (lane 4). PDGFR-β was immunoprecipitated with specific antibodies and analyzed by SDS-PAGE and Western blotting using phosphotyrosine antibodies with subsequent stripping and reprobing of the membrane with antibodies specific for PDGFR-β.

A basal level of tyrosine phosphorylation of VEGFR-2 was detected in cells stimulated by CM from the mock-transfected cells. A further concentration of this medium resulted in only a slight enhancement of VEGFR-2 phosphorylation (FIG. 14A lanes 1 and 2). CM containing recombinant VEGF-C stimulated tyrosine autophosphorylation of VEGFR-2 and the intensity of the autophosphorylated polypeptide band was increased upon concentration of the VEGF-C CM (lanes 3–5). Furthermore, the stimulating effect was abolished after pretreatment of the medium with the Flt4EC affinity matrix (compare lanes 1, 5 and 6). The maximal effect of VEGF-C in this assay was comparable to the effect of recombinant VEGF added to unconditioned medium at concentration of 50 ng/ml (lane 8). Pretreatment of the medium containing VEGF with Flt4EC did not abolish its stimulating effect on VEGFR-2 (compare lanes 7 and 8). These results suggest that the VEGF-C expression vector encodes a ligand not only for Flt4 (VEGFR-3), but also for VEGFR-2.

In order to further confirm that the stimulating effect of VEGF-C on tyrosine phosphorylation of VEGFR-3 and VEGFR-2 was receptor-specific, we analyzed the effect of VEGF-C on tyrosine phosphorylation of PDGF receptor β (PDGFR-β) which is abundantly expressed on fibroblastic cells. As can be seen from FIG. 14B, a weak tyrosine phosphorylation of PDGFR-βwas detected upon stimulation of Flt4-expressing NIH3T3 cells with CM from the mock-transfected cells (compare lanes 1 and 2). A similar low level of PDGFR-βphosphorylation was observed when the cells were incubated with CM from the VEGF-C transfected cells, with or without prior treatment with Flt4EC (lanes 3 and 4). In contrast, the addition of 50 ng/ml of PDGF-BB induced a prominent tyrosine autophosphorylation of PDGFR-β (lane 5).

EXAMPLE 15

VEGF-C Stimulates Endothelial Cell Migration in Collagen Gel

CM from cell cultures transfected with the VEGF-C expression vector was placed in a well made in collagen gel and used to stimulate the migration of bovine capillary endothelial (BCE) cells in the three-dimensional collagen gel as follows.

BCE cells (Folkman et al., *Proc. Nat'l Acad. Sci. USA*, 76:5217–5221 (1979) were cultured as described in (Pertovaara et al., *J. Biol. Chem.*, 269:6271–74 (1994)). The collagen gels were prepared by mixing type I collagen stock solution (5 mg/ml in 1 mM HCl) with an equal volume of 2×MEM and 2 volumes of MEM containing 10% newborn calf serum to give a final collagen concentration of 1.25 mg/ml. The tissue culture plates (5 cm diameter) were coated with about 1 mm thick layer of the solution, which was allowed to polymerize at 37° C. BCE cells were seeded on top of this layer. For the migration assays, the cells were allowed to attach inside a plastic ring (1 cm diameter) placed on top of the first collagen layer. After 30 min., the ring was removed and unattached cells were rinsed away. A second layer of collagen and a layer of growth medium (5% newborn calf serum (NCS)), solidified by 0.75% low melting point agar (FMC BioProducts, Rockland, Me.), were added. A well (3 mm diameter) was punched through all the layers on both sides of the cell spot at a distance of 4 mm, and the sample or control media were pipetted daily into the wells. Photomicrographs of the cells migrating out from the spot edge were taken after six days through an Olympus CK 2 inverted microscope equipped with phase-contrast optics. The migrating cells were counted after nuclear staining with the fluorescent dye bisbenzimide (1 mg/ml, Hoechst 33258, Sigma).

Figure 15A:
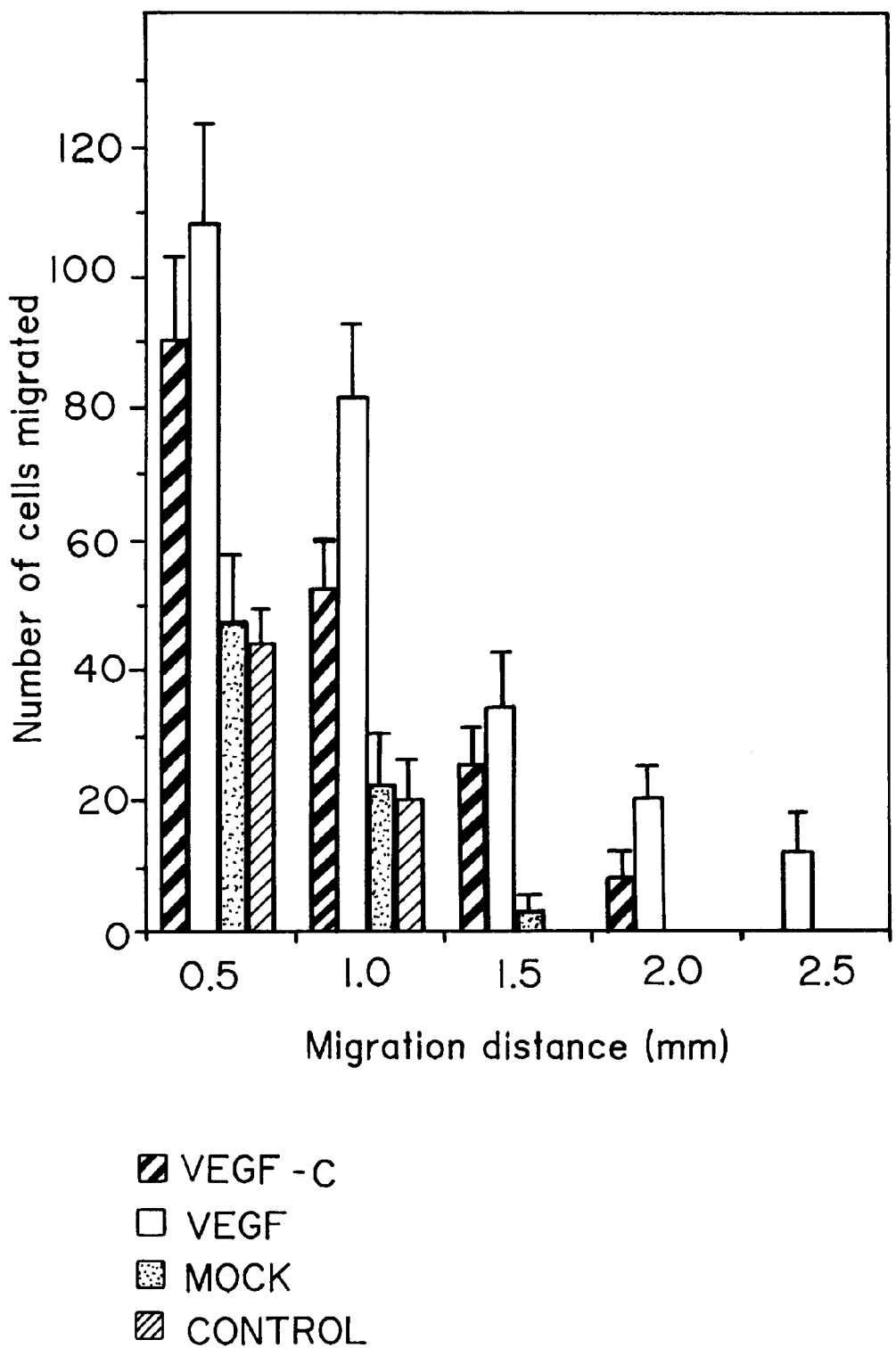
FIGS. 15A and 15B show that VEGF-C stimulates endothelial cell migration in a three-dimensional collagen gel assay.
Figure 15B:
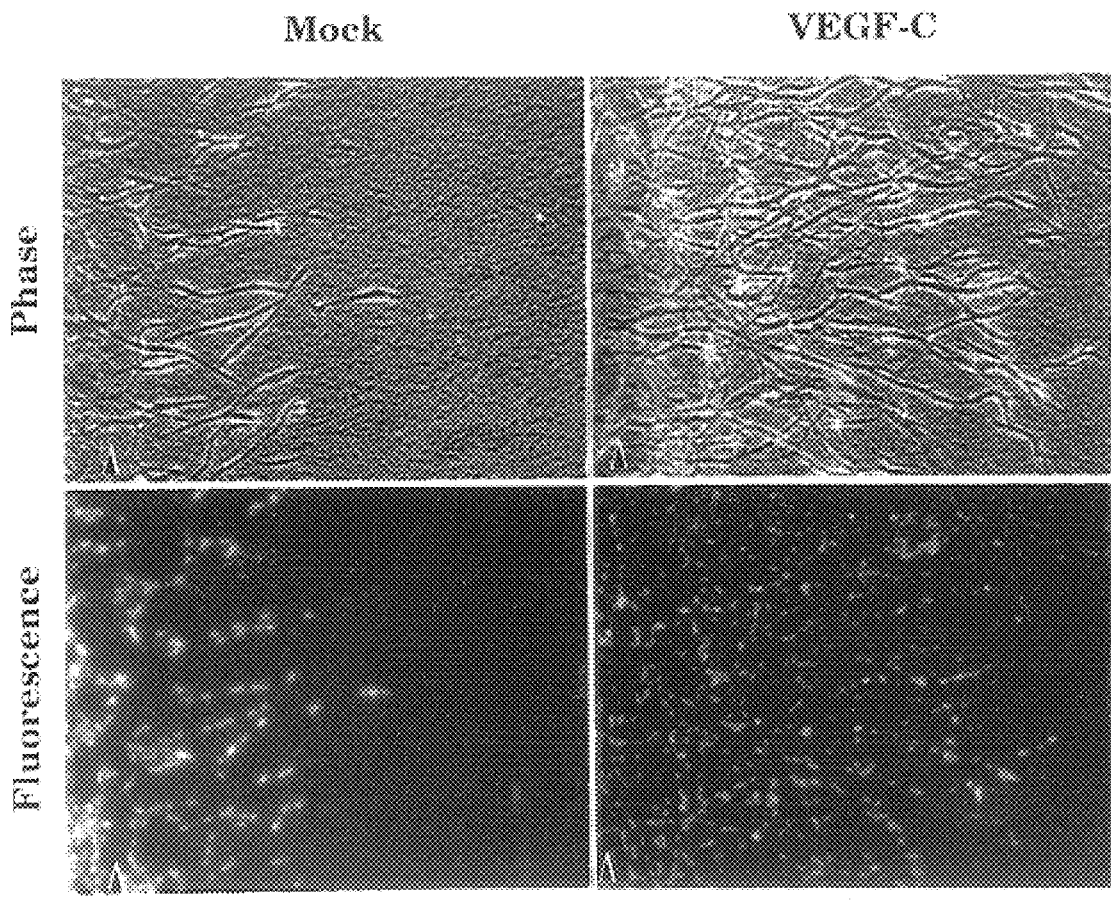

FIG. 15A depicts a comparison of the number of cells migrating at different distances from the original area of attachment towards wells containing media conditioned by the non-transfected (control) or transfected (mock; VEGF-C; VEGF) cells, 6 days after addition of the media. The number of cells migrating out from the original ring of attachment was counted in five adjacent 0.5 mm×0.5 mm squares using a microscope ocular lens grid and 10×magnification. Cells migrating further than 0.5 mm were counted in a similar way by moving the grid in 0.5 mm steps. The experiments were carried out twice with similar results, and medium values from the one of the experiments are presented with standard error bars. The photographs in FIG. 15B depict phase-contrast microscopy and fluorescent microscopy of the nuclear staining of BCE cells migrating towards the wells containing media conditioned by the mock-transfected cells or by VEGF-C—transfected cells. The areas shown is approximately 1 mm×1.5 mm, and arrows indicate the borders of the original ring of attachment.

After 6 days of treatment, the cultures were stained and cells at different distances outside of the original ring of attachment were counted using fluorescent nuclear staining and detection with a fluorescence microscope equipped with a grid. A comparison of the numbers of migrating cells in successive 0.5 mm×0.5 mm areas is shown in FIG. 15A. As can be seen from the columns, VEGF-C-containing CM stimulated cell migration more than medium conditioned by the non-transfected or mock-transfected cells but less than medium from cells transfected with a VEGF expression vector. An example of typical phase contrast and fluorescent microscopic fields of cultures stimulated with medium from mock-transfected or VEGF-C transfected cells is shown in FIG. 15B. Daily addition of 1 ng of FGF2 into the wells resulted in the migration of approximately twice the number of cells when compared to the stimulation by CM from VEGF-transfected cells.

EXAMPLE 16

VEGF-C is Expressed in Multiple Tissues

Figure 16A:
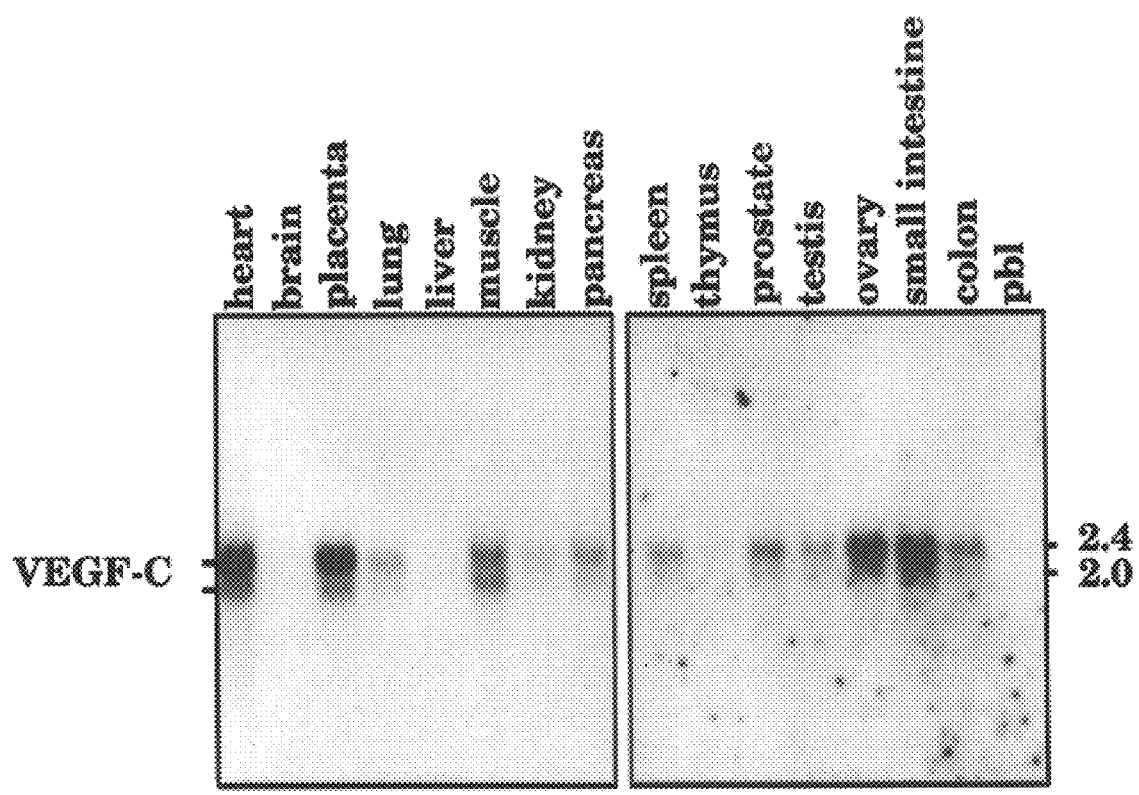
FIG. 16A shows the expression of VEGF-C mRNA in human adult tissues.
Figure 16B:
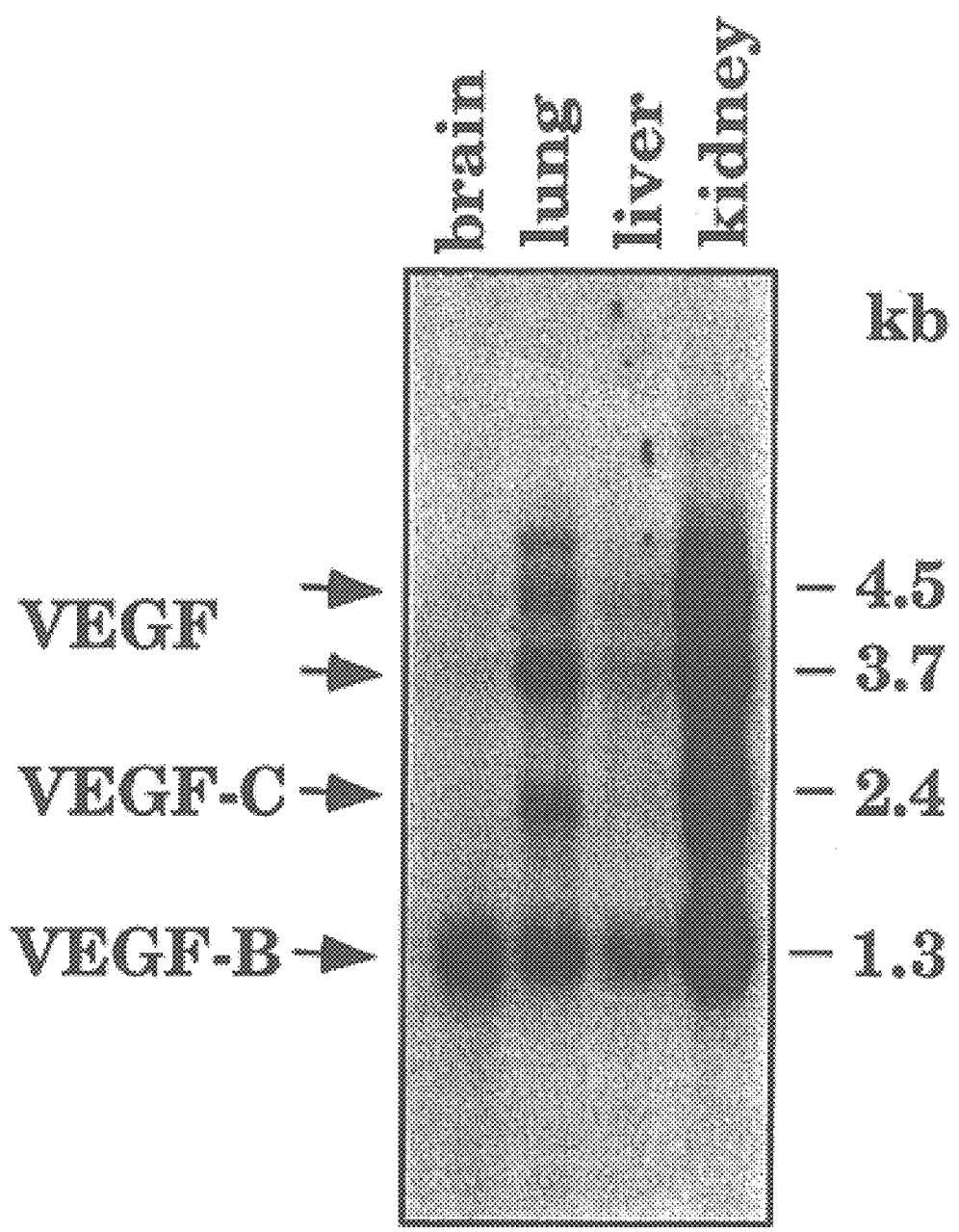
FIG. 16B shows the expression of VEGF, VEGF-B, and VEGF-C in selected human fetal tissues.

Northern blots containing 2 micrograms of isolated poly (A)$^+$ RNA from multiple human tissues (blot from Clontech) were probed with radioactively labelled insert of the 2.0 kb VEGF-C cDNA clone. Northern blotting and hybridization analysis showed that the 2.4 kb RNA and smaller amounts of a 2.0 kb mRNA are expressed in multiple human tissues, most prominently in the heart, placenta, muscle, ovary and small intestine (FIG. 16A). Very little VEGF-C RNA was seen in the brain, liver or thymus and peripheral blood leukocytes (pbl) appeared negative. A similar analysis of RNA from human fetal tissues (FIG. 16B) shows that VEGF-C is highly expressed in the kidney and lung and to a lesser degree in the liver, while essentially no expression is detected in the brain. Interestingly, VEGF expression correlates with VEGF-C expression in these tissues, whereas VEGF-B is highly expressed in all tissues analyzed.

EXAMPLE 17

The VEGF-C Gene Localizes to Chromosome 4q34

A DNA panel of 24 interspecies somatic cell hybrids, which had retained one or two human chromosomes, was used for the chromosomal localization of the VEGF-C gene (Bios Laboratories, Inc., New Haven, Conn.). Primers were designed to amplify an about 250 bp fragment of the VEGF-C gene from somatic cell hybrid DNA. The primers and conditions for polymerase chain reaction (PCR) were 5'-TGAGTGATTTGTAGCTGCTGTG-3' (forward) [SEQ ID NO:34] and 5'-TATTGCAGCAACCCCCACATCT-3' (reverse) [SEQ ID NO:35] for VEGF-C (94° C., 60s/62° C., 45s/72° C., 60s). The PCR products were evaluated by electrophoresis in 1% agarose gels and visualized by ethidium bromide staining in ultraviolet light. [α-$^{32}$P]-dCTP-labelled cDNA inserts of a plasmid representing the complete VEGF-C coding domain was used as a probe in Southern blotting and hybridization analysis of the somatic cell hybrid DNAs as instructed by the supplier (Bios Laboratories).

The cell lines for fluorescence in situ hybridization (FISH) were obtained from the American Type Culture Collection (Rockville, Md.). Purified DNA from P1 clones 7660 and 7661 (VEGF-C) (Genome Systems, Inc., St. Louis, Mo.) were confirmed positive by Southern blotting of Eco RI-digested DNA followed by hybridization with the VEGF-C cDNA. The P1 clones were then labelled by nick translation either with biotin-11-dUTP, biotin-14-ATP (Sigma Chemical Co., St. Louis, Mo.) or digoxigenin 11-dUTP (Boehringer Mannheim GmbH, Mannheim, Germany) according to standard protocols. PHA-stimulated peripheral blood lymphocyte cultures were treated with 5-bromodeoxyuridine (BrdU) at an early replicating phase to induce G-banding. See Takahashi et al., *Human Genet.,* 86:14–16 (1995); Lemieux et al., *Cytogenet. Cell Genet.,* 59:311–12 (1992). The FISH procedure was carried out in 50% formamide, 10% dextran sulphate in 2×SSC using well-known procedures. See, e.g., Rytkönnen et al., *Cytogenet, Cell Genet.,* 68:61–63 (1995); Lichter et al., *Proc. Natl. Acad. Sci. USA,* 85:9664–68 (1988). Repetitive sequences were suppressed with 50-fold excess of Cot-1 DNA (BRL, Gaithersburg, Md.) compared with the labeled probe. Specific hybridization signals were detected by incubating the hybridized slides in labelled antidigoxigenin antibodies, followed by counterstaining with 0.1 mmol/L 4,6-diamino-2-phenylindole. Probe detection for two-color experiments was accomplished by incubating the slides in fluorescein isothiocyanate (FITC)-anti-digoxigenin antibodies (Sigma Chemical Co.) and Texas red-avidin (Vector Laboratories, Burlingame, Calif.) or rhodamine-anti-digoxigenin and FITC-avidin.

Multi-color digital image analysis was used for acquisition, display and quantification of hybridization signals of metaphase chromosomes. The system contains a PXL camera (Photometrics Inc., Tucson, Ariz.) attached to a PowerMac 7100/Av workstation. IPLab software controls the camera operation, image acquisition and Ludl Filter wheel. At least 50 nuclei were scored. Overlapping nuclei and clusters of cells were ignored. A slide containing normal lymphocyte metaphase spreads and interphase nuclei was included in each experiment to control for the efficiency and specificity of the hybridization.

In order to determine the chromosomal localization of the human VEGF-C gene, DNAs from human rodent somatic cell hybrids containing defined sets of human chromosomes were analyzed by Southern blotting and hybridization with the VEGF-C cDNA probe. Among 24 DNA samples on the hybrid panel, representing different human chromosomes, human-specific signals were observed only in hybrids which contained human chromosome 4. The results were confirmed by PCR of somatic cell hybrid DNA using VEGF-C specific primers, where amplified bands were obtained only from DNAs containing human chromosome 4.

Figure 17:
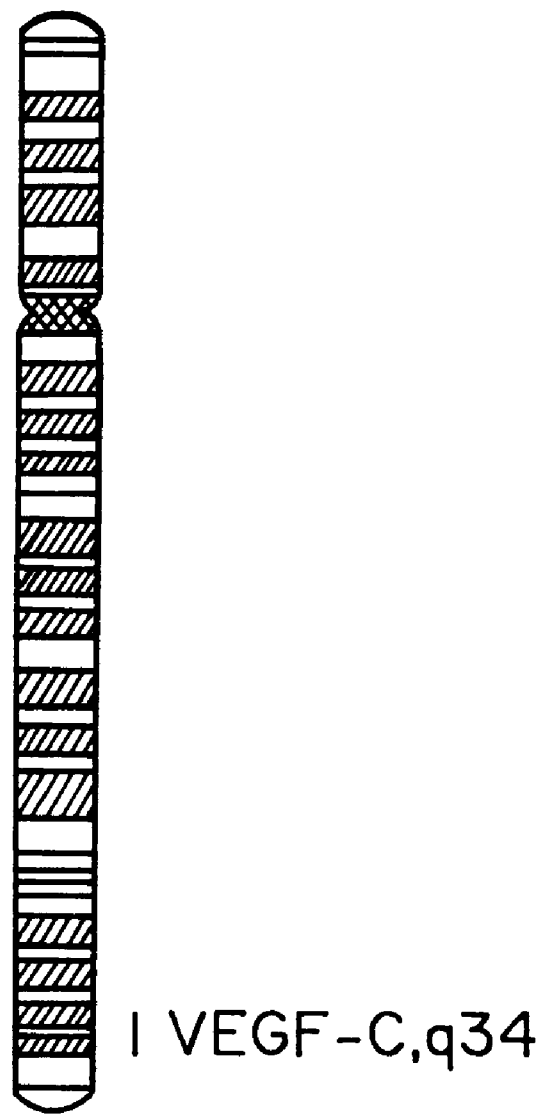
FIG. 17 schematically depicts the chromosomal localization of the VEGF-C gene.

A genomic P1 plasmid for VEGF-C was isolated using specific primers and PCR and verified by Southern blotting and hybridization using a VEGF-C specific cDNA probe. The chromosomal localization of VEGF-C was further studied using metaphase FISH. Using the P1 probe for VEGF-C in FISH a specific hybridization to the 4q34 chromosomal band was detected in 40 out of 44 metaphases (FIG. 17). Double-fluorochrome hybridization using a cosmid probe specific for the aspartylglucosaminidase (AGA) gene showed that VEGF-C is located just proximal to the AGA gene previously mapped to the 4q34–35 chromosomal band.

Biotin labelled VEGF-C P1 and digoxigenin labeled AGA cosmid probes were hybridized simultaneously to metaphase chromosomes. This experiment demonstrated that the AGA gene is more telomerically located than the VEGF-C gene. The foregoing example demonstrates the utility of polynucleotides of the invention as chromosomal markers.

EXAMPLE 18

Figure 18:
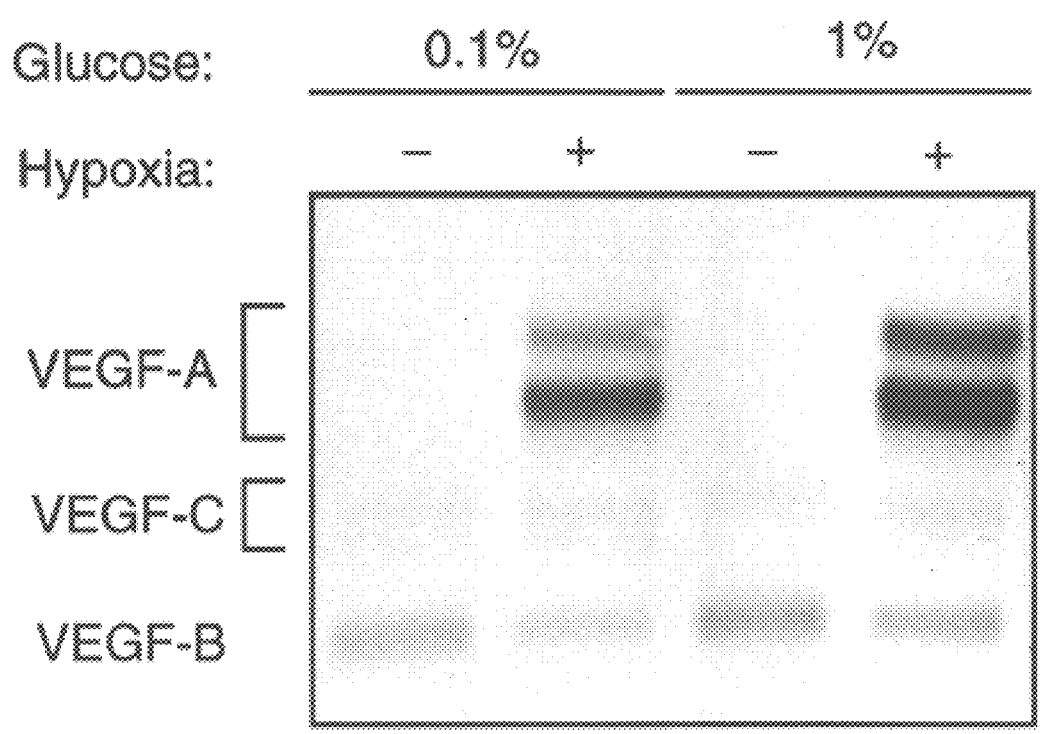
FIG. 18 is a Northern blot hybridization study showing the effects of hypoxia on the mRNA expression of VEGF-A, VEGF-B and VEGF-C.

Effect of Glucose Concentration and Hypoxia on VEGF, VEGF-B and VEGF-C mRNA levels in C6 Glioblastoma Cells Confluent cultures of C6 cells (ATCC CCL 107) were grown on 10 cm diameter tissue culture plates containing 2.5 ml of DMEM and 5% fetal calf serum plus antibiotics. The cultures were exposed for 16 hours to normoxia in a normal cell culture incubator containing 5% $CO_2$ (FIG. 18: lanes marked −) or hypoxia (FIG. 18: lanes marked +) by closing the culture plates in an airtight glass chamber and burning a piece of wood inside until the flame was extinguished due to lack of oxygen. Polyadenylated RNA was isolated (as in the other examples), and 8 micrograms of the RNA was electrophoresed and blot-hybridized with a mixture of the VEGF, VEGF-B and VEGF-C probes (see FIG. 12). The results show that hypoxia strongly induces VEGF-A mRNA expression (compare lanes − and +), both in low and high glucose, but has no significant effect on the VEGF-B mRNA levels. The VEGF-C mRNA isolated from hypoxic cells runs slightly faster in gel electrophoresis and an extra band of faster mobility can be seen below the upper mRNA band. This observation suggests that hypoxia affects VEGF-C RNA processing. One explanation for this observation is that VEGF-C mRNA splicing is altered, affecting the VEGF-C open reading frame and resulting in an alternative VEGF-C protein being produced by hypoxic cells. Such alternative forms of VEGF-C and VEGF-C-encoding polynucleotides are contemplated as an aspect of the invention.

Deposit of Biological Materials: Plasmid FLT4-L has been deposited with the American Type Culture Collection (ATCC), 12301 Parklawn Dr., Rockville Md. 20852 (USA), pursuant to the provisions of the Budapest Treaty, and has been assigned a deposit date of Jul. 24, 1995 and ATCC accession number 97231.

While the present invention has been described in terms of specific embodiments, it is understood that variations and modifications will occur to those in the art. Accordingly, only such limitations as appear in the appended claims should be placed on the invention.

What is claimed is:

1. A purified and isolated nucleic acid comprising a nucleotide sequence that encodes a polypeptide that binds to human Flt4 receptor tyrosine kinase (Flt4), said polypeptide having an amino acid sequence comprising a portion of the amino acid sequence shown in SEQ ID NO: 33 effective to permit such binding, said nucleic acid lacking a nucleotide sequence that encodes the portion of the amino acid sequence shown in SEQ ID NO: 33 that has cysteine motifs of a Balbiani ring 3 protein.

2. A purified and isolated nucleic acid according to claim 1 wherein said polypeptide stimulates tyrosine phosphorylation of human Flt4.

3. A purified and isolated nucleic acid according to claim 2 wherein said polypeptide has an apparent molecular weight of about 23 kD as assessed by SDS polyacrylamide gel electrophoresis under reducing conditions.

4. A purified and isolated nucleic acid according to claim 2 wherein said polypeptide comprises an amino-terminal amino acid sequence set forth in SEQ ID NO: 13.

5. A purified and isolated nucleic acid according to claim 4 wherein said polypeptide comprises approximately 120 amino acids.

6. A purified and isolated nucleic acid according to claim 4 wherein amino terminal amino acids 2 through 18 of said polypeptide have an amino acid sequence identical to amino acids 2 through 18 set forth in SEQ ID NO: 13.

7. A purified and isolated nucleic acid according to claim 2 wherein said polypeptide comprises amino acids 1 to 120 of SEQ ID NO: 33.

8. A purified and isolated nucleic acid according to claim 1 wherein said polypeptide has an apparent molecular weight of about 32 kDa as assessed by SDS polyacrylamide gel electrophoresis under reducing conditions.

9. A nucleic acid according to claim 1 wherein said portion of the amino acid sequence shown in SEQ ID NO: 33 is a continuous portion that includes eight cysteines of SEQ ID NO: 33 that are conserved in human vascular endothelial growth factor (VEGF), human platelet derived growth factor A (PDGF-A), and human platelet derived growth factor B (PDGF-B), and excludes the carboxyl terminal portion of SEQ ID NO: 33 that contains cysteine motifs of a Balbiani ring 3 protein.

10. A nucleic acid according to claim 9 wherein said continuous portion has amino acid 1 of SEQ ID NO: 33 as its amino terminus.

11. A nucleic acid according to claim 1 wherein said portion of the amino acid sequence shown in SEQ ID NO: 33 is a continuous portion having amino acid 1 of SEQ ID NO: 33 as its amino terminal residue, and having as its carboxy terminal residue an amino acid between residues 119 and 126 of SEQ ID NO: 33.

12. A vector comprising a nucleic acid according to claim 1, wherein said vector lacks a nucleotide sequence that encodes the portion of the amino acid sequence shown in SEQ ID NO:33 that has cysteine motifs of a Balbiani ring 3 protein.

13. A host cell transformed or transfected with a vector according to claim 12.

14. A method for producing a polypeptide that binds to the extracellular domain of human Flt4, comprising the steps of:

growing a host cell according to claim 13 under conditions which permit expression by said host cell of a polypeptide that is encoded by said nucleic acid and that binds to the extracellular domain of human Flt4; and isolating said polypeptide from the host cell or the growth medium of the host cell.

15. A method according to claim 14 wherein said host cell is a mammalian host cell that secretes said polypeptide and wherein said isolating step comprises isolating said polypeptide from said growth medium.

16. A purified and isolated nucleic acid comprising a nucleotide sequence that encodes a polypeptide that binds human Flt4 receptor tyrosine kinase (Flt4), said polypeptide having an amino acid sequence comprising a continuous portion of the amino acid sequence shown in SEQ ID NO: 33 effective to permit such binding, said nucleic acid lacking a nucleotide sequence that encodes the carboxy-terminal portion of the amino acid sequence shown in SEQ ID NO: 33 beyond residue 125.

17. A purified and isolated nucleic acid according to claim 16 wherein said encoded polypeptide stimulates tyrosine phosphorylation of human Flt4.

18. A purified and isolated nucleic acid according to claim 16 wherein said nucleic acid lacks a nucleotide sequence that encodes the amino terminal portion of the amino acid sequence shown in SEQ ID NO: 33 that precedes residue 1.

19. An expression construct comprising the nucleic acid according to claim 18 operatively linked to an expression control sequence, said expression construct lacking a nucleotide sequence that encodes the carboxy-terminal portion of the amino acid sequence shown in SEQ ID NO:33 beyond residue 125.

20. A host cell transformed or transfected with the expression construct of claim 19.

21. A method for producing a polypeptide that binds to the extracellular domain of human Flt4 and stimulates tyrosine phosphorylation of Flt4, comprising the steps of:
   growing a host cell according to claim 20 under conditions which permit expression in said host cell of a polypeptide encoded by said nucleic acid and
   isolating said polypeptide from the host cell or the growth medium of the host cell, wherein said polypeptide binds to the extracellular domain of human Flt4 and stimulates phosphorylation of Flt4.

22. A host cell transformed or transfected with a polynucleotide,
   wherein said polynucleotide includes a strand containing a human nucleotide sequence that hybridizes to a DNA comprising the non-coding strand complementary to SEQ ID NO: 32, under the following hybridization conditions:
      (a) hybridization at 42° C. for 20 hours in a solution containing 50% formamide, 5×SSPE, 5×Denhardt's solution, 0.1% SDS and 0.1 mg/ml denatured salmon sperm DNA; and
      (b) washing the filter twice for thirty minutes at room temperature and twice for thirty minutes at 65° C. with a wash solution containing 1×SSC, and 0.1% SDS; and
   wherein said host cell expresses a polypeptide encoded by said polynucleotide,
   wherein said polypeptide has a molecular weight of about 23 kD as assessed by SDS-PAGE under reducing conditions and includes a domain encoded by the human nucleotide sequence that is defined by eight cysteine residues that are conserved in human vascular endothelial growth factor (VEGF), human platelet derived growth factor A (PDGF-A), and human platelet derived growth factor B (PDGF-B),
   wherein said polypeptide lacks any domain that has one or more cysteine motifs of a Balbiani ring 3 protein (BR3P), and
   wherein said polypeptide binds to the extracellular domain of human Flt4 receptor tyrosine kinase.

23. A host cell according to claim 22 that expresses a naturally occurring human Flt4 ligand polypeptide encoded by said polynucleotide.

24. A host cell according to claim 22 wherein said polynucleotide is an expression vector, said expression vector including an expression control sequence operatively linked to sequence that encodes said polypeptide.

25. A host cell transformed or transfected with a polynucleotide comprising a nucleotide sequence that encodes the amino acid sequence shown in SEQ ID NO: 33, wherein said host cell expresses a polypeptide encoded by said polynucleotide, said polypeptide including a contiguous portion of SEQ ID NO: 33 that is sufficient to bind to the extracellular domain of human Flt4 receptor tyrosine kinase (Flt4EC),
   wherein said contiguous portion includes eight cysteine residues that are conserved in human vascular endothelial growth factor (VEGF), human platelet derived growth factor A (PDGF-A), and human platelet derived growth factor B (PDGF-B),
   wherein said polypeptide lacks any portion of SEQ ID NO: 33 that precedes position 1 and lacks any portion of SEQ ID NO: 33 that has one or more cysteine motifs of a Balbiani ring 3 protein (BR3P), and
   wherein said polypeptide has a molecular weight of about 23 kD as assessed by SDS PAGE under reducing conditions and binds to Flt4EC.

26. A host cell according to claim 25 wherein said nucleotide sequence comprises nucleotides 37 to 1086 of the sequence shown in SEQ ID NO: 32.

27. A host cell according to claim 25 wherein said polynucleotide is a vector comprising an expression control sequence operatively linked to the nucleotide sequence that encodes the amino acid sequence shown in SEQ ID NO: 33.

28. A eukaryotic host cell according to claim 22 or 25 that secretes said polypeptide.

29. A host cell comprising the insert of plasmid pFLT4-L, deposited as ATCC accession No. 97231, wherein said host cell expresses and secretes a polypeptide encoded by said insert,
   wherein said secreted polypeptide has a molecular weight of about 23 kD as assessed by SDS-PAGE under reducing conditions and binds to human Flt4 receptor tyrosine kinase and includes a domain defined by eight cysteine residues that are conserved in human vascular endothelial growth factor (VEGF), human platelet derived growth factor A (PDGF-A), and human platelet derived growth factor B (PDGF-B).

30. A host cell transformed or transfected with a polynucleotide comprising a nucleotide sequence that encodes a polypeptide that binds to the extracellular domain of human Flt4 receptor tyrosine kinase,
   wherein said polynucleotide includes a strand containing a human nucleotide sequence that hybridizes to a DNA comprising the non-coding strand complementary to SEQ ID NO: 32, under the following hybridization conditions:
      (a) hybridization at 42° C. for 20 hours in a solution containing 50% formamide, 5×SSPE, 5×Denhardt's solution, 0.1% SDS and 0.1 mg/ml denatured salmon sperm DNA; and
      (b) washing the filter twice for thirty minutes at room temperature and twice for thirty minutes at 65° C. with a wash solution containing 1×SSC, and 0.1% SDS; and
   wherein said host cell expresses and secretes a polypeptide encoded by said polynucleotide, and
   wherein said expressed and secreted polypeptide binds the extracellular domain of human Flt4 receptor tyrosine kinase and has a molecular weight of about 23 kD as assessed by SDS-PAGE under reducing conditions.

31. A method for producing a polypeptide that binds the extracellular domain of human Flt4 receptor tyrosine kinase, comprising the steps of:
   growing a host cell according to any one of claims 21–27, 29, or 30 under conditions which permit expression by said host cell of said polypeptide; and
   isolating said polypeptide from the host cell or the growth medium of the host cell.

32. A method for producing a polypeptide that binds to the extracellular domain (EC) of human Flt4 receptor tyrosine kinase (Flt4), comprising steps of:
   growing a host cell comprising a polynucleotide that comprises a nucleotide sequence that encodes the amino acid sequence set forth in SEQ ID NO:33, under conditions in which the host cell expresses and secretes a polypeptide encoded by the polynucleotide; and
   isolating a polypeptide that binds Flt4 EC from the growth medium of the host cell, said polypeptide having a molecular weight of approximately 23 kD as assessed by SDS-PAGE under reducing conditions and having an amino acid sequence comprising a portion of SEQ ID NO:33 effective to bind Flt4 EC.

33. A method according to claim 32 wherein said polynucleotide comprises an expression vector that comprises a nucleotide sequence that encodes the amino acid set forth in SEQ ID NO:33.

34. A method according to claim 32 wherein said host cell comprises a PC-3 prostatic adenocarcinoma cell (ATCC CRL1435).

35. A method according to claim 32 wherein said polynucleotide comprises the insert of plasma pFLT4-L, deposited as ATCC Accession No. 97231.

* * * * *